United States Patent
Dalton et al.

(10) Patent No.: US 11,207,486 B2
(45) Date of Patent: *Dec. 28, 2021

(54) FLUID MIXING APPARATUS SUCH AS A VENTILATOR

(71) Applicant: Legacy US Inc., Boise, ID (US)

(72) Inventors: Jeffrey Travis Dalton, Boise, ID (US); Jordan Francis Clifford, Boise, ID (US); Travis Andrew Dean, Meridian, ID (US)

(73) Assignee: Legacy US Inc., Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/322,900

(22) Filed: May 18, 2021

(65) Prior Publication Data
US 2021/0370011 A1 Dec. 2, 2021

Related U.S. Application Data

(63) Continuation-in-part of application No. 16/888,564, filed on May 29, 2020, now Pat. No. 11,007,342.

(51) Int. Cl.
*A61M 16/12* (2006.01)
*A61M 16/20* (2006.01)
*A61M 16/10* (2006.01)

(52) U.S. Cl.
CPC ........ *A61M 16/127* (2014.02); *A61M 16/105* (2013.01); *A61M 16/208* (2013.01);
(Continued)

(58) Field of Classification Search
CPC .... B01F 5/043; A61M 16/127; A61M 16/125; A61M 16/12; A61M 16/14; A61M 16/201; A61M 16/206; A61M 16/20; A61M 16/207; A61M 16/208; A61M 16/209; A61M 16/0072; A61M 16/0057; A61M 16/006; A61M 16/0096; A61M 15/0091;
(Continued)

(56) References Cited

U.S. PATENT DOCUMENTS 3,769,973 A 11/1973 Esbenshade
3,881,480 A * 5/1975 Lafourcade ....... A61M 16/0012
128/200.21
(Continued)

OTHER PUBLICATIONS

PCT/US2021/032792 International Search Report.
PCT/US2021/032792 Written Opinion.

*Primary Examiner* — Jan Christopher L Merene
*Assistant Examiner* — Brian T Khong
(74) *Attorney, Agent, or Firm* — CrossPond Law

(57) ABSTRACT

An apparatus such as a fluid mixer, suitable for use with a respirator, including a venturi nozzle for flow of a pressure-controlled fluid; an ambient fluid aperture in fluid communication with the venturi nozzle; a fluid port; a pressure force multiplier in fluid communication with the fluid port; and a valve moveable relative to the venturi nozzle between a start flow position and a stop flow position; where the pressure force multiplier is configured such that fluid forced into the fluid port actuates the valve relative to the venturi nozzle; and where the pressure force multiplier is configured such that fluid withdrawn from the fluid port actuates the valve relative to the venturi nozzle. A method of using an apparatus suitable for a ventilator is also disclosed.

36 Claims, 33 Drawing Sheets

(52) U.S. Cl.
CPC ............... *A61M 2205/3327* (2013.01); *A61M 2205/3331* (2013.01); *A61M 2205/3368* (2013.01); *A61M 2205/3584* (2013.01); *A61M 2205/50* (2013.01); *A61M 2205/8206* (2013.01); *A61M 2230/40* (2013.01); *A61M 2230/63* (2013.01)

(58) Field of Classification Search
CPC .. A61M 2205/3327; A61M 2205/3331; A61M 2205/33; A61M 2205/3368; A61M 2205/3584; A61M 2205/3576; A61M 2205/50; A61M 2230/40
See application file for complete search history.

(56) References Cited

U.S. PATENT DOCUMENTS

| | | | |
|---|---|---|---|
| 4,026,284 A | 5/1977 | Boehringer | |
| 4,239,038 A | 12/1980 | Holmes | |
| 5,584,288 A | 12/1996 | Baldwin | |
| 5,823,179 A | 10/1998 | Grychowski et al. | |
| 5,878,743 A | 3/1999 | Zdrojkowski et al. | |
| 6,425,396 B1 | 7/2002 | Adriance et al. | |
| 6,595,203 B1 | 7/2003 | Bird | |
| 6,634,357 B1 | 10/2003 | Hamilton | |
| 7,059,325 B2 | 6/2006 | Hollis | |
| 9,539,408 B2 | 1/2017 | Pevler | |
| 2007/0227535 A1 | 10/2007 | Harrington et al. | |
| 2009/0293878 A1 | 12/2009 | Tatarek | |
| 2011/0114090 A1* | 5/2011 | Piper | A61M 15/0021 128/200.23 |
| 2012/0012111 A1* | 1/2012 | Howe, Jr. | A61M 16/208 128/205.12 |
| 2012/0060841 A1 | 3/2012 | Crawford, Jr. et al. | |
| 2013/0327323 A1 | 12/2013 | Rubin | |
| 2014/0020687 A1 | 1/2014 | Cullen et al. | |
| 2014/0116427 A1* | 5/2014 | Pevler | A61M 16/0063 128/200.18 |
| 2014/0200475 A1 | 7/2014 | Rubin | |
| 2014/0251328 A1* | 9/2014 | Graboi | A61M 16/0875 128/202.27 |
| 2015/0107592 A1* | 4/2015 | Allum | A61M 16/0051 128/204.21 |
| 2015/0144138 A1 | 5/2015 | Voss et al. | |
| 2016/0200561 A1 | 7/2016 | Dalton et al. | |
| 2017/0254428 A1 | 9/2017 | Barnes | |
| 2017/0260037 A1 | 9/2017 | Dalton et al. | |
| 2018/0008789 A1 | 1/2018 | Alizoti et al. | |
| 2018/0161531 A1* | 6/2018 | Costella | A61M 15/0091 |
| 2018/0200475 A1 | 7/2018 | Allum et al. | |
| 2019/0321570 A1 | 10/2019 | Rubin | |
| 2020/0282173 A1 | 9/2020 | Yasinski et al. | |

* cited by examiner

FLUID MIXING APPARATUS SUCH AS A VENTILATOR

FIELD OF THE INVENTION

The invention generally relates to a fluid mixing apparatus, and more specifically to fluid mixing apparatus such as ventilators usable for human patients suffering from respiratory symptoms of a disease such as COVID-19 or from chronic respiratory ailments, and methods of utilizing such ventilators.

BACKGROUND

As of the filing date of this document, a pandemic of the COVID-19 virus is sweeping Earth. COVID-19 includes a number of symptoms, but is primarily a respiratory disease. The majority of people exposed to the COVID-19 virus have mild symptoms, if any, and return to full health quickly. However, a significant minority of people react extremely badly to exposure to the COVID-19 virus. For those people, their lungs can become infected and inflamed, filling up the alveoli with pus or fluid, becoming clogged, interfering with oxygen transfer to the capillaries. The sickest patients, with the worst response to the COVID-19 virus, may suffer from Acute Respiratory Distress Syndrome (ARDS). Patients with ARDS have lungs that have been badly damaged by the COVID-19 virus, and their alveoli become filled with fluid. Naturally-occurring surfactant in the lungs, which helps the alveoli inflate and deflate, breaks down, making the lungs stiffer. In addition, inflammation from ARDS increases the gap between the alveoli inner surface and the adjacent capillaries, reducing oxygen transfer to the capillaries still further. Patients suffering from such extreme symptoms from COVID-19 infection or other causes must be intubated, and connected to a ventilator, in order to push oxygen into their lungs and improve oxygen transfer to the blood.

As much as intubation and ventilation may be the last line of defense between life and death for patients suffering from severe symptoms of COVID-19 infection, and other patients with ARDS, ventilation is invasive and expensive; another step between no help with breathing at all and full intubated ventilation would be beneficial. Additionally, current ventilators can exhaust droplets exhaled by the patient into the patient's surroundings—typically a hospital room or an intensive care unit. These droplets typically carry the COVID-19 virus from infected patients, placing healthcare workers and other patients at risk.

Further, current ventilators rely on a continuous supply of compressed oxygen in order to function properly; operation of such current ventilators requires the oxygen supply to be continuously flowing. This continuous flow wastes oxygen and increases costs, and makes current ventilators unsuitable for remote locations, locations in less-developed countries, or other locations that lack access or only have minimal access to plentiful and continuous oxygen supplies. Similarly, existing ventilators rely on electronics to control the ventilator, and on electrical power to power the electronics. This need for electricity also makes current ventilators unsuitable for remote locations, locations in less-developed countries, or other locations that lack access or only have minimal access to continuous electricity.

Accordingly, there is a need for an improved ventilator that is less invasive for the patient and presents less risk of infection for people near the ventilated patient Moreover, healthcare inequities are prominent throughout the globe, particularly in low- to middle-income countries (LMIC) like India. Traditional ventilation methods are costly and create an economic burden in the billions of US dollars each year in America alone. In LMICs, access to respiratory care devices like ventilators is limited through not only these high costs, but also a lack of resources such as varied electricity. Traditional ventilation methods are limited in their capacity to provide treatment to the various respiratory needs of people across the globe because they are delicate and require high volumes of infrastructure to operate including the need for a clean space, an electricity source, and normal service and maintenance to remain in optimal performance condition.

Additionally, it is expected that traditional ventilation systems monitor both the clinical performance of the device, as well as the patient system interaction of the device. There is a gap in the monitoring of patient compliance with orders from their doctors for use of respiratory therapy devices. Verifying compliance is an important step in order for medical device companies to receive reimbursement, if there is no way to verify, then companies are not reimbursed for costs to supply their equipment.

There is a need for a new approach to ventilation devices in the medical field to address, at least in part, the deficiencies associated with traditional ventilation devices. In particular, it is desirable to provide a ventilation device that is able to provide treatment to patients in LMICs which lack infrastructure and electricity, as well as a device that can monitor patient compliance which is key for medical device companies to receive reimbursement for devices they supply to patients.

SUMMARY

According to some embodiments, a ventilator, which may be mechanical, relies on the natural breathing of the patient to control the flow of air into a respirator. The airflow provided is at a slightly higher pressure than ambient air pressure, and can also be oxygen enriched to aid patients with breathing difficulties. According to some embodiments, rather than relying on electronics to control the flow of air, a simple and robust mechanical valve is used to shut off the flow of compressed air and/or oxygen into the venturi intake. The valve is activated by the slight pressure changes created when the patient is naturally breathing. The valve can be based on a simple diaphragm and flap valve system, bistable diaphragm system, or spring loaded shuttle system.

According to an aspect of the present invention, there is provided a ventilator including a venturi nozzle for flow of a pressure-controlled fluid; an ambient fluid aperture in fluid communication with the venturi nozzle; a fluid port; a pressure force multiplier in fluid communication with the fluid port; and a valve moveable relative to the venturi nozzle between a start flow position and a stop flow position; where the pressure force multiplier is configured such that fluid forced into the fluid port actuates the valve relative to the venturi nozzle; and where the pressure force multiplier is configured such that fluid withdrawn from the fluid port actuates the valve relative to the venturi nozzle.

According to an aspect of the present invention, there is provided a ventilator connectable to the airway of a living patient, comprising: a venturi, comprising a throat a venturi nozzle a venturi opening in the venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port in fluid communication with the airway of the patient; a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; wherein said pressure force multiplier is configured wherein exhalation of the patient into said fluid port actuates said valve along said axis of movement relative to said venturi nozzle to close said venturi nozzle; wherein said pressure force multiplier is configured wherein inhalation of the patient through said fluid port actuates said valve along said axis of movement relative to said venturi nozzle; and wherein said axis of movement of said valve is substantially longitudinally aligned with a longitudinal direction of said throat.

According to an aspect of the invention, there is provided a ventilator connectable to the airway of a living patient, comprising: a venturi, comprising a throat a venturi nozzle a venturi opening in the venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port in fluid communication with the airway of the patient; a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; wherein said pressure force multiplier is configured wherein exhalation of the patient into said fluid port actuates said valve along said axis of movement relative to said venturi nozzle to close said venturi nozzle; wherein said pressure force multiplier is configured wherein inhalation of the patient through said fluid port actuates said valve along said axis of movement relative to said venturi nozzle; wherein said axis of movement of said valve is substantially longitudinally aligned with a longitudinal direction of said throat; and comprising at least one of a sensor, measurement device, and power-generation device positioned between at least one of: the venturi nozzle and the ambient air aperture; and the pressure force multiplier and the fluid port; and wherein at least one of the sensor, measurement device, and power-generation device comprises at least one of a pressure sensor, oxygen sensor, carbon dioxide sensor, temperature sensor, humidity sensor, piezo sensor, piezo electrical generator, spirometer measurement device, pitot measurement probe, and spirometer electrical generator.

It may be that at least one of the sensor, measurement device, and power-generation device is positioned between the venturi nozzle and the ambient air aperture, and at least one of the sensor, measurement device, and power-generation device is positioned between the pressure force multiplier and the fluid port.

It may be that, for collecting differential data, at least one of the sensor, measurement device, and power-generation device is positioned between the venturi nozzle and the ambient air aperture, and the same type of at least one of a sensor, measurement device, and power-generation device is positioned between the pressure force multiplier and the fluid port.

The ventilator may comprise a central processing unit for packaging raw data collected by at least one of the sensor, measurement device, and power-generation device.

The ventilator may comprise a motion sensor.

The ventilator may comprise exhalation windows for allowing fluid to exit the ventilator during exhalation, and a fluid flow restrictor for at least selectively partially closing the exhalation windows to set the Positive End Expiratory Pressure (PEEP) of the patient. The fluid flow restrictor allows the ventilator to restrict the volume of air that exits the ventilator in a set period, thereby lengthening the exhalation period and thereby allowing PEEP of the patient to be modified to a safer level to avoid collapsing of the lungs, for instance. Additionally, intubated patients often require further procedures such as CT scans which require a patient to be transferred from one breathing device to another. This process of transporting mechanically ventilated patients can create various issues for the patient's health. The brief period of time in which a patient is disconnected from ventilation results in the loss of positive end expiratory pressure (PEEP) and reduces the functional residual capacity (FRC). A significant reduction in FRC for patients with severe Acute Respiratory Distress Syndrome can cause a worsening of hypoxemia. This, in some cases, can take hours for the FRC to improve and the hypoxia to resolve. The present invention addresses at least in part this issue found in traditional methods of transport ventilation by eliminating the reduction in PEEP while switching a patient from a critical care ventilator to a transport ventilator and back again, resulting in a significant improvement in patient care.

According to another aspect, the invention contemplates an apparatus suitable for use with a respirator, comprising: a venturi, comprising: a throat, a venturi nozzle, and; a venturi opening in the venturi nozzle through which pressure-controlled fluid flows outward, wherein said venturi opening opens to said throat, and wherein said venturi opening and said throat are substantially longitudinally aligned; an ambient fluid aperture in fluid communication with said venturi nozzle and with an ambient fluid; a fluid port; a pressure force multiplier in fluid communication with said fluid port; and a valve moveable along an axis of movement relative to said venturi opening in said venturi nozzle between a start flow position that causes entrainment of the ambient fluid by the flow of pressure-controlled fluid within said throat, and a stop flow position that ceases entrainment of the ambient fluid by the flow of pressure-controlled fluid within said throat; wherein said pressure force multiplier is configured such that fluid forced into said fluid port actuates said valve along said axis of movement relative to said venturi nozzle to close said venturi nozzle; wherein said pressure force multiplier is configured such that fluid withdrawn from said fluid port actuates said valve along said axis of movement relative to said venturi nozzle; wherein said axis of movement of said valve is substantially longitudinally aligned with a longitudinal direction of said throat; wherein said pressure force multiplier is positioned between said venturi nozzle and said fluid port; and comprising at least one of a sensor, measurement device, and power-generation device positioned between at least one of: the venturi nozzle and the ambient fluid aperture; and the pressure force multiplier and the fluid port; and wherein at least one of the sensor, measurement device, and power-generation device comprises at least one of a pressure sensor, oxygen sensor, carbon dioxide sensor, temperature sensor, humidity sensor, piezo sensor, piezo electrical generator, spirometer measurement device, pitot measurement probe, and spirometer electrical generator.

It may be that at least one of the sensor, measurement device, and power-generation device is positioned between the venturi nozzle and the ambient air aperture, and at least one of the sensor, measurement device, and power-generation device is positioned between the pressure force multiplier and the fluid port.

It may be that, for collecting differential data, at least one of the sensor, measurement device, and power-generation device is positioned between the venturi nozzle and the ambient air aperture, and the same type of at least one of a sensor, measurement device, and power-generation device is positioned between the pressure force multiplier and the fluid port.

The apparatus may comprise a central processing unit for packaging raw data collected by at least one of the sensor, measurement device, and power-generation device.

The apparatus may comprise a motion sensor.

The apparatus may comprise at least one fluid gate for allowing fluid to exit the apparatus when fluid is forced into said fluid port, and a fluid flow restrictor for at least selectively partially closing the at least one fluid gate.

The apparatus may further comprise a pressure regulator for regulating the flow of the pressure-controlled fluid, the pressure regulator comprising: a housing formed to include a bore therein; a piston moveably disposed within said bore, wherein said piston comprises an annular lip adjacent a first end thereof; a spring disposed within said bore, and comprising a first end and a second end; an adjustment cap moveably disposed in said bore, wherein said adjustment cap is formed to include a plurality of key slots formed therein; wherein: said first end of said spring is in physical contact with said annular lip; and said second end of said spring is in physical contact with said adjustment cap wherein: rotating said adjustment cap in a first direction causes said adjustment cap to compress said first spring; rotating said adjustment cap in a second and opposite direction causes said adjustment cap to decompress said spring; rotating said adjustment cap in said first direction increases the output pressure of the pressure regulator; rotating said adjustment cap in said second direction decreases the output pressure of the pressure regulator; said bore is defined by a cylindrical wall; said cylindrical wall is formed to include a first threading therein; said adjustment cap is formed to include a second threading formed on a periphery thereof; and said second threading is configured to mesh with said first threading.

The pressure force multiplier may comprise a diaphragm.

It may be that said valve includes a stem with a tapered end, wherein said tapered end enters said venturi opening in said venturi nozzle in said stop position to substantially close said venturi opening.

The apparatus may further comprise at least one filter detachably connected to said ambient fluid aperture.

It may be that said pressure-controlled fluid is a liquid.

In another aspect, the invention comprehends a method of using an apparatus suitable for a ventilator and collecting data from a patient, the method comprising: providing a pressure-controlled oxygen source; providing an apparatus suitable for a ventilator, comprising: a venturi, comprising a throat a venturi nozzle; a venturi opening in said venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port; a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; placing said fluid port in fluid communication with an airway of the patient; in response to exhalation by the patient through said fluid port, causing said at least one flap to move to said closed position relative to said at least one opening, and actuating said valve along said axis of movement relative to said venturi nozzle to close said venturi nozzle; and in response to inhalation by the patient through said fluid port, causing said at least one flap to move to said open position relative to said at least one opening, and actuating said valve along said axis of movement relative to said venturi nozzle; and wherein said axis of movement of the valve is substantially longitudinally aligned with the longitudinal direction of the throat; and comprising at least one of a sensor, measurement device, and power-generation device positioned between at least one of: the venturi nozzle and the ambient air aperture; and the pressure force multiplier and the fluid port; and wherein at least one of the sensor, measurement device, and power-generation device comprises at least one of a pressure sensor, oxygen sensor, carbon dioxide sensor, temperature sensor, humidity sensor, piezo sensor, piezo electrical generator, spirometer measurement device, pitot measurement probe, and spirometer electrical generator; and collecting raw data using the at least one of the sensor, measurement device, and power-generation device; packaging the collected raw data using a central processing unit; transmitting the packaged raw data to a receiving device using a wired or wireless communication link; receiving the packaged data on the receiving device; unpackaging the collected raw data; quantizing the unpackaged raw data; formatting the quantized data; analyzing the formatted data; distributing the analyzed data; and displaying the analyzed data using an application.

The method may comprise the step of coupling the central processing unit to the ventilator.

It may be that using the wireless communication link comprises using at least one wireless protocol selected from the BLUETOOTH® wireless protocol of the Bluetooth SIG, Kirkland, Wash., the WI-FI® wireless protocol of the Wi-Fi Alliance, Austin, Tex., and the THREAD® wireless protocol of Thread Group, Inc., San Ramon, Calif.

It may be that using the wired communication link comprises using at least one of a USB, serial, 1-wire, and parallel.

The method may comprise displaying the analyzed data using a smart device.

It may be that the smart device comprises at least one of a mobile communication device, a tablet, a patient interface display, a laptop computer, and a desktop computer.

According to another aspect, the invention envisages an active filter comprising at least one piezo element and at least one dielectric filter medium, wherein the piezo element generates electricity to induce a static charge in the dielectric filter medium.

The use of piezoelectricity in this device will be used to power sensors for data collection and data transmission disclosed herein. By placing a piezoelectric crystal between the metal walls in the device, electric charges are generated as mechanical pressure driven by a patient's breathing is applied to the metal. Essentially, this pressure generates electricity by throwing the crystal out of balance. This can produce power up to 2 mW, similar to that stored in Lithium batteries, generating enough power in order for the device sensors to collect and transmit data. The limiter 72 and/or the ribs 74 shown in FIG. 2A, for example, may be piezo elements or covered with piezo elements that are capable of generating electricity due to actuation of ventilator, and particularly due to the flange 38 impacting the limiter 72 (which goes on to vibrate the ribs 74 on impact).

It may be that the power generated by the at least one piezo element is AC.

The active filter may comprise at least one spirometer that generates electricity to induce a static charge in the at least one dielectric filter medium.

The active filter may comprise two spirometers that generates electricity to induce a static charge in the at least one dielectric filter medium.

It may be that the power generated by the at least one spirometer is DC.

It may be that the inhalation of the patient through said fluid port actuates said valve relative to said venturi nozzle to open said venturi nozzle.

It may be that the exhalation of the patient into said fluid port causes said at least one flap to move to said closed position relative to said at least one opening in said pressure force multiplier.

It may be that the inhalation of the patient through said fluid port causes said at least one flap to move to said open position relative to said at least one opening in said pressure force multiplier.

According to another aspect, the present invention contemplates an apparatus suitable for a ventilator, including a venturi nozzle for flow of a pressure-controlled fluid; an ambient fluid aperture in fluid communication with the venturi nozzle; a fluid port; a pressure force multiplier in fluid communication with the fluid port; and a valve moveable relative to the venturi nozzle between a start flow position and a stop flow position; where the pressure force multiplier is configured such that fluid forced into the fluid port actuates the valve relative to the venturi nozzle; and where the pressure force multiplier is configured such that fluid withdrawn from the fluid port actuates the valve relative to the venturi nozzle.

According to another aspect, the present invention contemplates an apparatus suitable for use with a respirator, comprising: a venturi, comprising: a throat, a venturi nozzle, and; a venturi opening in the venturi nozzle through which pressure-controlled fluid flows outward, wherein said venturi opening opens to said throat, and wherein said venturi opening and said throat are substantially longitudinally aligned; an ambient fluid aperture in fluid communication with said venturi nozzle and with an ambient fluid; a fluid port; a pressure force multiplier in fluid communication with said fluid port; and a valve moveable along an axis of movement relative to said venturi opening in said venturi nozzle between a start flow position that causes entrainment of the ambient fluid by the flow of pressure-controlled fluid within said throat, and a stop flow position that ceases entrainment of the ambient fluid by the flow of pressure-controlled fluid within said throat; wherein said pressure force multiplier is configured such that fluid forced into said fluid port actuates said valve along said axis of movement relative to said venturi nozzle to close said venturi nozzle; wherein said pressure force multiplier is configured such that fluid withdrawn from said fluid port actuates said valve along said axis of movement relative to said venturi nozzle; wherein said axis of movement of said valve is substantially longitudinally aligned with a longitudinal direction of said throat; and wherein said pressure force multiplier is positioned between said venturi nozzle and said fluid port. Thus, the present invention does not rely on the pressure-controlled fluid to be continuously flowing as is commonly the case with known constructions. Therefore, significant savings, both economic and environmental, can be made due to the present invention actuating the valve to regulate the flow of the pressure-controlled fluid which in effect makes the overall process more efficient. The apparatus may be particularly suitable for remote locations, locations in less-developed countries, or other locations that lack access or only have minimal access to plentiful and continuous fluid supplies.

The pressure force multiplier may be configured such that the (any) fluid forced into the fluid port actuates the valve relative to the venturi nozzle to a stop flow position; and the pressure force multiplier may be configured such that the (any) fluid withdrawn from the fluid port actuates the valve relative to the venturi nozzle to a start flow position.

The pressure force multiplier may be configured such that the (any) fluid forced into the fluid port actuates the valve relative to the venturi nozzle to a start flow position; and the pressure force multiplier may be configured such that the (any) fluid withdrawn from the fluid port actuates the valve relative to the venturi nozzle to a stop flow position. This may be considered a reverse configuration, for instance.

The pressure force multiplier may be configured such that the (any) fluid forced into the fluid port actuates the valve relative to the venturi nozzle to an active flow position between the start flow position and stop flow position; and the pressure force multiplier may be configured such that the (any) fluid withdrawn from the fluid port actuates the valve relative to the venturi nozzle to an active flow position between the start flow position and stop flow position. In such a configuration, both actions of a fluid being forced into the fluid port and a fluid being withdrawn from the fluid port can actuate the valve to an active flow position. This may be considered a point anywhere between the stop flow and start flow positions. Hence, the flow may be completely controlled and/or regulated from the stop flow to start flow and all positions therebetween.

The apparatus may be defined such that a pressure-controlled fluid includes oxygen, an ambient fluid includes ambient air, fluid forced into the fluid port includes air exhaled into an air port, and fluid withdrawn from the fluid port includes air inhaled from an air port.

It may be that the pressure force multiplier is positioned between the venturi nozzle and the fluid port. Such a positioning may provide enhanced actuation of the valve.

The venturi nozzle may be positioned between the pressure force multiplier and the fluid port. The inventors consider such a positioning may also provide enhanced actuation of the valve.

It may be that the venturi nozzle is positioned between the ambient fluid aperture and the fluid port. The inventors found such a positioning may also provide enhanced actuation of the valve.

The apparatus may comprise a pressure regulator for regulating the flow of a pressure-controlled fluid. It will be appreciated that at least one of many different pressure regulators suitable for the purpose of regulating the flow of the pressure-controlled fluid may be included.

More particularly, the apparatus may comprise a pressure regulator (for regulating the flow of the pressure-controlled fluid) comprising a housing formed to include a bore therein; a piston moveably disposed within the bore, wherein the piston includes an annular lip adjacent a first end thereof; a spring disposed within the bore, and comprising a first end and a second end; an adjustment cap moveably disposed in the bore, where the adjustment cap is formed to include a plurality of key slots formed therein; wherein: the first end of the spring is in physical contact with the annular lip; and the second end of the spring is in physical contact with the adjustment cap wherein: rotating the adjustment cap in a first direction causes the adjustment cap to compress the first spring; rotating the adjustment cap in a second and opposite direction causes the adjustment cap to decompress the spring; rotating the adjustment cap in the first direction increases the output pressure of the pressure regulator; rotating the adjustment cap in the second direction decreases the output pressure of the pressure regulator; the bore is defined by a cylindrical wall; the cylindrical wall is formed to include a first threading therein; the adjustment cap is formed to include a second threading formed on a periphery thereof; and the second threading is configured to mesh with the first threading. Such a regulator may be particularly effective at regulating the flow of the pressure-controlled fluid. The inventors have found such a pressure regulator to have particularly good synergy with the apparatus defined herein. This synergy makes such a pressure regulator a specific selection generating enhanced performance of the apparatus.

The pressure force multiplier may comprise a diaphragm. The diaphragm may be saucer-shaped to enhance its function.

It may be that the pressure force multiplier is bi-stable. This may be in an inhalation configuration and an exhalation configuration. In this way, the pressure force multiplier expresses two stable states which is particularly beneficial in at least some embodiments of the present invention.

The pressure force multiplier may be biased toward the stop flow position. In some embodiments, it may be preferred that the pressure force multiplier be biased toward the stop flow position, and such an arrangement makes this possible.

The pressure force multiplier may be biased toward the start flow position.

Conversely, or additionally, in some embodiments, it may be preferred that the pressure force multiplier be biased toward the start flow position, and such an arrangement makes this possible.

The pressure force multiplier may include at least one flap.

It may be that the apparatus is solely mechanical. According to some embodiments, the apparatus being solely mechanical provides the benefit of simplicity of manufacture and operation.

The apparatus may be configured such that in the start flow position or an active flow position a mixture of pressure-controlled fluid and ambient fluid is allowed to flow to the fluid port. For example, it may be that the ambient fluid, such as ambient air, becomes entrained with the flow of the pressure-controlled fluid, such as oxygen, driving flow and movement towards the fluid port.

The flow of the mixture may be modulated in real-time. The apparatus may, therefore, control, change, and/or regulate the flow of the fluid mixture in an alternative or additional way to the regulation of the flow of the pressure-controlled fluid alone.

It may be that the valve includes a flange that is connected to the pressure force multiplier.

The valve may include a stem with a tapered end, where the tapered end enters a venturi opening in the venturi nozzle in the stop position to substantially close the venturi opening. Such an arrangement may be particularly effective in operation of the valve in relation to the features of the apparatus defined herein, It may be that the stem is connected to the pressure force multiplier. Such a configuration may make the stem and force multiplier more robust during operation.

The valve may comprise a switch. This may be particularly effective when a binary system is desired, or binary states are desired.

It may be that the valve includes a flap valve.

The valve may comprise a spring-loaded shuttle system.

The valve may be slidable.

The valve may be solely mechanical.

It may be that the ambient fluid aperture includes a fluid exhaust. The ambient fluid aperture may, therefore, have the dual function of allowing ingress and egress of fluid. Exhaustion of fluid from the apparatus may reduce contamination by used fluids within the apparatus, and may simplify the apparatus by eliminating the need to store used fluid that is not exhausted.

The valve may be configured to be actuated relative to the venturi nozzle while simultaneously opening the fluid exhaust. Such a dual functionality may improve the operational efficiency of the apparatus.

The apparatus may further comprise at least one filter detachably connected to the ambient fluid aperture. The filter may operate to filter incoming and/or outgoing fluid to/from the apparatus. Filtration of both incoming and outgoing fluid with a single filter may improve the operational efficiency of the apparatus.

The at least one filter may comprise pores of about 3 μm. This pore size is particularly effective in removing contaminants such as viruses and bacteria from fluid such as air, for example.

The apparatus may further comprise a respirator or similar apparatus that provides for fluid communication between the ventilator and the airway of a patient. The inventors have discovered that the respirator used in combination with the apparatus or forming part of the apparatus may be particularly effective in treating respiratory conditions such as COVID-19.

The respirator may be in fluid communication with the fluid port. The fluid port may be connected directly or indirectly to the respirator, for instance.

The fluid described herein above may be a liquid. In various applications, liquid may pass through the apparatus.

It will be appreciated that liquid such as medicine may also be administered using the apparatus. For instance, the apparatus may thus function as an improved nebulizer or vaporizer that can be used to administer medication in the form of a liquid mist that can be inhaled into the lungs by a patient suffering from a respiratory disease or condition. It will be appreciated, however, that any suitable liquid may be utilized with the apparatus.

The apparatus may be injection molded. The apparatus may thus be quickly reproduced in a cost-effective manner.

It may be that the apparatus is fabricated by additive manufacturing, such as a 3D printing process. The apparatus may, therefore, be reproduced accurately and in a cost-effective manner, which makes it particularly attractive in less-developed countries.

The apparatus may be configured to be mobile.

The apparatus may be configured to be re-usable. Since the apparatus may be effectively be cleaned, it may be suitable for re-use. This is particularly beneficial in less-developed countries where availability of new apparatus are not readily available.

The apparatus described herein may be for use in controlling the flow of air and/or oxygen into a respirator.

The apparatus described herein may be for use in controlling the flow of scrubbed air and/or oxygen into a respirator.

The apparatus described herein may be for use in treating a respiratory condition.

The apparatus described herein may be for use in treating COVID-19.

In another aspect, the present invention envisages a method of using an apparatus suitable for a ventilator, the method including providing a source of pressure-controlled fluid; providing an apparatus suitable for a respirator, including: a venturi nozzle for receiving a flow of the pressure-controlled fluid; an ambient fluid aperture in fluid communication with the venturi nozzle; a fluid port; a pressure force multiplier in fluid communication with the fluid port; and a valve moveable relative to the venturi nozzle between a start flow position, in which the pressure-controlled fluid mixes with the ambient fluid, and a stop flow position; actuating the valve relative to the venturi nozzle in response to fluid forced into the fluid port; and actuating the valve relative to the venturi nozzle in response to fluid withdrawn from the fluid port.

In another aspect, the present invention envisages a method of using an apparatus suitable for a ventilator, the method comprising: providing a pressure-controlled oxygen source; providing an apparatus suitable for a ventilator, comprising: a venturi, comprising a throat; a venturi nozzle; a venturi opening in said venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port; a pressure force multiplier in fluid communication with said fluid port, wherein said pressure force multiplier includes at least one opening defined therethrough; said pressure force multiplier comprising at least one flap moveable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; placing said fluid port in fluid communication with an airway of the patient; in response to exhalation by the patient through said fluid port, causing said at least one flap to move to said closed position relative to said at least one opening, and actuating said valve along said axis of movement relative to said venturi nozzle to close said venturi nozzle; and in response to inhalation by the patient through said fluid port, causing said at least one flap to move to said open position relative to said at least one opening, and actuating said valve along said axis of movement relative to said venturi nozzle; and wherein said axis of movement of the valve is substantially longitudinally aligned with the longitudinal direction of the throat.

The apparatus in such a method may be solely mechanical.

It may be that at least a portion of said valve is movable, along said axis of movement, within said throat.

The method may further comprise adjusting the pressure of the pressure-controlled fluid.

It may be that the method includes that the pressure-controlled fluid is pressure-controlled oxygen, and where the fluid is air, the method including: connecting the apparatus to a respirator or similar apparatus; placing the ventilator in gaseous communication with the patient and with the source of pressure-controlled oxygen; in response to inhalation by the patient, starting oxygen flow into the ventilator, mixing the oxygen with ambient air to generate enriched air, and delivering the enriched air to the patient; in response to exhalation by the patient, stopping oxygen flow into the ventilator, and exhausting exhalation air from the ventilator.

The enriched air may have an FiO2 of at least 26%.

It may be that the method includes that the pressure-controlled fluid is pressure-controlled filtered air, and where the fluid is air, the method including: connecting the apparatus to a respirator or similar apparatus; placing the ventilator in gaseous communication with the patient and with the source of pressure-controlled filtered air; in response to inhalation by the patient, starting oxygen flow into the ventilator, mixing the pressure-controlled filtered air with ambient air to generate scrubbed air, and delivering the scrubbed air to the patient; in response to exhalation by the patient, stopping oxygen flow into the ventilator, and exhausting exhalation air from the ventilator.

The scrubbed air may have an FiO2 of at least 26%.

The method may further include walking and/or running while utilizing the apparatus and a respirator or similar apparatus. This may involve use of the apparatus while the user is exercising, for instance.

The method may further include initiating use of the apparatus and respirator or similar apparatus to treat allergies.

The method may further include initiating use of the apparatus and respirator or similar apparatus to treat ARDS.

The method may further include initiating use of the apparatus and respirator or similar apparatus to treat sleep apnea.

The method may further include initiating use of the apparatus and respirator or similar apparatus to treat COPD.

The method may further include initiating use of the apparatus and respirator or similar apparatus to treat infection by the COVID-19 virus.

The method may further include filtering the ambient air.

The method may further include filtering exhaled breath from the patient.

In another aspect, the present invention encompasses a pressure force multiplier including a sealed end and an open end, where the sealed end is in fluid communication with a valve to define a fixed volume between the sealed end and the valve, where the pressure force multiplier is configured such that a change in pressure in the open end causes a change in pressure in the sealed end which actuates the valve. Such a force multiplier may be particularly effective for use with the apparatus defined herein. However, this pressure force multiplier is considered inventive in its own right.

The pressure force multiplier may be configured such that a negative pressure in the open end causes a reduction in pressure in the sealed end which actuates the valve.

The pressure force multiplier may be configured such that a positive pressure in the open end causes an increase in pressure in the sealed end which actuates the valve.

It may be that the actuation of the valve activates a humidifier.

The actuation of the valve may generate a change in a visual indicator. The visual indicator may be a change in color, for instance.

The change in visual indicator may represent a change of pressure in the open end.

It may be that the change of pressure in the open end is caused by inhalation and/or exhalation of a patient. The pressure force multiplier is, thus, adaptable for many different applications, which makes it a particularly useful accessory in many different fields of operation.

The characteristics and utilities of the present invention described in this summary and the detailed description below are not all inclusive. Many additional features and advantages will be apparent to one of ordinary skill in the art given the following description. There has thus been outlined, rather broadly, the more important features of the invention in order that the detailed description thereof that follows may be better understood, and in order that the present contribution to the art may be better appreciated.

BRIEF DESCRIPTION OF THE DRAWINGS

The use of the same reference symbols in different figures indicates similar or identical items.

DETAILED DESCRIPTION

Figure 1:
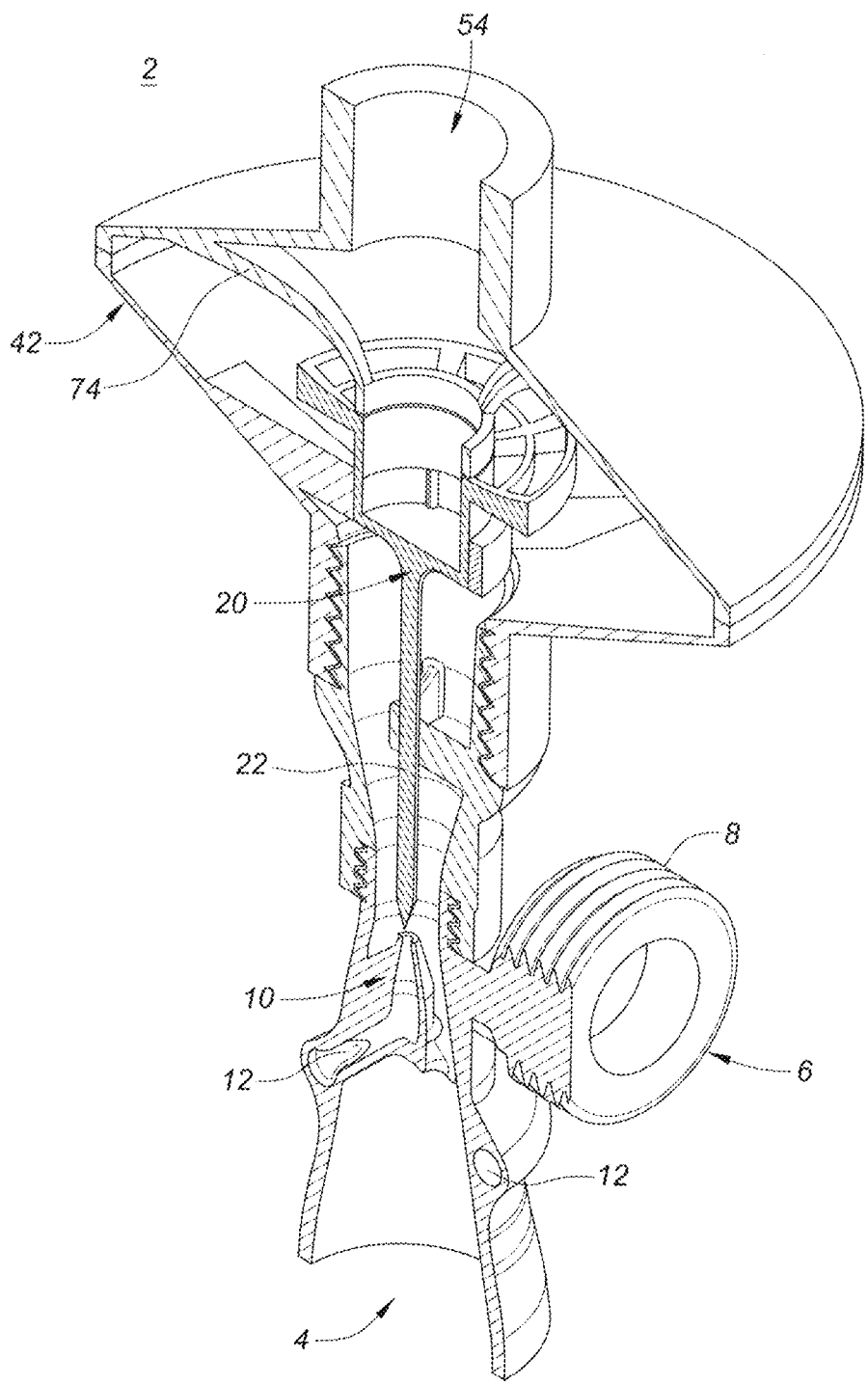
FIG. 1 is a perspective cutaway view of a ventilator in an inhalation configuration.
Figure 2:
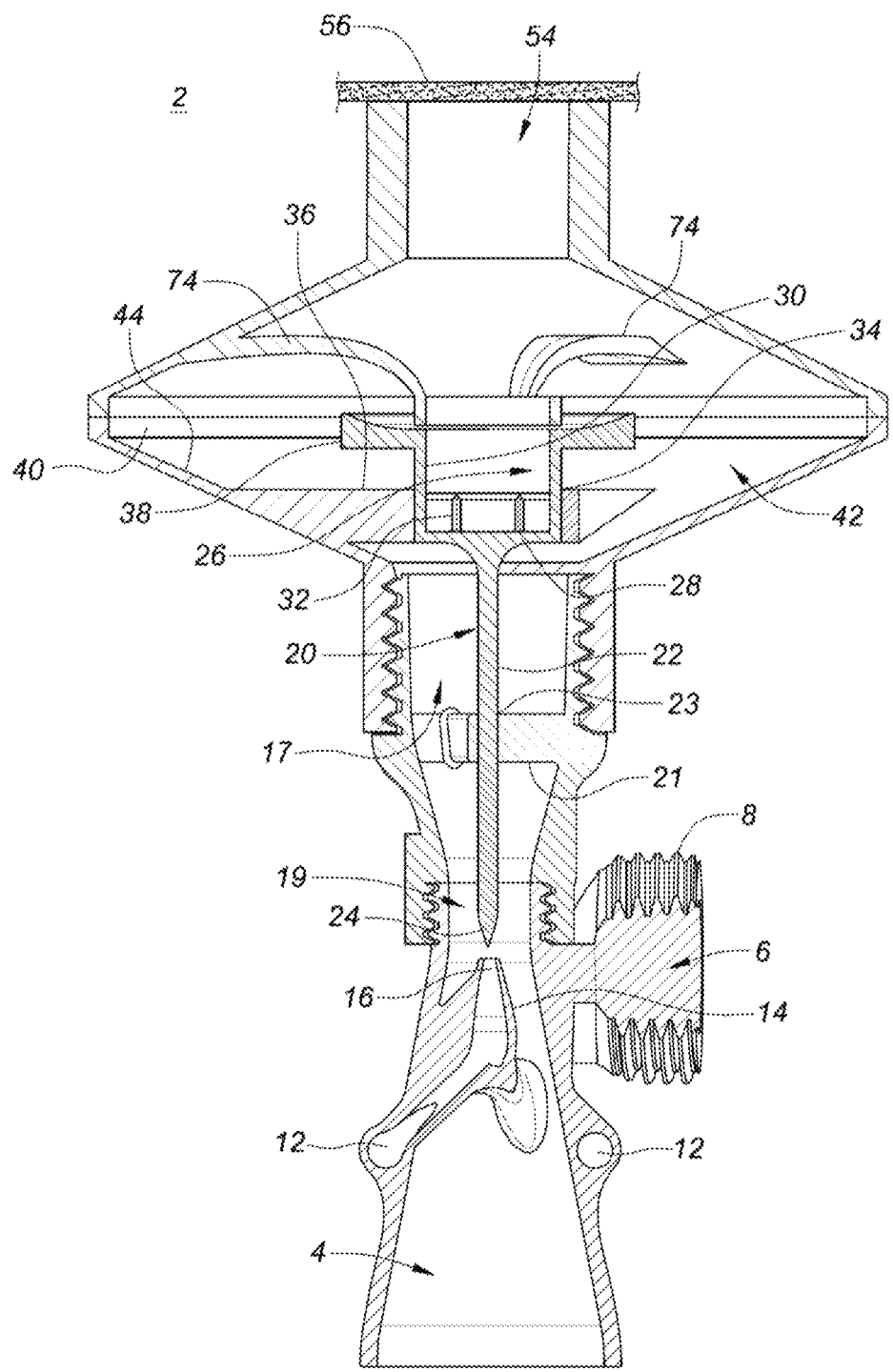
FIG. 2 is a side cutaway view of the ventilator of FIG. 1 in the inhalation configuration.

Referring to FIGS. 1-2, one embodiment of a fluid mixer 2 is shown. The fluid mixer 2 also may be referred to as a fluid mixing apparatus 2 or apparatus 2. The fluid mixer 2 may be used in a variety of applications. For example, the fluid mixer 2 may find use in medical applications, automotive applications, racing applications, and other applications. As seen in FIGS. 1-2, the fluid mixer 2 is a ventilator 2. The term "ventilator," as used in this document, encompasses any and all medical applications in which the ventilator 2 may be used, such as but not limited to continuous positive airway pressure (CPAP) machines, and bilevel positive airway pressure (BiPAP) machines.

Returning to FIGS. 1-2, an exemplary ventilator 2 is shown in an inhalation configuration, in which a patient is inhaling gas through the ventilator 2. Advantageously, the ventilator 2 is solely mechanical. As used in this document, the term "solely mechanical" is defined to mean a mechanism operable based on gas pressure changes controlled by a patient's breath, without electricity or electronics. According to other embodiments, the ventilator 2 may be controlled, powered, or otherwise operated in whole or in part using electricity and/or electronics. The ventilator 2 includes an ambient fluid aperture 4, which may be generally bell-shaped, or which may have any other suitable shape. The opening of the ambient fluid aperture 4 may have any suitable shape, such as but not limited to circular, oval, rectilinear, or polygonal, and may be bilaterally and/or radially symmetrical, or asymmetrical. The ambient fluid aperture 4 may be located at one end of the ventilator 2. The ventilator 2 also includes a fluid inlet 6, located in proximity to the ambient fluid aperture 4. The fluid inlet 6 may be connected to a source of pressure-controlled fluid, such as oxygen. As seen in FIG. 1, the ambient fluid aperture 4 and the fluid inlet 6 may be arranged generally perpendicular to one another; however, the ambient fluid aperture 4 and the fluid inlet 6 may be arranged relative to one another in any other suitable manner. The fluid inlet 6 may include threads 8 defined on an outer diameter thereof, to facilitate the connection of oxygen or other pressure-controlled fluid to the ventilator 2. Advantageously, the pressure entering the fluid inlet 6 is slightly above ambient. The pressure at the fluid inlet 6 may be adjusted as described in greater detail below. As utilized in the treatment of patients, the fluid inlet 6 may be an oxygen inlet, through which oxygen enters the ventilator 2.

Air from the ambient fluid aperture 4 and oxygen from the fluid inlet 6 are mixed in a venturi 10. According to some embodiments, passages 12 are defined in the ventilator 2 radially outside the ambient fluid aperture 4, and oxygen from the fluid inlet 6 travels from the fluid inlet 6 through the passages 12 to a venturi nozzle 14 and out the venturi opening 16 in the venturi nozzle 14. The specific path, cross-section and other details of the passages 12 are not critical to the invention; rather, as long as a sufficient amount of oxygen is delivered to the venturi opening 16, the passages 12 may be configured in any manner. An air passage 18 allows air to flow from the ambient fluid aperture 4 to the venturi nozzle 14. As oxygen exits the venturi opening 16 of the venturi nozzle 14, that oxygen flow entrains air from the throat 19 of the venturi 10 and mixes with that entrained air, which is oxygen-enriched compared to ambient air. Above the venturi nozzle 14, a central passage 17 extends upwards, allowing oxygen-enriched air to travel to the patient during inhalation, and allowing exhalation air to travel outward from the patient during exhalation. As is well understood in the art, a venturi is typically a short tubular section with a tapering constriction (throat 19) in the middle that causes an increase in the velocity of flow of a fluid passing therethrough. As can be seen from FIGS. 1-2, the venturi opening 16 in the venturi nozzle 14, through which pressure-controlled oxygen (or other pressure-controlled fluid for example) flows outward, opens to said throat 19, and wherein said venturi opening 16 and said throat 19 are substantially longitudinally aligned.

A valve 20 is positioned above the venturi nozzle 14. As used in this document, words of orientation such as "top," "bottom," "above," "below" and the like refer to the orientation of and relative location of parts shown in the Figures relative to the page for ease of description; the ventilator 2 can be used in any orientation, and such words of orientation do not limit use of the ventilator 2. The valve 20 includes a stem 22, which may include a tapered end 24 according to some embodiments. The tapered end 24 may be tapered such that a portion of the tapered end 24 has a diameter less than the diameter of the venturi opening 16 and can enter the venturi nozzle 14 through the venturi opening 16. In the open, inhalation position shown in FIG. 1 the tapered end 24 is spaced apart from the venturi opening 16 such that oxygen can flow out of the venturi opening 16 and entrain ambient air from the air passage 18 in the throat 19 of the venturi 10. According to other embodiments, the stem 22 need not include a tapered end 24, and may instead include an end that grows wider in diameter closer to the venturi nozzle 14, such that the wider end is capable of blocking the venturi opening 16 in a closed position without substantially entering the venturi opening 16. A stem seat 21 may extend laterally toward the stem 22, and may include a stem aperture 23 configured to receive and guide the stem 22 in its longitudinal motion, while substantially restraining the stem 22 against lateral motion. The stem aperture 23 may have a shape similar to and slightly larger than the stem 22. For example, where the stem 22 is generally cylindrical, the outer diameter of the stem 22 may be slightly smaller than the diameter of the stem aperture 23, such that the stem aperture 23 allows the stem 22 to slide relative to the stem aperture 23 while the stem aperture 23 also limits the lateral motion of the stem 22. The valve 20 may be free-floating, as seen in FIGS. 1-2. Optionally, the valve 20 may be biased toward the inhalation configuration shown in FIGS. 1-2, such as by a spring (not shown) or other structure or mechanism. Alternately, the valve 20 may be biased toward the exhalation configuration, such as by a spring (not shown) or other structure or mechanism.

The stem 22 extends from the tapered end 24 to a vent ring 26. The vent ring 26 may be generally cylindrical in shape, including a generally circular bottom 28 and a curved body 30. One or more windows 32 may be defined through the curved body 30. The vent ring 26 may be received by an aperture 34 in a vent ring seat 36. The aperture 34 may have a shape similar to and slightly larger than the vent ring 26. For example, where the vent ring 26 is generally cylindrical, the outer diameter of the vent ring 26 may be slightly smaller than the diameter of the aperture 34, such that the aperture 34 of the vent ring seat 36 allows the vent ring 26 to slide relative to the aperture 34 while the aperture 34 also limits the lateral motion of the vent ring 26. At least one flange 38 may extend radially outward from the vent ring 26. The flange 38 may extend outward from an upper edge of the vent ring 26, or from any other suitable portion of the vent ring 26.

The flange 38 may be connected to a pressure force multiplier 40 within a chamber 42; advantageously, the flange 38 is fixed to the pressure force multiplier 40. According to some embodiments, the pressure force multiplier 40 is a diaphragm 40. The diaphragm 40 extends radially between the vent ring 26 and the inner surface 44 of the chamber 42. The diaphragm 40 is flexible and durable, and may be fabricated from any suitable material such as rubber, latex, plastic or other material or materials. Because the flange 38 is connected to the diaphragm 40, downward motion of the diaphragm 40 causes the flange 38, and thus the valve 20 as a whole, to move downward; upward motion of the diaphragm 40 causes the flange 38, and thus the valve 20 as a whole, to move upward. According to some embodiments, the diaphragm 40 may be biased toward its position in the inhalation configuration. According to other embodiments, the diaphragm 40 may be bistable, such that it is stable both in its position in the inhalation configuration and its position in the exhalation configuration. In this embodiment, the valve 20 is moveable along an axis of movement relative to said venturi opening 16 in said venturi nozzle 14 between a start flow position that causes entrainment of the ambient fluid by the flow of pressure-controlled fluid (for example, pressure-controlled oxygen) within said throat 19, and a stop flow position that ceases entrainment of the ambient fluid by the flow of pressure-controlled fluid within said throat 19. For instance, in an embodiment of the present invention, said pressure force multiplier 40 is configured such that fluid forced into said fluid port 54 actuates said valve 20 along said axis of movement relative to said venturi nozzle 14 to close said venturi nozzle 14; additionally, in an embodiment of the present invention, said pressure force multiplier 40 is configured such that fluid withdrawn from said fluid port 54 actuates said valve 20 along said axis of movement relative to said venturi nozzle 14. The axis of movement of said valve 20, in this embodiment, is substantially longitudinally aligned with a longitudinal direction of said throat 19. In this embodiment, at least a portion of said valve 20 is movable, along said axis of movement, within said throat 19.

Figure 2A:
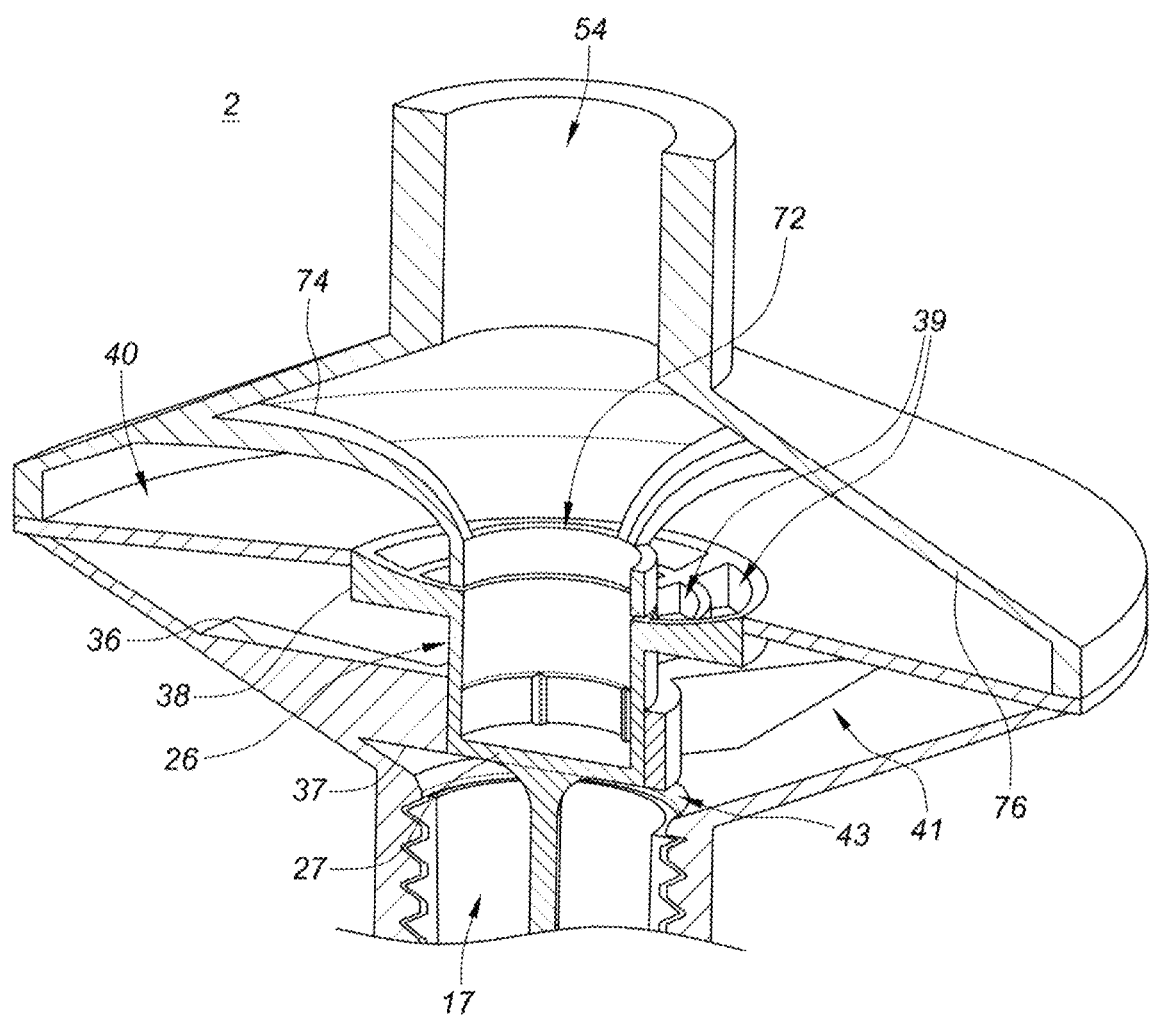
FIG. 2A is a detail perspective cutaway of the ventilator of FIG. 1 in the inhalation configuration, showing a diaphragm in the inhalation configuration.

Referring also to FIG. 2A, in the inhalation configuration, an inlet passage 41 is in fluid communication with the central passage 17. The vent ring 26 is in an upward position relative to the venturi nozzle 14. As a result, the bottom 27 of the vent ring 26 may be substantially even with the lower surface 37 of the vent ring seat 36, and the inlet aperture 43 is thus open, placing the central passage 17 in fluid communication with the inlet passage 41. The flange 38 may be configured as a grid or grate, such as the concentric grid shown in FIG. 2A, such that a plurality of flange openings 39 allow fluid to flow therethrough. In the inhalation configuration, both sides of the diaphragm 40 are thus in fluid communication with one other via the flange openings 39; those flange openings 39 place the inlet passage 41 and the fluid port 54 in fluid communication in the inhalation configuration. Thus, in the inhalation configuration, the central passage 17, the inlet passage 41, and the fluid port 54 are in fluid communication with one another, such that enriched air flows freely from the venturi nozzle 14 to the fluid port 54, and then to the patient.

Where the diaphragm 40 is bistable, the diaphragm 40 may be in one of its two bistable configurations in the inhalation configuration, as seen in FIG. 2A. Utilizing a bistable diaphragm 40 with a stable configuration in the inhalation configuration means the patient need not utilize any breathing force to maintain the inhalation configuration after that inhalation configuration has been reached; as a result, the ventilator 2 may be useful for treating patients with degraded breathing capability. Where the diaphragm 40 is stable in a single configuration, that configuration may be the inhalation configuration as shown in FIG. 2A.

The pressure force multiplier 40 is in fluid communication with said fluid port 54, wherein said pressure force multiplier 40 includes at least one opening 39 defined therethrough; said pressure force multiplier 40 comprising at least one flap 70 movable between an open position and a closed position relative to said at least one opening 39. One or more flaps 70 may be associated with the flange 38, referring also to FIG. 3B. The flaps 70 are described in greater detail below with regard to FIG. 3B. In the inhalation configuration, fluid flow toward the fluid port 54 causes the flaps 70 to be blown upward away from the flange 38 and its (flange) openings 39, allowing for the free flow of enriched air to the patient through the (flange) openings 39. In this embodiment, said pressure force multiplier 40 is positioned between said venturi nozzle 14 and said fluid port 54.

A limiter 72 optionally may be positioned in the chamber 42 above the flange 38. According to some embodiments, the limiter 72 may be a ring having substantially the same diameter as the vent ring 26, where the limiter 72 is substantially coaxial with the vent ring 26. The limiter 72 may be connected to, fixed to, or integral with one or more ribs 74 that extend therefrom. The one or more ribs 74 may extend upward from the limiter 72; alternately, one or more ribs 74 may extend laterally from or downward from the limiter 72. The ribs 74 may be substantially rigid, such that they do not substantially undergo bending or flexure during normal usage of the ventilator 2. According to other embodiments, one or more ribs 74 may be flexible. Each rib 74 is connected at one end to the limiter 72, and at the other end to a portion of the chamber 40. For example, one or more ribs 74 are connected to the upper wall 76 of the chamber 40. The ribs 74 may be fixed to or integral with the upper wall 76 of the chamber 40. For example, the upper wall 76 of the chamber 40, the ribs 74, and the limiter 72 may be injection molded, fabricated by additive manufacturing, or fabricated in any other manner as a single integral piece. The limiter 72 prevents the vent ring 26, and thus the valve 20, from moving upward out of the vent ring seat 36 and/or the stem seat 21.

According to some embodiments, the limiter 72 has another shape than a ring. For example, the limiter 72 may be a bar, a rod, an X-shape, a square, a rectangle, an oval, or any other suitable shape. The limiter 72 may have any shape, and be placed relative to the vent ring 26 in any location, that both engages the vent ring 26 in the inhalation configuration to limit its travel upward to prevent the valve 20 and/or the vent ring 26 from becoming unseated, and allows for substantially unrestricted fluid flow out of the flange openings 39.

At the upper end of the chamber 42, a fluid port 54 allows inhalation air to flow out of the ventilator 2 and exhalation air to flow into the ventilator 2. At least one filter 56 may be positioned adjacent to the fluid port 54, in order to filter both inhalation and exhalation air. The filter 56 advantageously is a 3 micron filter or other filter suitable for removing viruses, pollen and other airborne contaminants from the air. In this way, the filter 56 protects the patient from ambient contaminants, and also protects others near the ventilator 2 from infection from air exhaled from the patient. The filter 56 is detachably connected to the ventilator 2, so that the filter 56 may be periodically replaced. The filter 56 may be a single-use filter, or may be cleanable and sterilizable such that it can be reused after cleaning and sterilization. Alternately, the filter 56 may be placed adjacent to the ambient fluid aperture 4, or at another location on the ventilator 2. For example, according to some embodiments, the filter 56 is positioned adjacent to the ambient fluid aperture 4, in order to filter both inhalation and exhalation air. In this way, the filter 56 protects the patient from ambient contaminants, and also protects others near the ventilator 2 from infection from air exhaled from the patient. Alternately, more than one filter 56 may be utilized.

The chamber 42 may be connected via the fluid port 54 to a respirator (not shown) that is worn by the patient. As typically used in the industry, the term "respirator" refers to a device that provides respirable air to a patient or other user, such as by providing a supply of breathable gas. However, as used in this document, the term "respirator" is specifically defined to exclude any requirement that the respirator itself filter anything from the air provided to the patient, or exhaled by the patient. According to some embodiments, the respirator is substantially impermeable to fluid, whether gas or liquid. According to some embodiments, the respirator may be a mask provided with compliant sealing surfaces or other seal or seals such that a substantially airtight seal is created against the patients face. According to some embodiments, the respirator may be a helmet or other structure that engages a different part of the patient than the face; for example, the respirator may be a helmet that substantially seals against the patient's neck and does not touch the face. According to some embodiments, all of the respirator or a portion of the respirator may be positioned within the patient's nose and/or mouth, and the respirator is substantially sealed relative to the nose and/or mouth. According to some embodiments, such as those described above, the respirator is substantially sealed relative to the patient's airway. By substantially sealing the respirator relative to the patient's airway, slight pressure changes when the patient breathes cause the valve 20 to move, as described in greater detail below. In this way, the respirator and thus the patient are in fluid communication with the ventilator 2. Because the respirator is substantially impermeable to gas, substantially all of the patient's exhalation breath reaches the fluid port 54 of the ventilator 2, such that only a small exhalation effort causes the valve 20 to move. Alternately, the respirator and the patient may be in fluid communication with the ventilator 2 in any other suitable manner.

Figure 3:
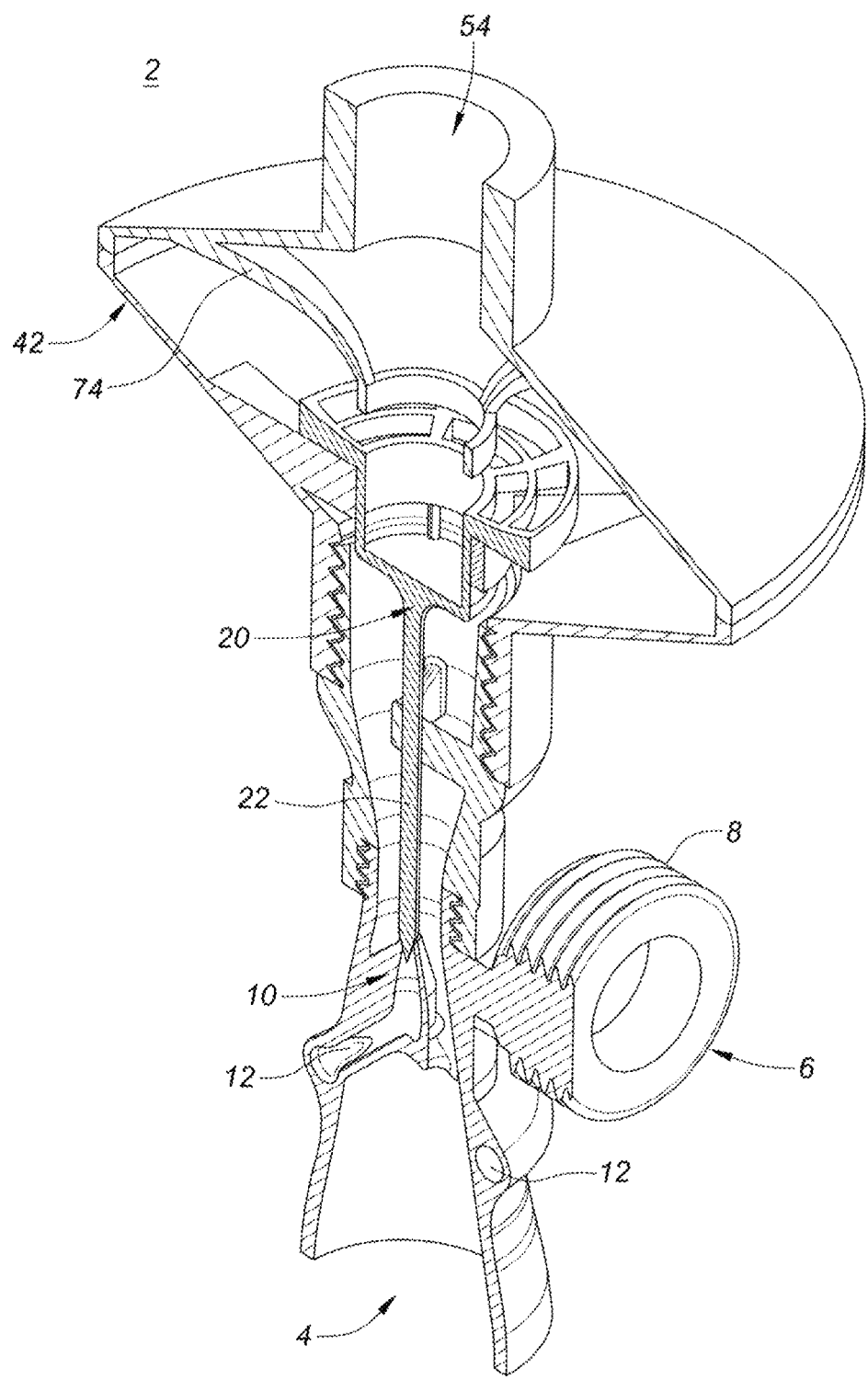
FIG. 3 is a perspective cutaway view of the ventilator in an exhalation configuration.
Figure 4:
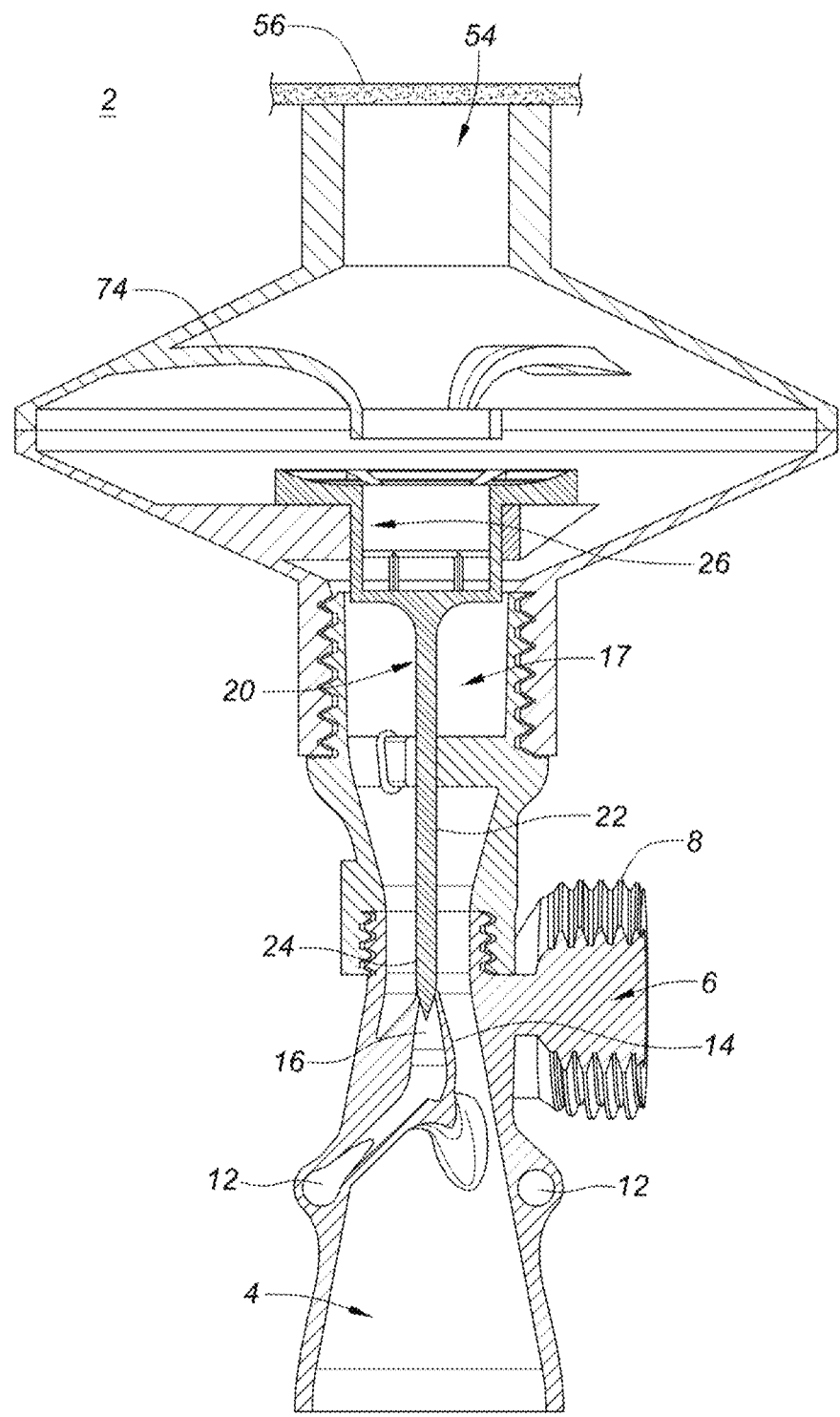
FIG. 4 is a side cutaway view of the ventilator of FIG. 3 in the exhalation configuration.
Figure 5:
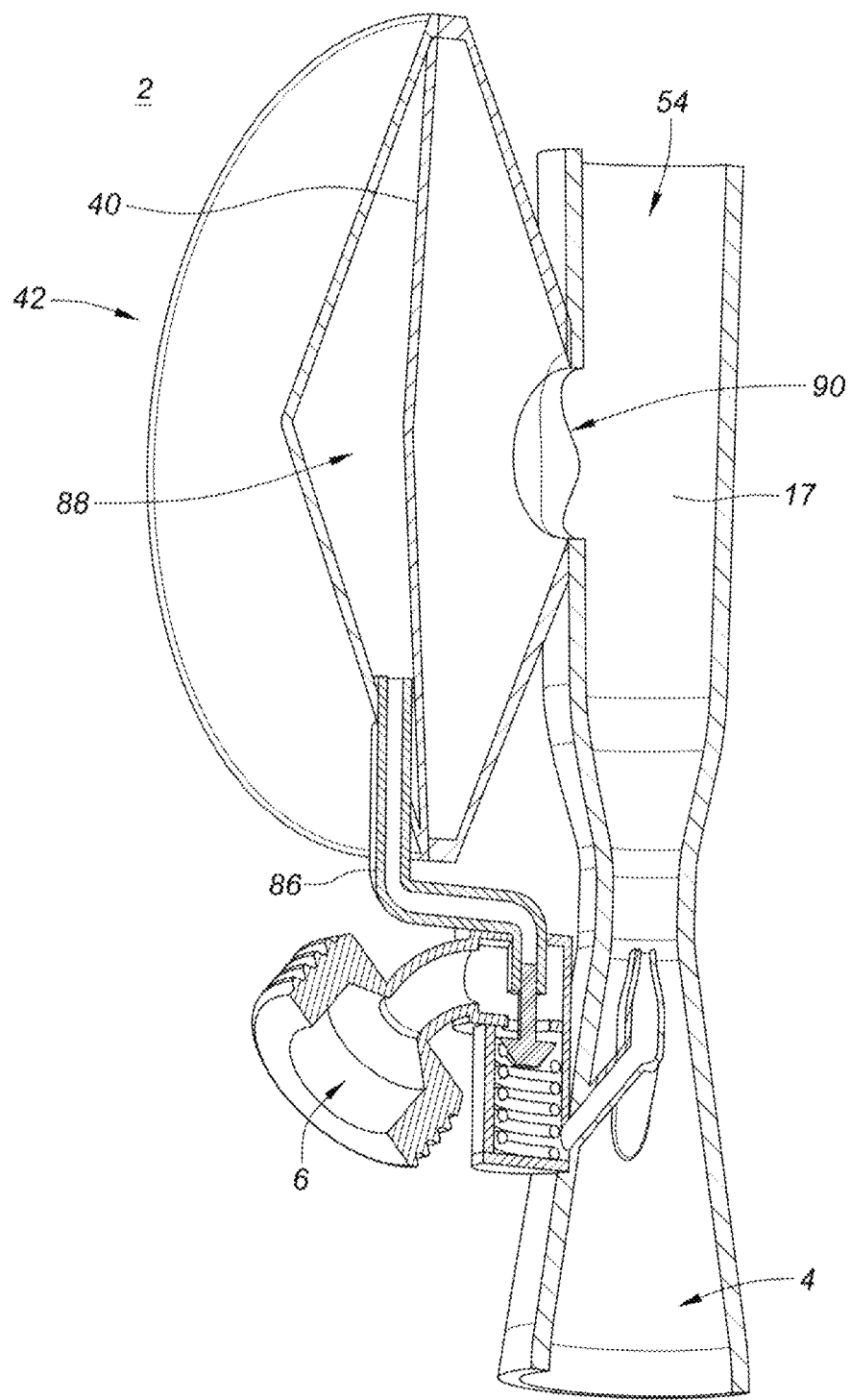
FIG. 5 is a perspective cutaway view of another embodiment of the ventilator.
Figure 6:
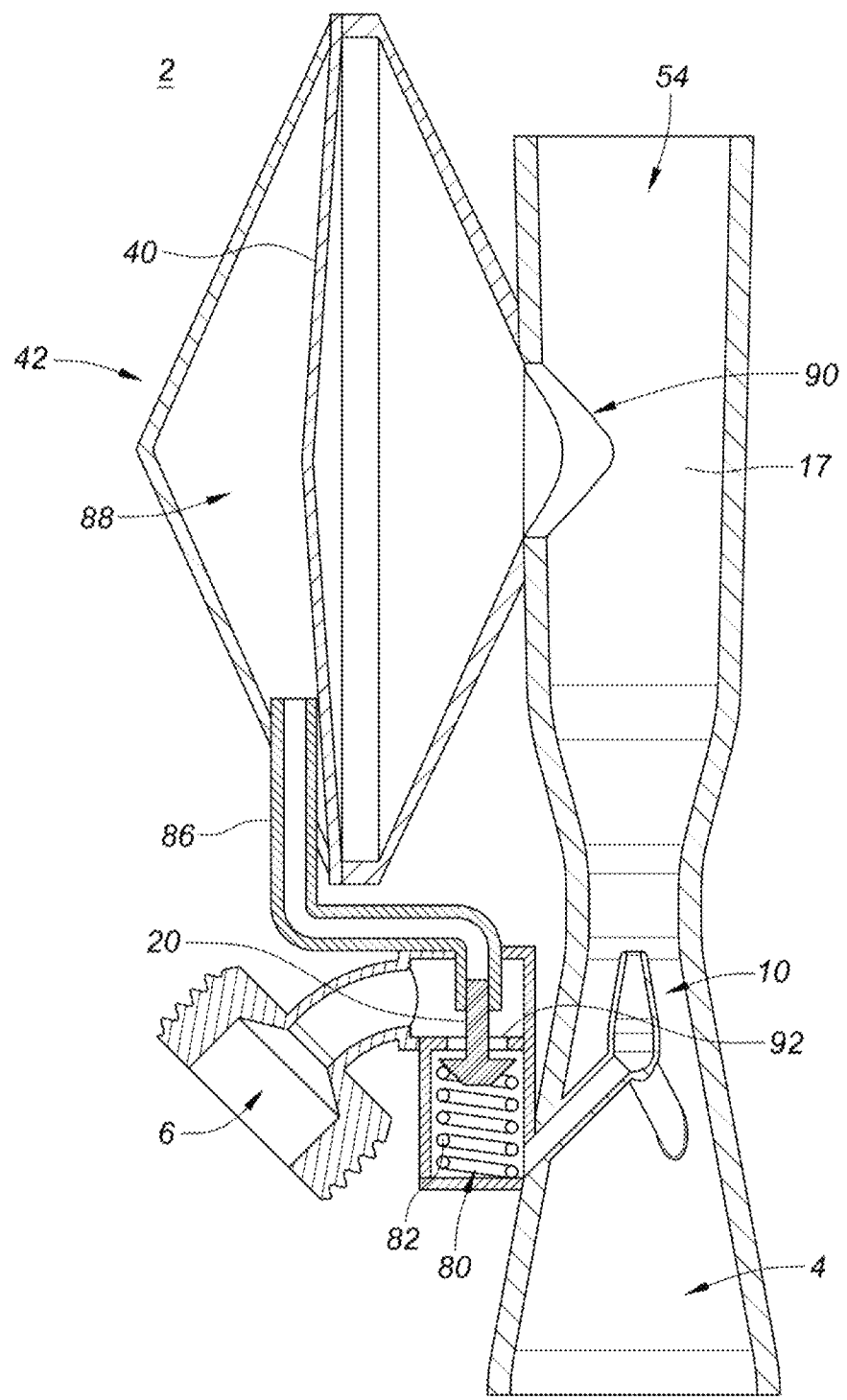
FIG. 6 is a side cutaway view of the ventilator of FIG. 5.
Figure 7:
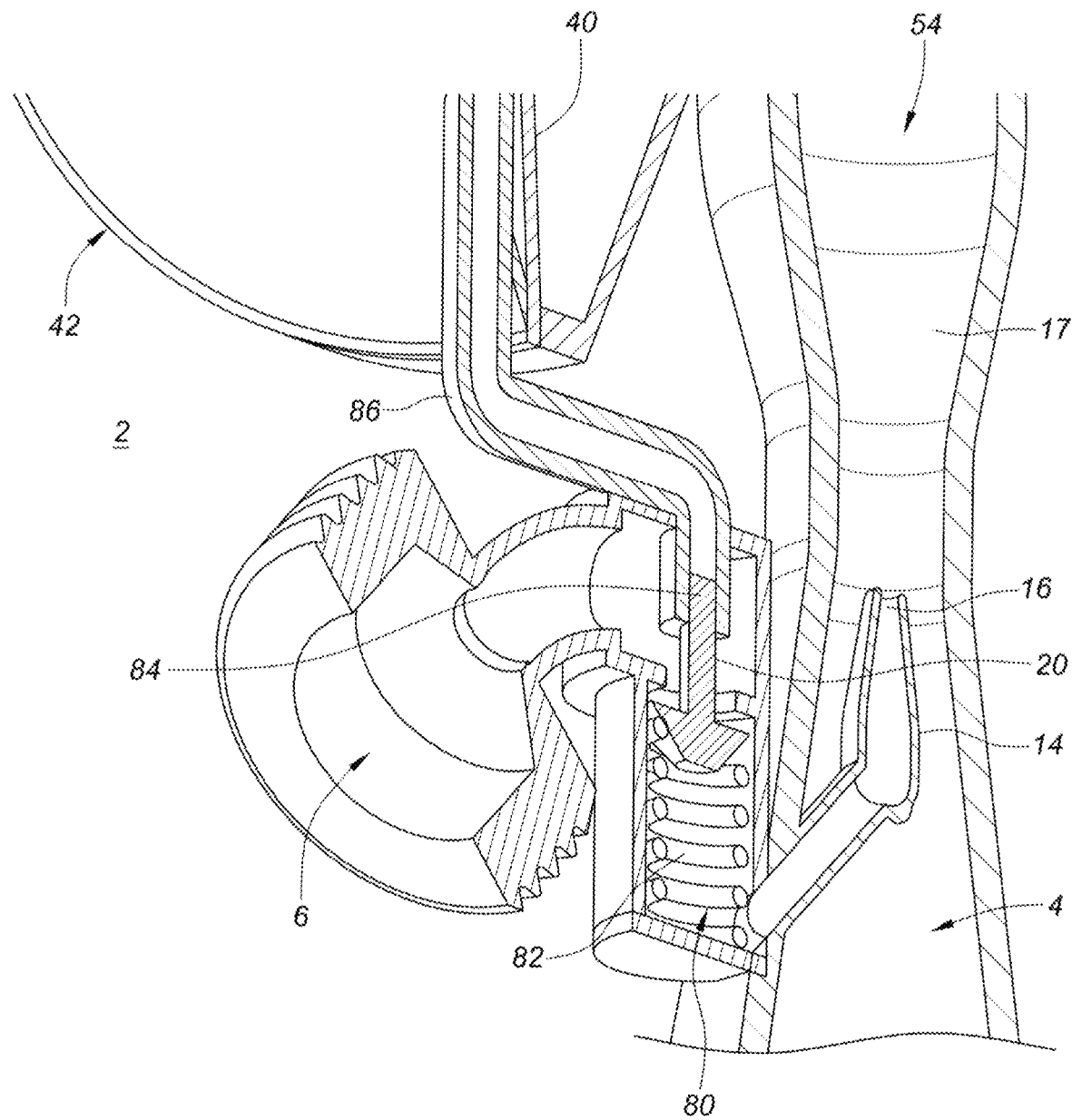
FIG. 7 is a detail perspective cutaway view of a valve of the ventilator of FIG. 5.
Figure 8:
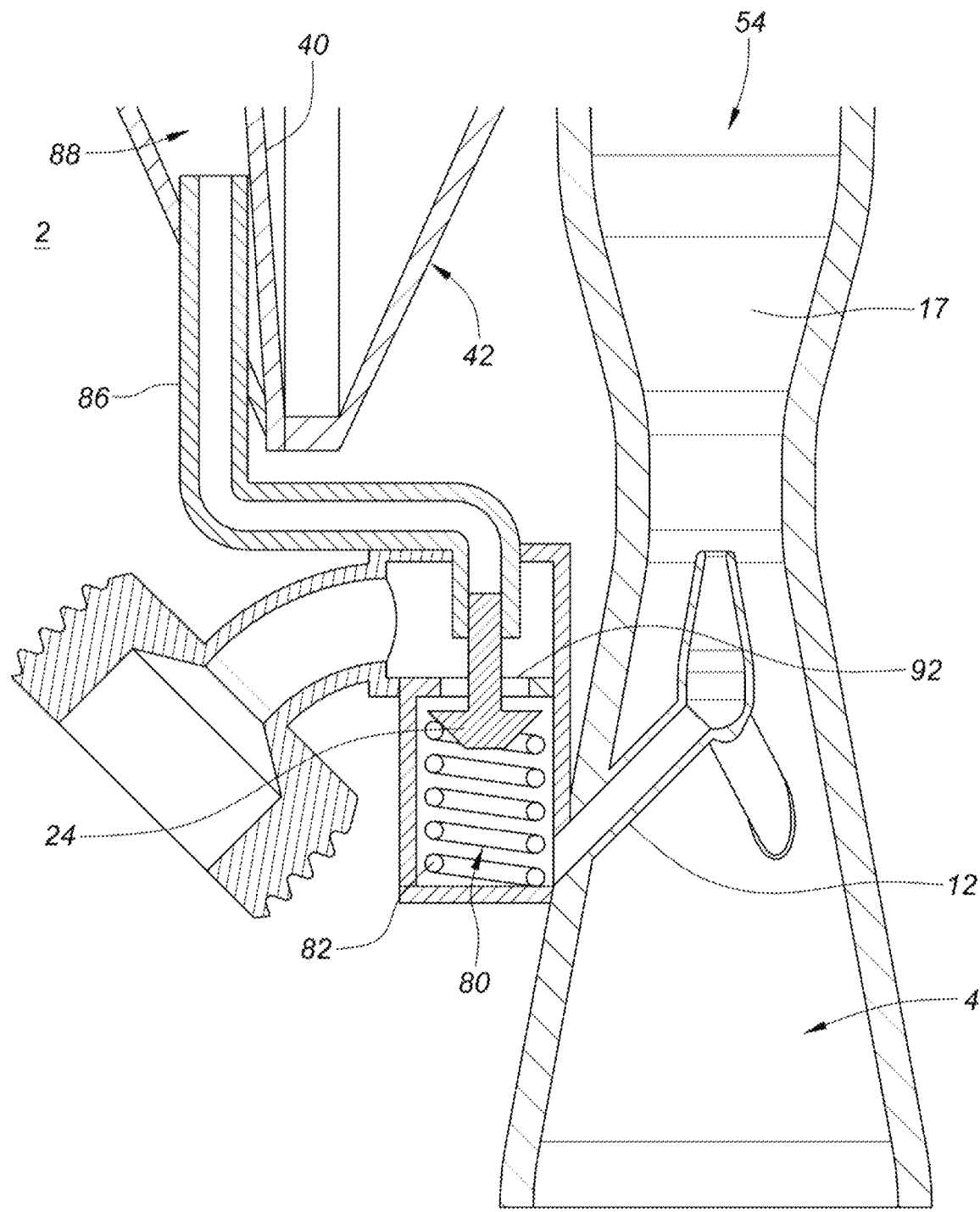
FIG. 8 is detail side cutaway view of a valve of the ventilator of FIG. 5.
Figure 9:
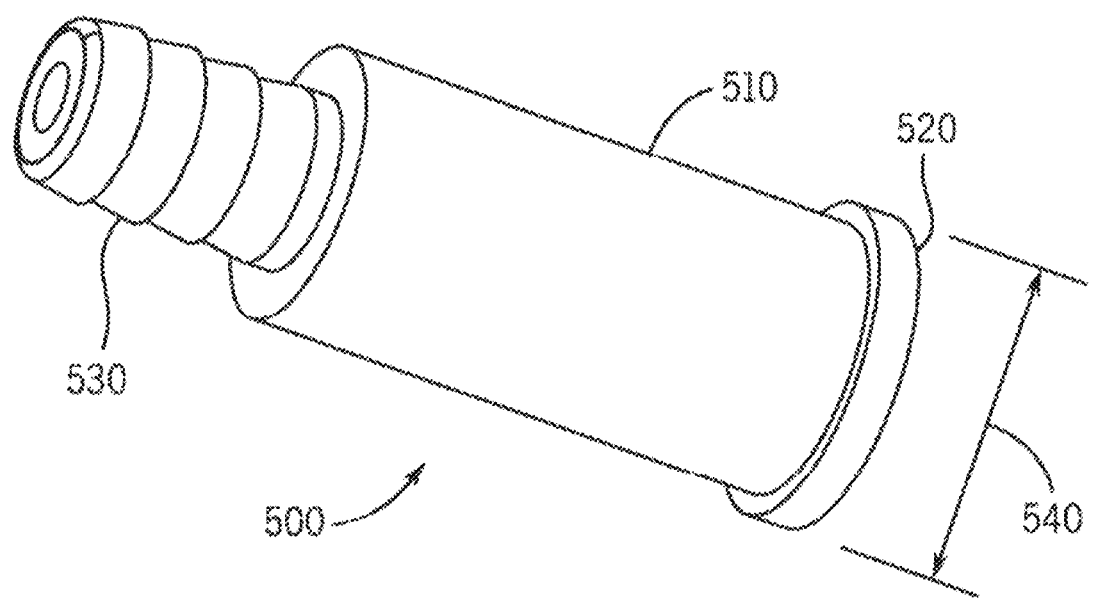
FIG. 9 is a perspective view of one embodiment of a secondary regulator 500.
Figure 10:
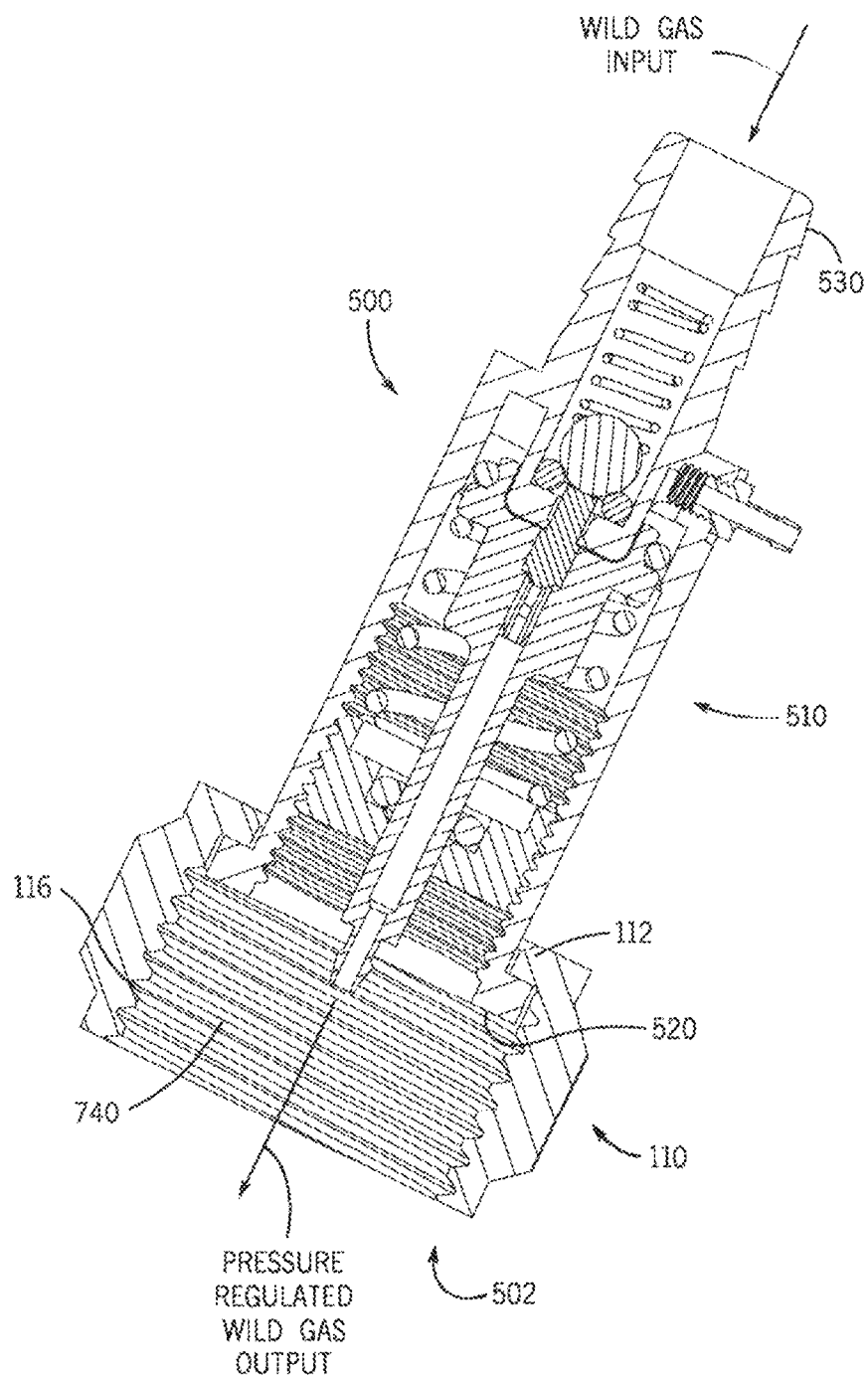
FIG. 10 is a cross-sectional view of the secondary regulator 500.

Referring to FIGS. 3-4, a ventilator 2 is shown in an exhalation configuration, in which a patient is exhaling gas through the ventilator 2. As described in greater detail below, exhalation pressure from the patient flexes the center of the diaphragm 40 downward. As a result, the flange 38, which is connected to the diaphragm 40, moves downward. Downward motion of the flange 38 may be limited by the vent ring seat 36, the upper surface of which may engage a lower surface of the flange 38, thereby preventing further downward motion of the flange 38. In the exhalation configuration, the valve 20 has moved downward relative to the venturi nozzle 14, and the tapered end 24 of the stem 22 substantially blocks the venturi opening 16. In this way, oxygen flow from the fluid inlet 6 outward through the venturi opening 16 is substantially stopped. Advantageously, the length of the stem 22 is fabricated such that the tapered end 24 or other lower end of the stem 22 substantially blocks the venturi opening 16 when the flange 38 engages the vent ring seat 36.

Figure 3A:
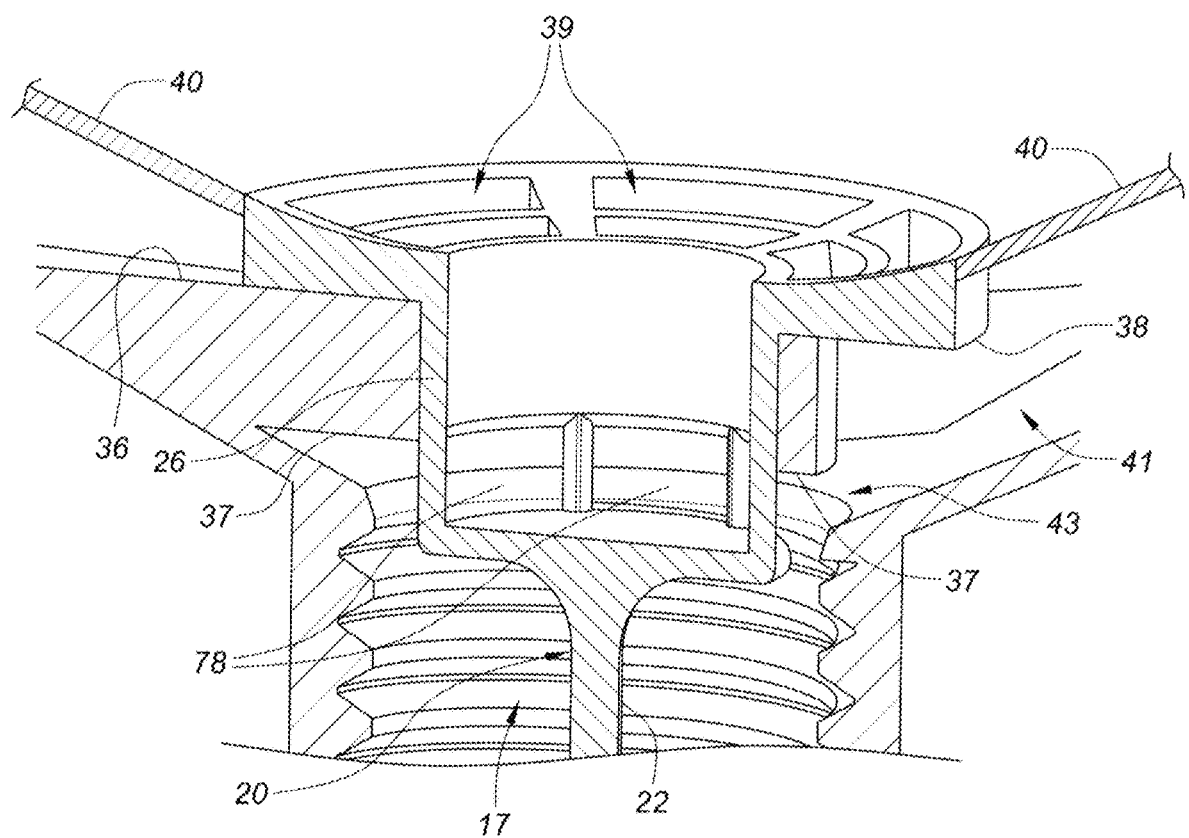
FIG. 3A is a detail perspective cutaway of the ventilator of FIG. 3 in the exhalation configuration, showing exhalation windows.

Referring also to FIG. 3A, in the exhalation configuration, the inlet passage 41 is no longer substantially in fluid communication with the central passage 17. The vent ring 26 is in an downward position relative to the venturi nozzle 14. As a result, the bottom 27 of the vent ring 26 is positioned below the lower surface 37 of the vent ring seat 36, and the inlet aperture 43 is thus closed, substantially closing the central passage 17 in fluid communication with the inlet passage 41. An O-ring or other seal (not shown) may extend radially outward from the vent ring seat 36 to facilitate closure of the inlet aperture 43 in the exhalation configuration. Alternately, the inlet aperture 43 need not be closed, in whole or in part, in the exhalation configuration, because exhalation air will still travel outward through the central passage 17 as described below.

Figure 3B:
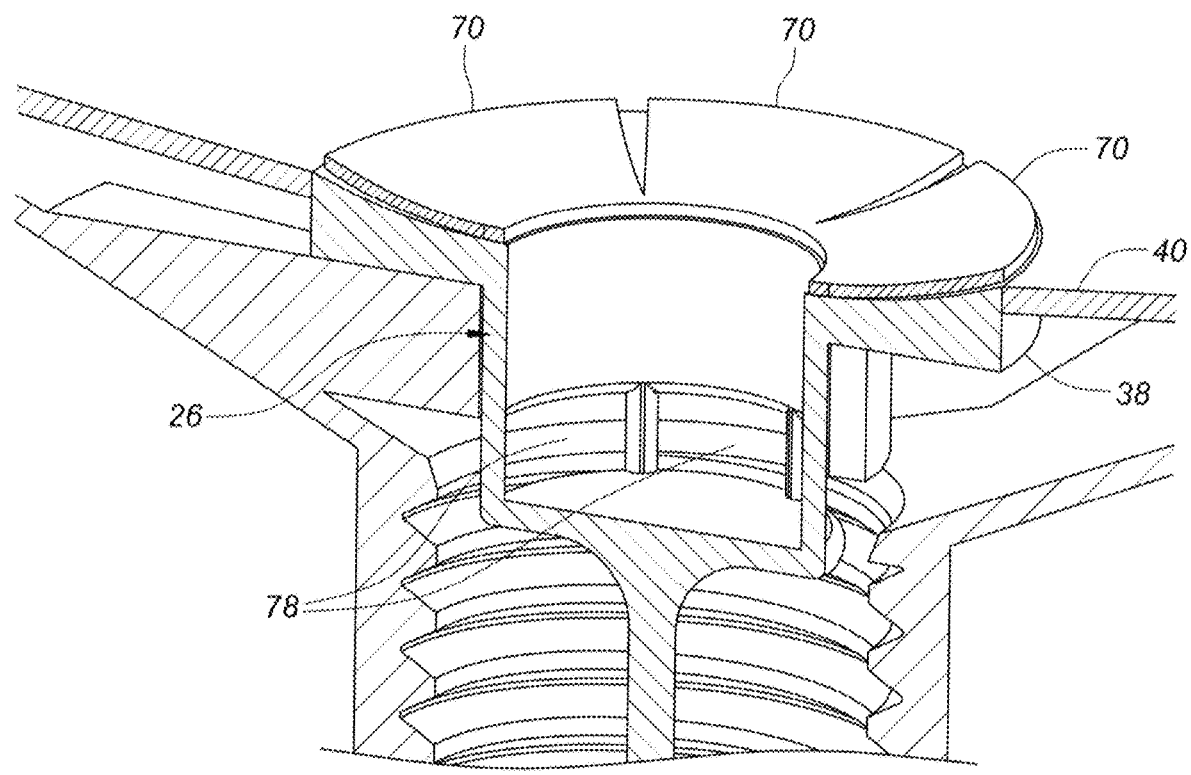
FIG. 3B is a detail perspective cutaway of the ventilator of FIG. 3 in the exhalation configuration, showing flaps.

In the exhalation configuration, the flange 38 has moved downward relative to its position in the inhalation configuration, and may be in contact with the vent ring seat 36. In this way, the vent ring seat 36 may act to limit downward motion of the vent ring 26. Alternately, contact between the tapered end 24 of the stem 22 and the venturi nozzle 14 limits downward motion of the vent ring 26. Where the flange 38 is in the exhalation configuration and the flange 38 contacts the vent ring seat 36, that contact may block at least one of the flange openings 39. Referring also to FIG. 3B, in the exhalation configuration, fluid flow from the fluid port 54 causes the flaps 70 to be pushed down onto the flange 38 and the flange openings 39, substantially stopping the free flow of fluid from the patient through the flange openings 39. In this way, because the flange openings 39 are substantially blocked by the flaps 70, the inlet aperture 43 may remain partly or even entirely open, and exhalation air still cannot substantially flow outward through the flange openings 39 and then outward through the inlet aperture 43. In the exhalation configuration, both sides of the diaphragm 40 may be blocked from fluid communication with one other via the flange openings 39. Thus, in the inhalation configuration, the inlet passage 41 and the fluid port 54 are not substantially in fluid communication with one another. The flaps 70 may be thin and lightweight, and generally impermeable to fluid. For example, the flaps 70 may be composed of latex, rubber, silicone or any other suitable substance.

Because the flange openings 39 are closed, exhalation by the patient into the fluid port 54 causes a pressure rise in the chamber 42 above the diaphragm 40. This rise in pressure pushes the flange 38 downward into contact with or into proximity to the vent ring seat 36, to the exhalation position of the flange 38. Where the diaphragm 40 is bistable, the diaphragm 40 may be in one of its two bistable configurations in the exhalation configuration, as seen in FIG. 3A. Utilizing a bistable diaphragm 40 with a stable configuration in the exhalation configuration means the patient need not utilize any breathing force to maintain the exhalation configuration after that exhalation configuration has been reached; as a result, the ventilator 2 may be useful for treating patients with degraded breathing capability. Where the diaphragm 40 is stable in a single configuration, that configuration may be the exhalation configuration as shown in FIG. 3A.

The vent ring 36 includes one or more exhalation windows 78 defined through the side of the vent ring 36. One or more exhalation windows 78 may be located at or near the bottom 27 of the vent ring 36. As the vent ring 36 moves downward, the exhalation windows 78 move downward, below the lower surface 37 of the vent ring seat 36. The central passage 17 is located below the vent ring seat 36, such that when the exhalation windows 78 move below the lower surface 37 of the vent ring seat 36, exhaled air can flow out of the chamber 42 above the diaphragm 40, through the exhalation windows 78 in the vent ring 26, into the central passage 17, and then out of the ventilator 2 through the ambient fluid aperture 4. Thus, in the exhalation configuration, the fluid port 54 and the central passage are in fluid communication with one another.

Operation

The operation of the ventilator 2 now will be described. The fluid port 54 of the ventilator 2 is placed in fluid communication with a respirator, which is attached to a patient. The respirator is provided with compliant sealing surfaces such that a substantially airtight seal is created against the patients face. The patient inhales from and exhales into the respirator. In turn, the respirator is in fluid communication with the airway of the patient. In this way, the fluid port 54 of the ventilator 2 is placed in fluid communication with the patient's airway. According to other embodiments, the fluid port 54 may be any apparatus other than a respirator that places the fluid port 54 in fluid communication with the patient's airway; the use of the respirator to do so is not critical to the invention.

Upon inhalation by the patient, pressure above the diaphragm 40 is reduced compared to ambient air pressure. As a result, the diaphragm 40 flexes upward at and in proximity to its center. Alternately, the diaphragm 40 may be biased upward, at least in part, independently from the patient's inhalation. The upward motion of the diaphragm 40 moves the flange 38 upward, because the flange 38 is connected to the diaphragm 40. Because the flange 38 is part of or connected to the valve 20, that upward motion of the diaphragm 40 causes the valve 20 to move upward. That upward motion of the valve 20 moves the stem 22 upward, thus moving the tapered end 24 of the step out of the venturi opening 16 and away from the venturi nozzle 14. Because the tapered end 24 of the stem 22 has moved out of the venturi opening 16, oxygen is again free to escape from the venturi opening 16. Thus, in this embodiment, oxygen flow out of the venturi opening 16 restarts purely mechanically, powered by inhalation by the patient via the fluid port 54. Oxygen flows out of the venturi opening 16 as long as the tapered end 24 of the stem 22 is spaced apart from the venturi opening 16. This position of the valve 20, in which the stem 22 is spaced apart from the venturi opening 16 and fluid can flow out of the venturi opening 16, is the start flow position of the valve 20.

Oxygen may be supplied to the fluid inlet 6 from any suitable source. According to some embodiments, high pressure oxygen is connected to a pressure regulator, which drops the pressure of that oxygen and outputs lower pressure oxygen to the fluid inlet 6. In one embodiment, the pressure regulator is the GovReg® adjustable flow regulator of Legacy US, Inc, as described in U.S. patent application Ser. No. 15/488,319, filed Apr. 14, 2017 (the "GovReg® document), which is hereby incorporated by reference in its entirety. That U.S. patent application Ser. No. 15/488,319 is a continuation-in-part of U.S. patent application Ser. No. 14/990,673. The U.S. patent application Ser. No. 15/488,319 application also expressly incorporates by reference therein the U.S. patent application Ser. No. 14/990,673 application in paragraph [0001] of the U.S. patent application Ser. No. 15/488,319 application as originally filed. Thus, the contents of the U.S. patent application Ser. No. 14/990,673 application are incorporated by reference in the present application and specifically FIGS. 5A, 5B, 7A, 7B, 7C, and 7D and the associated text of U.S. patent application Ser. No. 14/990, 673. The use of the GovReg® pressure regulator allows a healthcare worker to set the pressure for a patient and fix that pressure, such that it cannot be changed without the use of an adjustment key that only healthcare workers can change it. This provides additional safety for the patient. Further, multiple ventilators 2 can be connected to the same high pressure oxygen source, and each ventilator 2 can receive a different pressure of oxygen depending on the setting of the GovReg® pressure regulator associated with that ventilator. As described in the "GovReg® document, the pressure regulator may include a housing formed to include a bore within, and a piston movable within that bore, where the piston may include an annular lip adjacent to an end of the piston. A spring may be disposed within the bore, where the spring has two ends, and an adjustment cap may be moveably disposed in the bore, where the adjustment cap may include key slots formed therein. A first end of the spring may be in physical contact with the annular lip, and a second end of the spring may be in physical contact with the adjustment cap. The bore may be defined by a cylindrical wall, and the cylindrical wall may be threaded. The adjustment cap may be threaded as well, such that its threading meshes with the threading of the cylindrical wall. Rotating the adjustment cap in one direction may cause the adjustment cap to compress the spring and increase the output pressure of the pressure regulator, and rotating the adjustment cap in the opposite direction may cause the adjustment cap to decompress the spring and decrease the output pressure of the pressure regulator. The adjustment key may be, or may be detachably connected to, the adjustment cap; the adjustment key may be detachable from the pressure regulator. Thus, in some embodiments, rotation of the adjustment cap allows a healthcare worker to set and fix the pressure for a patient.

Referring now to FIGS. 9-14, a pressure regulator 700 comprises housing 510, piston 760 moveably disposed within housing 510 wherein piston 760 is formed to include an annular lip 762, compression spring 720, and adjustment cap 750. Spring 720 is disposed between annular lip 520 and adjustment cap 750.

Figure 11:
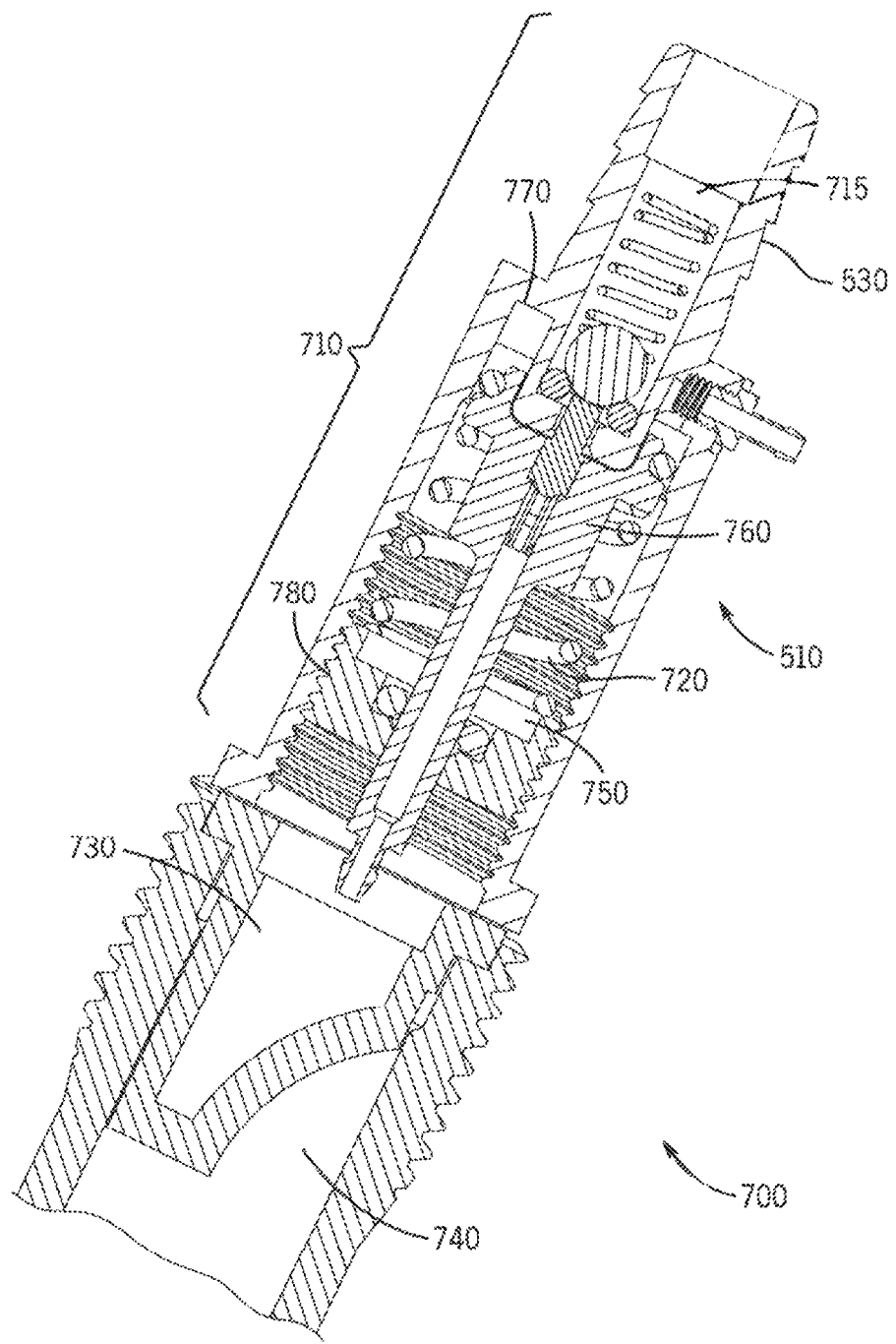
FIG. 11 is a cross-section view of another embodiment of a secondary regulator 700.
Figure 12:
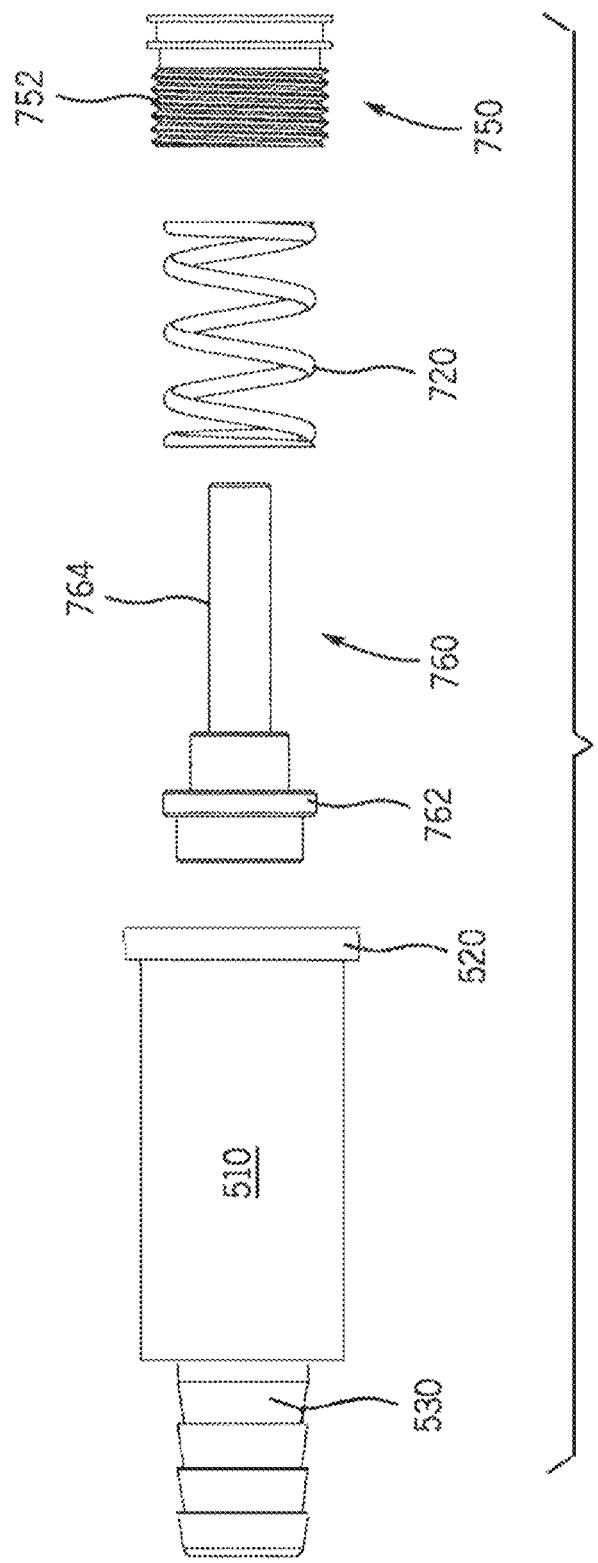
FIG. 12 is an exploded view of the secondary regulator 700.
Figure 13:
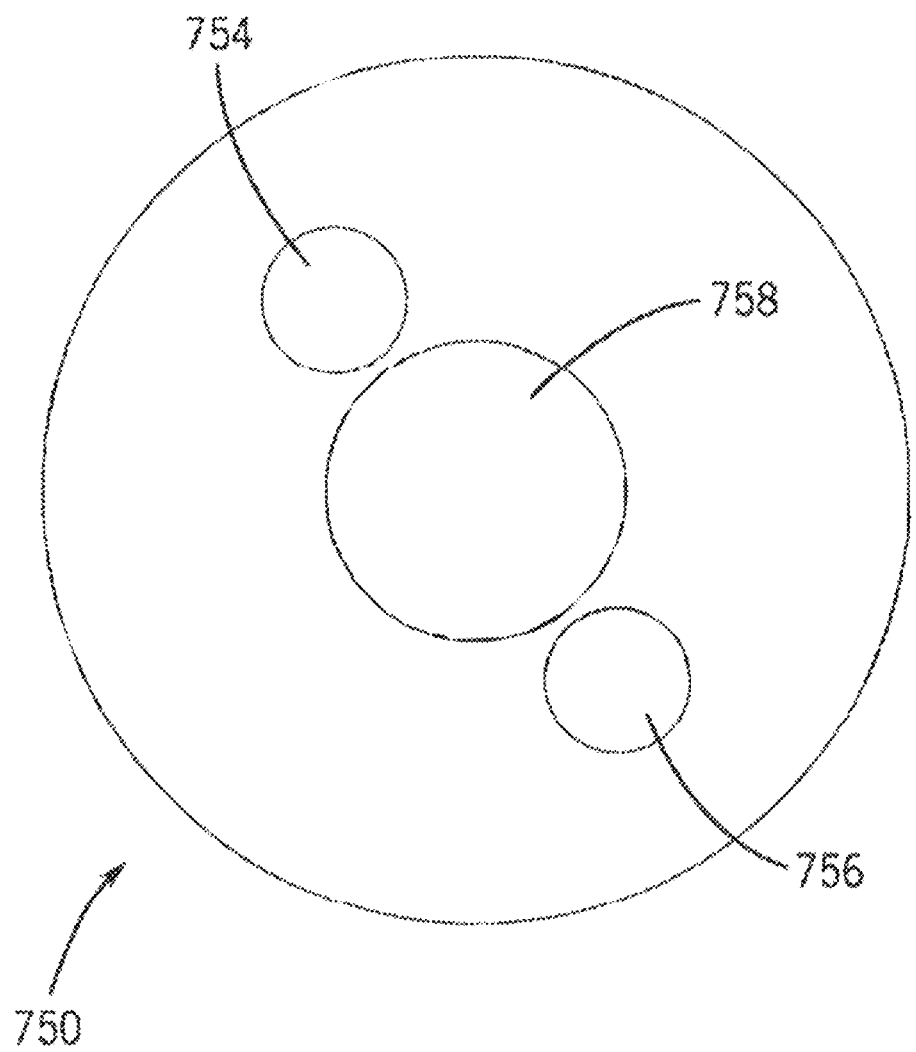
FIG. 13 is a top view of an adjustment cap 750 disposed within the secondary regulator 700.
Figure 14:
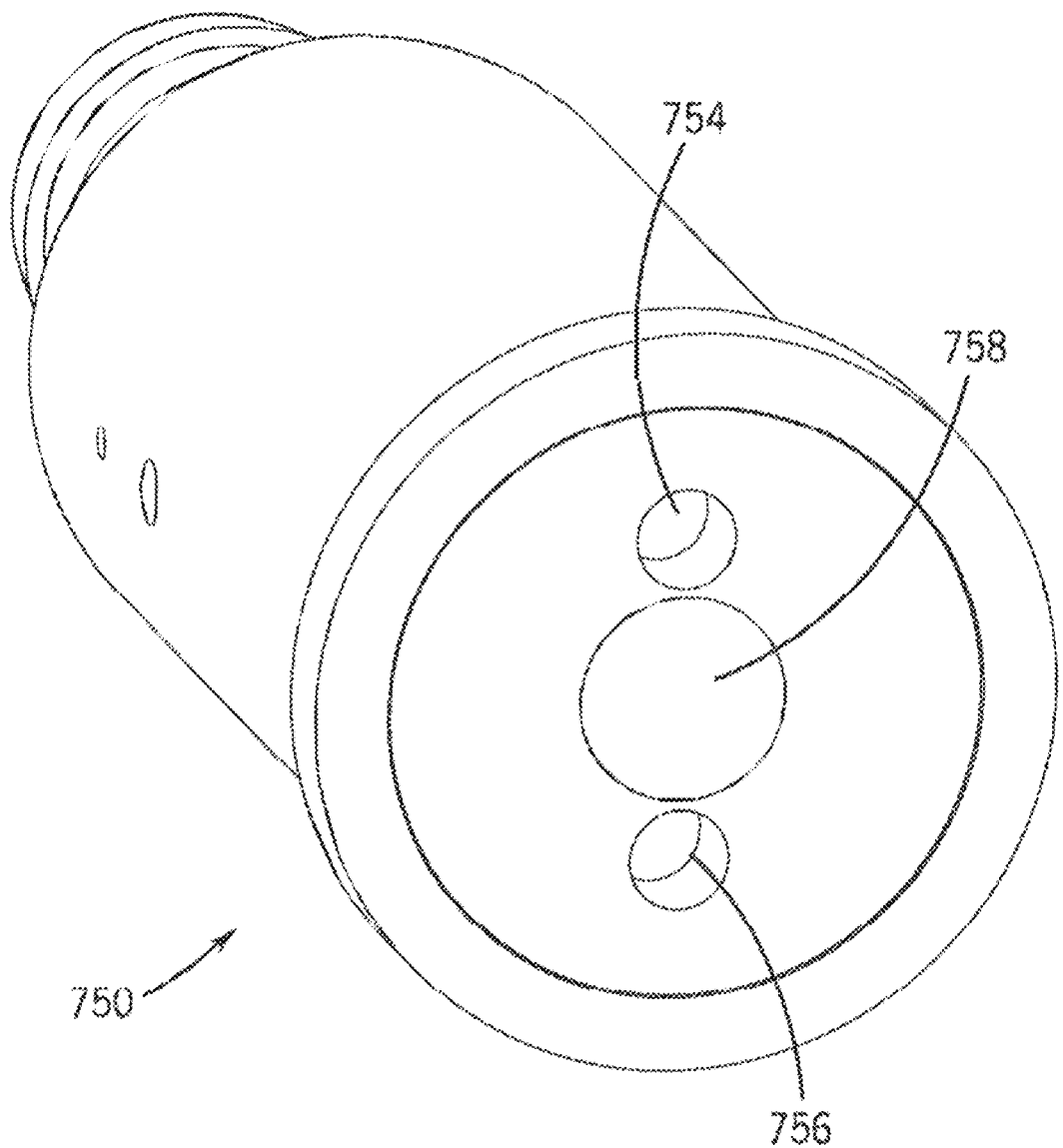
FIG. 14 is a perspective view of the adjustment cap 750.

Referring now to FIGS. 12-14, adjustment cap 750 is formed to include threading adjacent a first end thereof. Threading 752 is configured to mesh with internal threading 780 (FIG. 11).

Compression spring 720 determines the regulated output pressure in portion 740.

Rotating adjustment cap in a first direction compresses spring 720, and increases the output pressure in region 740 (FIG. 11) of regulator 700. Rotating adjustment cap in a second and opposite direction decompresses spring 720, and decreases the output pressure in region 740 (FIG. 11) of regulator 700.

Adjustment cap 750 is further formed to include key slots 754 and 756 which extend inwardly in a second end thereof. Adjustment cap 750 is further formed to include an aperture 758 extending therethrough. Shaft 764 of piston 760 passes through aperture 758.

Oxygen travels through the fluid inlet 6 and then the passages 12, then through the venturi nozzle 14 and out of the venturi opening 16. The flow of oxygen outward through the venturi opening 16 entrains ambient air entering the ventilator 2 through the ambient fluid aperture 4, and draws ambient air into the throat 19 of the venturi 10, where oxygen and ambient air are mixed. The venturi nozzle 14 may be sized and configured to create a mixture of ambient air and oxygen that delivers a 26% fraction of inspired oxygen ($FiO_2$) to the patient. This percentage of $FiO_2$ is a recommended oxygen concentration, but other fractions may be used as needed. Accuracy of the fraction of oxygen is not critical, and that fraction may be adjusted by a clinician or other healthcare worker as required. For example, the $FiO_2$ may be adjusted to 40% from 26% as needed by the patient; after the $FiO_2$ has been adjusted to 40%, if the patient needs additional oxygen, the patient may then be removed from the ventilator 2, intubated, and then placed on a currently-known ventilator.

The enriched air travels upward through the central passage 17 to the inlet aperture 43. In the inhalation configuration, the inlet passage 41 is in fluid communication with the central passage 17. As described above, in the inhalation configuration, the vent ring 26 is in an upward position relative to the venturi nozzle 14. In the inhalation configuration, the lowered pressure in the chamber 42 above the diaphragm 40, caused by inhalation by the patient through the fluid port 54, causes the diaphragm 40 to move upward. Inhalation withdraws gas from the chamber 42 above the diaphragm 40, decreasing the pressure and actuating the valve 20 relative to the venturi nozzle 14. The flange 38 may contact the limiter 72, such that the flange 38 does not move higher than the limiter 72 allows. Upward motion of the diaphragm 40 causes the flange 38, which is attached to the flange 38, to move upward. Upward motion of the flange 38 causes the valve 20, of which the flange 38 is a part, to move upward as well. Such upward motion of the valve 20 moves the stem 22 away from the venturi nozzle 14, thereby unblocking the venturi opening 16 and allowing gas to flow outward therefrom. The diaphragm 40 is an example of a pressure force multiplier 40, because the surface area of the diaphragm 40 in combination with the flange openings 39 allow for a small differential change in pressure at the fluid port 54 to actuate the valve 20 between closed and open states.

As described above, in the inhalation configuration, the inlet aperture 43 is open, placing the central passage 17 in fluid communication with the inlet passage 41, and both sides of the diaphragm 40 are thus in fluid communication with one other via the flange openings 39; as a result, those flange openings 39 place the inlet passage 41 and the fluid port 54 in fluid communication in the inhalation configuration. Thus, in the inhalation configuration, the central passage 17, the inlet passage 41, and the fluid port 54 are in fluid communication with one another, such that enriched air flows freely from the venturi nozzle 14 to the fluid port 54, and then to the patient.

The patient inhales normally, or as normally as possible. The ventilator 2 is a simple, single-mode ventilator that does not deliver a specific, limited or preselected volume or flow rate of air to the patient; instead, it delivers air at a volume and flow rate that are controlled solely by the patient's own inhalation. Further, the ventilator 2 only delivers enriched air to the patient during the patient's inhalation, and momentarily afterward. As opposed to continuous positive airway pressure (CPAP) or positive end-expiratory pressure (PEEP) ventilation, enriched air is only supplied to the patient during inhalation. In this way, the ventilator 2 does not apply pressure to the patient's nose or mouth while the patient is trying to exhale, and oxygen is not wasted by applying it to the patient's nose or mouth while the patient is actively exhaling.

After inhalation, the patient then exhales. Upon exhalation by the patient, pressure above the diaphragm 40 is increased compared to ambient air pressure. Referring also to FIG. 3B, in the exhalation configuration, fluid flow into the chamber 42 from the fluid port 54 causes the flaps 70 to be pushed down onto the flange 38 and the flange openings 39, substantially stopping the free flow of fluid from the patient through the flange openings 39. In this way, because the flange openings 39 are substantially blocked by the flaps 70, the inlet aperture 43 may remain partly or even entirely open, and exhalation air still cannot substantially flow outward through the flange openings 39 and then outward through the inlet aperture 43. In the exhalation configuration, both sides of the diaphragm 40 may be blocked from fluid communication with one other via the flange openings 39. Thus, in the exhalation configuration, the inlet passage 41 and the fluid port 54 are not substantially in fluid communication with one another.

Because the flange openings 39 are closed, exhalation by the patient into the fluid port 54 causes a pressure rise in the chamber 42 above the diaphragm 40. That is, exhalation forces gas into the chamber 42 above the diaphragm 40, increasing the pressure and actuating the valve 20 relative to the venturi nozzle 14. This rise in pressure pushes the flange 38 downward into contact with or into proximity to the vent ring seat 36, to the exhalation position of the flange 38. Because the flange 38 is part of or connected to the valve 20, that downward motion of the diaphragm 40 causes the valve 20 to move downward. That downward motion of the valve 20 moves the stem 22 downward, thus moving the tapered end 24 of the step toward from the venturi nozzle 14 and into the venturi opening 16. Because the tapered end 24 of the stem 22 has moved into the venturi opening 16, oxygen is substantially restricted from escaping from the venturi opening 16. Thus, oxygen flow out of the venturi opening 16 stops purely mechanically, powered by exhalation by the patient through the fluid port 54. Oxygen is substantially restricted from escaping out of the venturi opening 16 as long as the tapered end 24 of the stem 22 plugs the venturi opening 16. This position of the valve 20, in which the stem 22 plugs the venturi opening 16 and fluid is substantially restricted from flowing out of the venturi opening 16, is the stop flow position of the valve 20.

As the flange 38 and the vent ring 36 moves downward, the exhalation windows 78 move downward, below the lower surface 37 of the vent ring seat 36. The central passage 17 is located below the vent ring seat 36, such that when the exhalation windows 78 move below the lower surface 37 of the vent ring seat 36, exhaled air can flow out of the chamber 42 above the diaphragm 40, through the exhalation windows 78 in the vent ring 26, into the central passage 17, and then out of the ventilator 2 through the ambient fluid aperture 4. Thus, in the exhalation configuration, the fluid port 54 and the central passage are in fluid communication with one another. The exhaled breath then travels through the central passage 17 and out of the ventilator 2 through the ambient fluid aperture 4. When the patient then inhales again, the cycle of operation described above repeats again.

Because the ventilator 2 does not require electrical power to operate according to some embodiments, its form factor may be comparatively small, such that the ventilator 2 may be portable. The ventilator 2 may be carried on the user's back by a strap or straps like a backpack; may be carried by a strap over the shoulder like a purse, may be wheeled and able to be pulled behind a user like luggage, or may be otherwise portable. The portability of the ventilator 2 also allows the user to take the ventilator 2 home. Home use of the ventilator 2 may be advantageous for patients who have been diagnosed with COVID-19 or other respiratory disease, but whose symptoms have not advanced to the level of seriousness of ARDS such that they require intubated ventilation. In this way, during a pandemic such as the 2020 COVID-19 pandemic, patients who are infected with a virus that causes respiratory problems can be treated safely at home, without consuming hospital beds and other hospital resources needed for patients who are significantly sicker and closer to death.

Because the ventilator 2 is small and portable and noninvasive, and simply provides enriched air with a higher oxygen concentration to a user, the ventilator 2 may find use in other applications. As one example, the ventilator 2 may be useful in the treatment of asthma and/or seasonal allergies. The user wears a respirator as described above, and the ventilator 2 works substantially as described above; a user utilizes it as a portable device. The increased oxygen concentration delivered by the ventilator 2 may be beneficial for asthma sufferers, and the filter(s) 56 may be useful for removing pollen and other allergens from the air before they can be inhaled by the user, thereby improving symptoms experienced by those who suffer from seasonal allergies. As another example, in extremely polluted cities, the air may be unhealthy to breathe. By utilizing the ventilator 2 as a portable device, clean oxygen is delivered to the user at a higher than ambient concentration, and the filter(s) 56 may be useful for removing particulates and/or other pollutants from the ambient air prior to inhalation by the user.

The ventilator 2 described above with regard to FIGS. 1-4 may find particular use in the treatment of patients infected with the COVID-19 virus, especially prior to their development of ARDS. It is believed that treatment of such patients utilizing the ventilator 2 may prevent a portion of such patients from developing ARDS. It is expected that the ventilator 2 would be classified as a Class II medical device by the FDA and would thus require approval by the FDA for use in treating patients. While the regulatory path for approval by the FDA of the ventilator 2 is unknown as of the filing date of this document, it is expected that for use as a medical device, the ventilator 2 would require at least one of an Investigational Device Exemption (IDE), an Emergency Use Authorization (EUA), and a Premarket Approval (PMA). The independent claims as filed are believed to cover embodiments of the ventilator 2 that would be subject to an applicable FDA approval.

However, the ventilator 2 is not limited to use the treatment of patients infected with the COVID-19 virus; the ventilator 2 may be used to treat patients suffering from other ailments. Further, the ventilator 2 may find use in fields other than healthcare in which control of fluid flow is desired, and need not be used in conjunction with a human being in such fields. Further, the ventilator 2 is described above as having components in fluid communication with one another and with one or more external attachments, such as a respirator. Where the ventilator 2 is utilized to treat a patient, the fluid of that fluid communication is a gas. However, where the ventilator 2 is utilized in other applications, the fluid may be a liquid, or a mixture of liquid and gas.

While the embodiment of the invention described above arose in an endeavor to facilitate treatment of respiratory conditions associated with COVID-19, it will be understood that the fluid mixer 2 has various other uses and applications in other fields, which include but are not limited to the following. As one example, in Formula 1 racing and other racing applications, the fluid mixer 2 may be used to pre-spin turbochargers by detecting pressure changes, to actuate cam timing changes based on pressure, to actuate opening of fuel/air and exhaust ports based on pressure, to actuate aerodynamic downforce adjustment based on pressure conditions at a sample site, to actuate fuel system pressure adjustment, and to regulate temperature in fluid. As another example, in standard automotive usage, the fluid mixer 2 may be used to actuate turbocharger pre-spin, to actuate cam timing changes, to actuate opening of fuel/air and exhaust ports based on pressure, to actuate fuel system pressure adjustment, and to regulate temperature in fluid As another example, in indoor agriculture applications, the fluid mixer 2 may be used to actuate gas mixing based on pressure, and/or to actuate a pressure communication system. In such applications, the fluid that flows through the fluid mixer 2 may be a liquid, a gas, or both.

Referring also to FIGS. 5-8, another embodiment of the fluid mixer 2 is shown. Such an embodiment may be described as a "reverse configuration." Such an embodiment may be useful for automotive or racing applications, although the fluid mixer 2 of FIGS. 5-8 is not limited to use in such applications. Any embodiment may be used with liquid, gas or both as the fluid. As seen in FIGS. 5-8, the valve 20 is in a start flow position, in which fluid can enter the fluid mixer 2 through the fluid inlet 6. The valve 20 may include a tapered end 24 or other suitably-shaped end, which is received in a bore 80. A spring 82 may be received in the bore 80 as well. One end of the spring 82 may engage an end of the bore 80, and the other end of the spring 82 may engage an end of the valve 20. The other end 84 of the valve 20 may be substantially cylindrical, or have any other suitable shape. The end 84 of the valve 20 is received in a pipe 86 through which fluid can flow. The bore 80 is substantially hollow, such that fluid flows from the fluid inlet 6 through the bore 80 when the valve 20 is in the start flow position, and then into one or more passages 12. As described in the with regard to the previous embodiment, fluid flows out of the one or more passages 12 through the venturi opening 16 in the venturi nozzle 14.

In this embodiment, the pressure force multiplier 40 is substantially sealed to the chamber 42 to form a sealed plenum 88. Unlike the previous embodiment, fluid does not substantially cross the pressure force multiplier 40. When fluid flows into the fluid mixer 2 through the fluid port 54, that fluid flows toward the ambient fluid aperture 4 through the central passage 17. The chamber 42 is open to the central passage 17 through a chamber opening 90. The chamber opening 90 may have any suitable shape and size. The chamber opening 90 allows for fluid communication between the chamber 42 and the central passage 17. When fluid is forced into the central passage 17 through the fluid port 54, pressure in the central passage 17 increases. Pressure in the chamber 42 on the side of the pressure force multiplier 40 opposite the plenum 88 increases as well due to fluid communication through the chamber opening 90. Because the pressure force multiplier 40 is substantially sealed to the chamber 42 and fluid substantially cannot cross the pressure force multiplier 40, pressure on the pressure force multiplier 40 increases, causing the pressure force multiplier 40 to move and thus decrease the volume of the plenum 88, increasing the pressure in the plenum 88 as well. That increased pressure in the plenum 88 is transmitted through the pipe 86 to the end 84 of the valve 20. That pressure drives the end 84 of the valve 20 toward the spring 82 in the bore 80, opening the valve 20 to the start flow position. In the start flow position, the tapered end 24 of the valve 20, or otherwise-shaped end of the valve 20, moves apart from the aperture 92, allowing fluid to flow through the aperture 92 into the bore 80. It may be that the volume of the plenum 88, along with the volume of the pipe 86, remains substantially constant during this process. This is because the end 84 of the valve 20 in the bore 80 is movable, such that any momentary increase in pressure in and decrease in volume of the plenum 88 may be substantially matched by movement of the end 84 of the valve 20. In this way, a substantially fixed volume may be defined on one side of the pressure force multiplier 40.

When fluid flows into the fluid mixer 2 through the ambient fluid aperture 4, that fluid flows toward the fluid port 54 through the central passage 17. When fluid is withdrawn through the fluid port 54, pressure in the central passage 17 decreases. Pressure in the chamber 42 on the side of the pressure force multiplier 40 opposite the plenum 88 decreases as well due to fluid communication through the chamber opening 90. Because the pressure force multiplier 40 is substantially sealed to the chamber 42 and fluid substantially cannot cross the pressure force multiplier 40, pressure on the pressure force multiplier 40 decreases, causing the pressure force multiplier 40 to move and thus increase the volume of the plenum 88, decreasing the pressure in the plenum 88 as well. That decreased pressure in the plenum 88 is transmitted through the pipe 86 to the end 84 of the valve 20. The pressure applied to the end 84 of the valve 20 in the bore 80 decreases, allowing the spring 82 to push the end 84 of the valve 20 further into the pipe 86. The spring 82 may be a compression spring that biases the valve 20 toward the stop flow positions; motion of the valve 20 toward the pipe 86 closes the valve 20 to the stop flow position. In the stop flow position, the tapered end 24 of the valve 20, or otherwise-shaped end of the valve 20, moves toward and substantially blocks the aperture 92, substantially stopping fluid flow through the aperture 92 into the bore 80. According to some embodiments, the start flow position of the valve 20 is also the active flow position, allowing fluid to flow while the valve is in the start flow position. Alternately, the valve 20 may be positioned in a different active flow position, between the start flow and stop flow positions; such an active flow position may be determined by the level or duration of force with which fluid is forced into the fluid port 54 or withdrawn from the fluid port 54.

Figure 15:
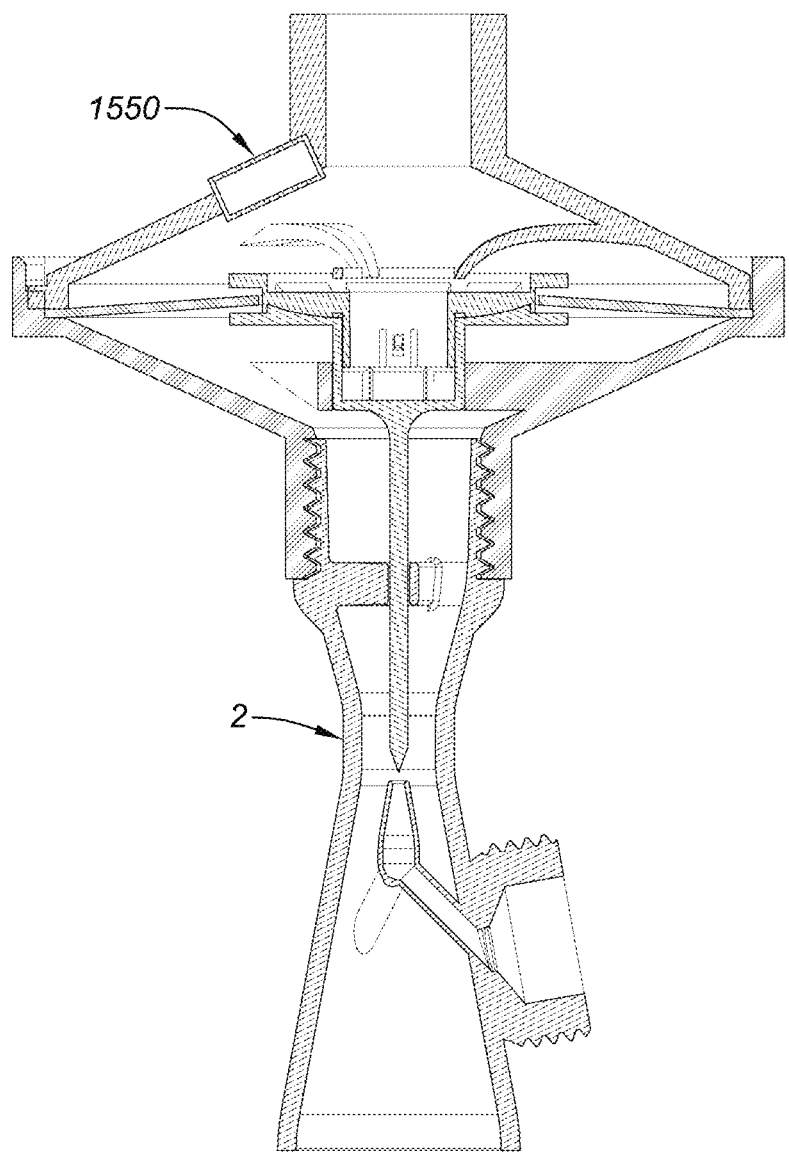
FIG. 15 is a side cutaway view of the ventilator/apparatus according to an embodiment of the invention having a sensor in one position.

Referring now to FIG. 15, there is shown a side cutaway view of the ventilator/apparatus 2 according to an embodiment of the invention. The ventilator/apparatus 2 is that described herein, but having a sensor module 1550 positioned between the pressure force multiplier and the fluid port. The sensor module 1550 may comprise any of the sensors described herein, for instance, pressure sensor, oxygen sensor, carbon dioxide sensor, temperature sensor, humidity sensor et al. The sensor module 1550 also, in this embodiment, comprises a central processing unit.

Figure 16:
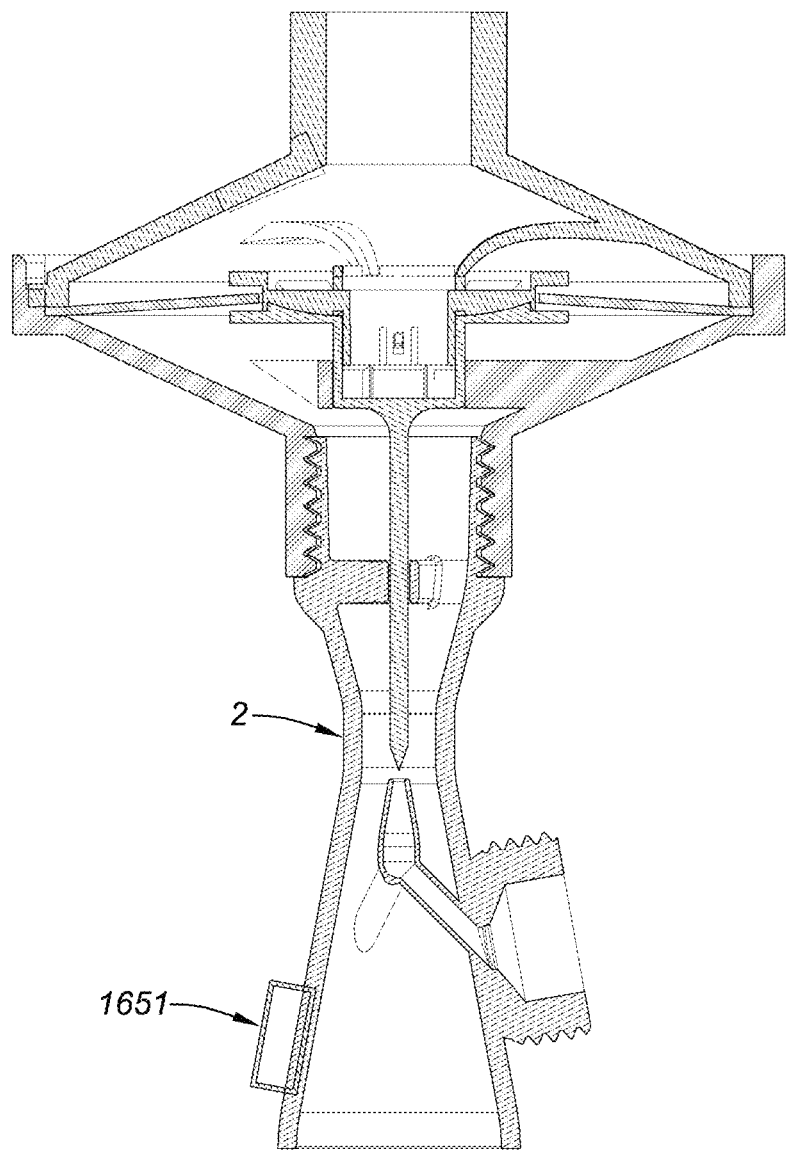
FIG. 16 is a side cutaway view of the ventilator/apparatus according to an embodiment of the invention having a sensor in another position.

Referring now to FIG. 16, there is shown a side cutaway view of the ventilator/apparatus 2 according to an embodiment of the invention. The ventilator/apparatus 2 is that described herein, but having a sensor module 1551 positioned between the venturi nozzle and the ambient air aperture. The sensor module 1551 may comprise any of the sensors described herein, for instance, pressure sensor, oxygen sensor, carbon dioxide sensor, temperature sensor, humidity sensor et al.

Figure 17:
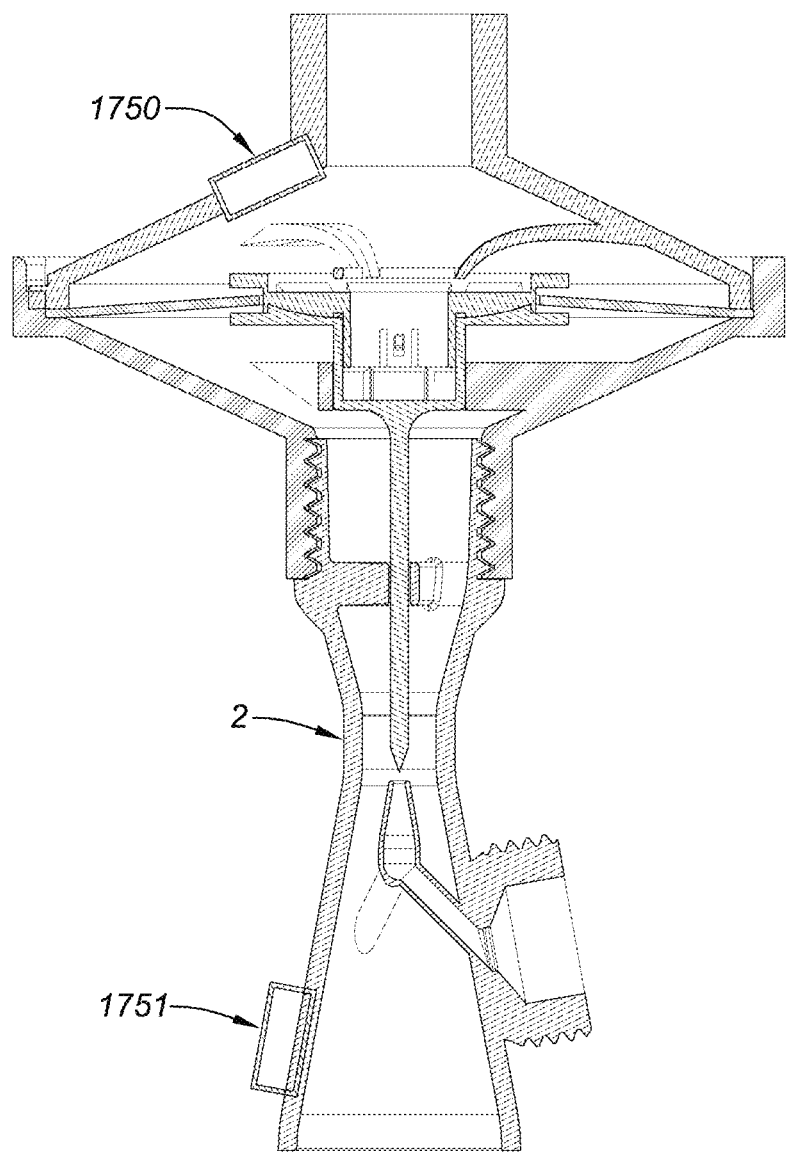
FIG. 17 is a side cutaway view of the ventilator/apparatus according to an embodiment of the invention having a sensors in multiple positions.

Referring now to FIG. 17, there is shown a side cutaway view of the ventilator/apparatus 2 according to an embodiment of the invention. The ventilator/apparatus 2 is that described herein, but having a sensor module 1750 positioned between the pressure force multiplier and the fluid port and a sensor module 1751 positioned between the venturi nozzle and the ambient air aperture. The sensor modules 1750/1751 may comprise any of the sensors described herein, for instance, pressure sensor, oxygen sensor, carbon dioxide sensor, temperature sensor, humidity sensor et al.

Figure 18:
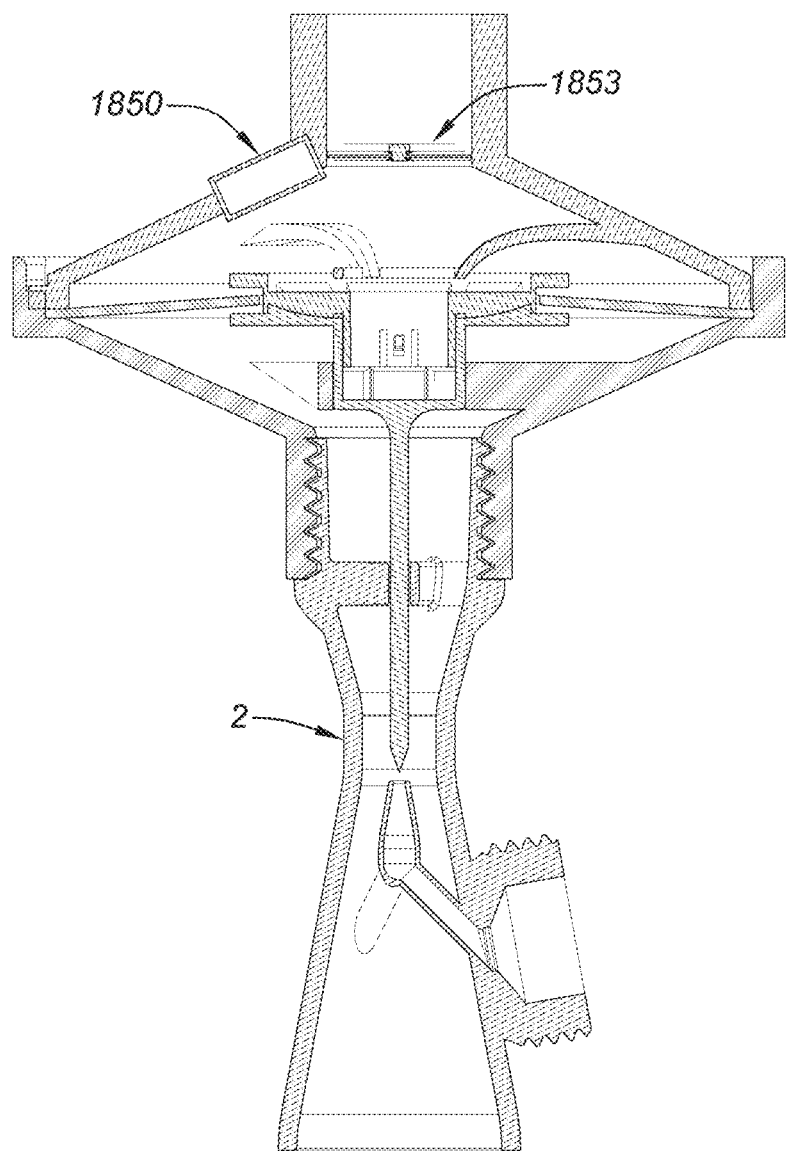
FIG. 18 is a side cutaway view of the ventilator/apparatus according to an embodiment of the invention having a spirometer in one position.

Referring now to FIG. 18 there is shown a side cutaway view of the ventilator/apparatus 2 according to an embodiment of the invention. The ventilator/apparatus 2 is that described herein, but having a spirometer 1853 positioned between the pressure force multiplier and the fluid port. A sensor module 1850 positioned between the pressure force multiplier and the fluid port is also shown, as seen in and described in relation to FIG. 15, for example.

Figure 19:
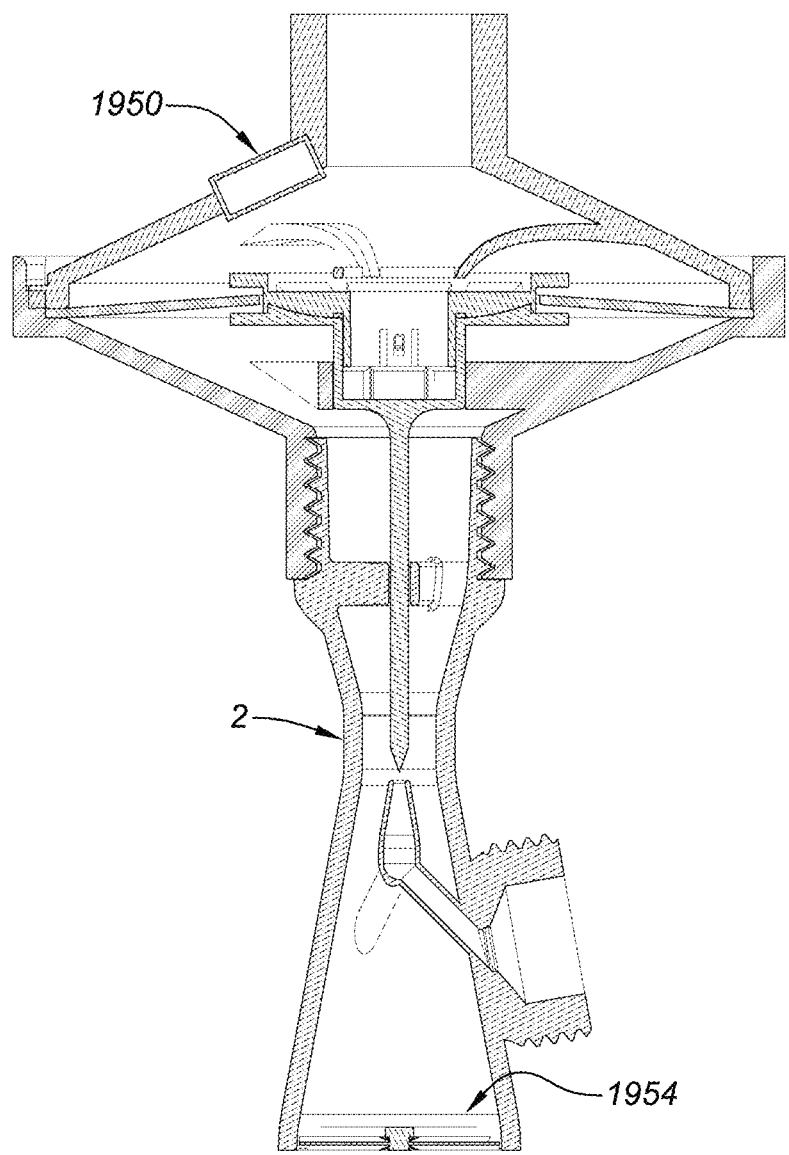
FIG. 19 is a side cutaway view of the ventilator/apparatus according to an embodiment of the invention having a spirometer in another position.

Referring now to FIG. 19 there is shown a side cutaway view of the ventilator/apparatus 2 according to an embodiment of the invention. The ventilator/apparatus 2 is that described herein, but having a spirometer 1954 positioned between the venturi nozzle and the ambient air aperture. A sensor module 1950 positioned between the pressure force multiplier and the fluid port is also shown, as seen in and described in relation to FIG. 15, for example.

Figure 20:
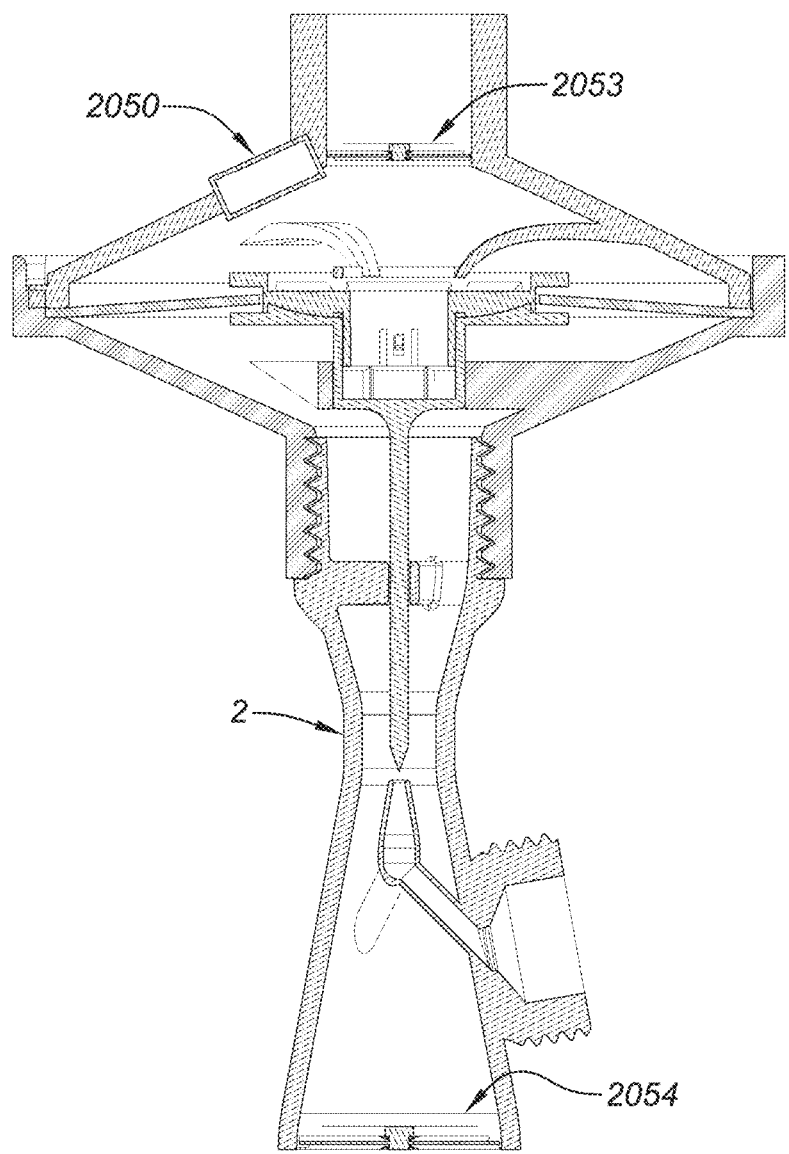
FIG. 20 is a side cutaway view of the ventilator/apparatus according to an embodiment of the invention having a spirometers in multiple positions.

FIG. 20 is a side cutaway view of the ventilator/apparatus 2 according to an embodiment of the invention having a multiple spirometers 2053 and 2054 in multiple positions. That is having a spirometer 2053 positioned between the pressure force multiplier and the fluid port and a spirometer 2054 positioned between the venturi nozzle and the ambient air aperture. A sensor module 2050 positioned between the pressure force multiplier and the fluid port is also shown, as seen in and described in relation to FIG. 15, for example.

Figure 21:
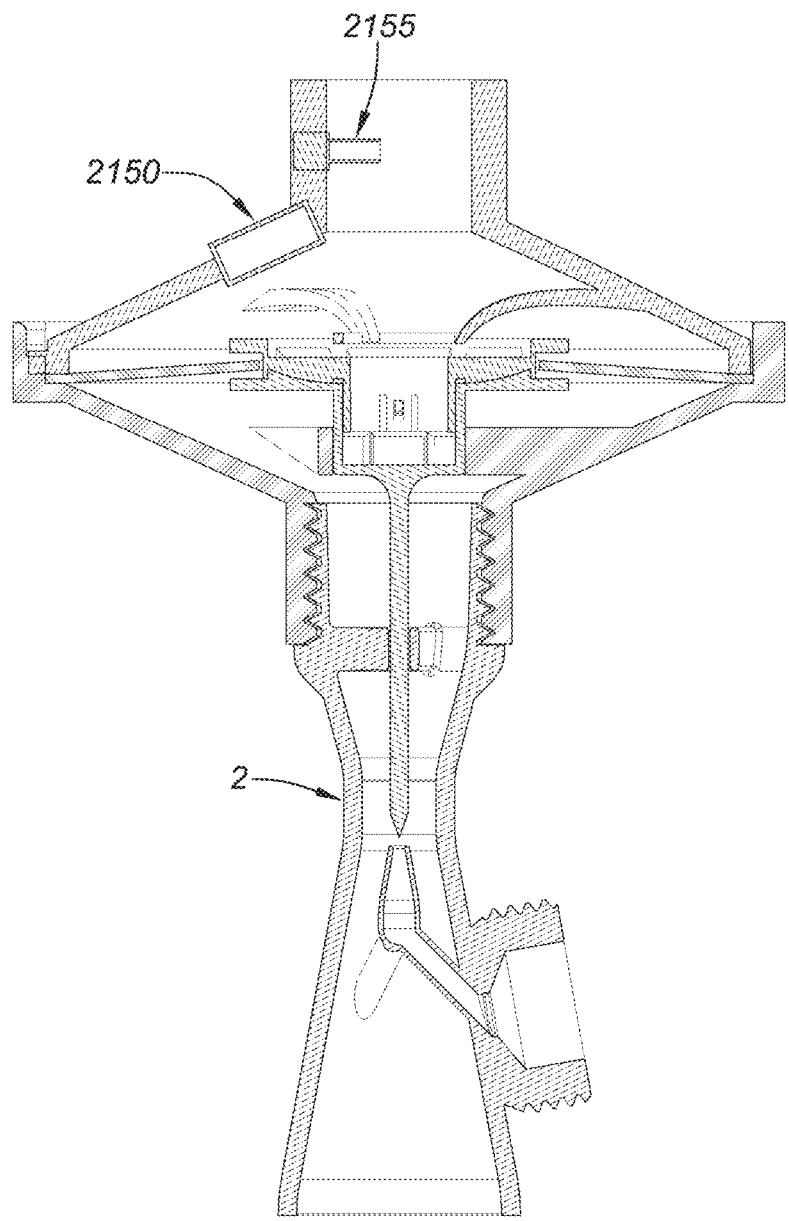
FIG. 21 is a side cutaway view of the ventilator/apparatus according to an embodiment of the invention having a pitot tube.

FIG. 21 is a side cutaway view of the ventilator/apparatus 2 according to an embodiment of the invention having a pitot tube 2155 between the pressure force multiplier and the fluid port. A sensor module 2150 positioned between the pressure force multiplier and the fluid port is also shown, as seen in and described in relation to FIG. 15, for example.

Figure 22:
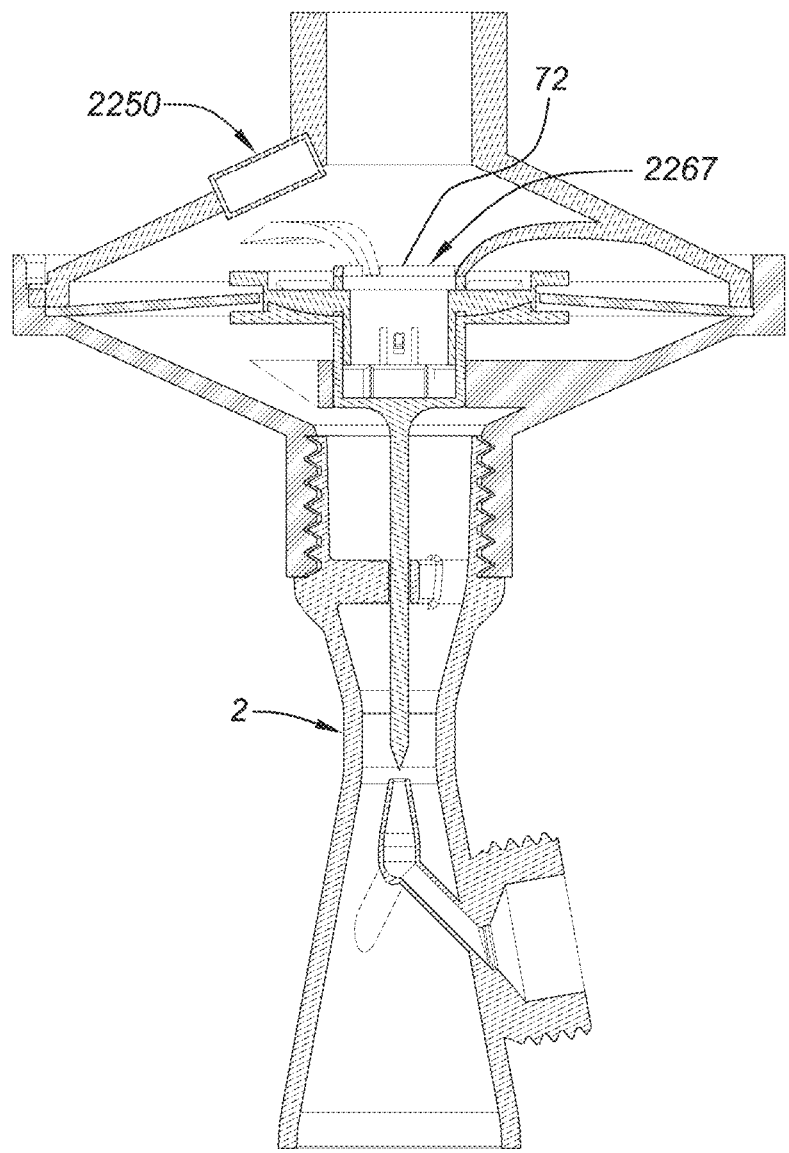
FIG. 22 is a side cutaway view of the ventilator/apparatus according to an embodiment of the invention having a piezo element.

FIG. 22 is a side cutaway view of the ventilator/apparatus 2 according to an embodiment of the invention having a piezo element 2267 at the limiter 72. A sensor module 2250 positioned between the pressure force multiplier and the fluid port is also shown, as seen in and described in relation to FIG. 15, for example.

Figure 23:
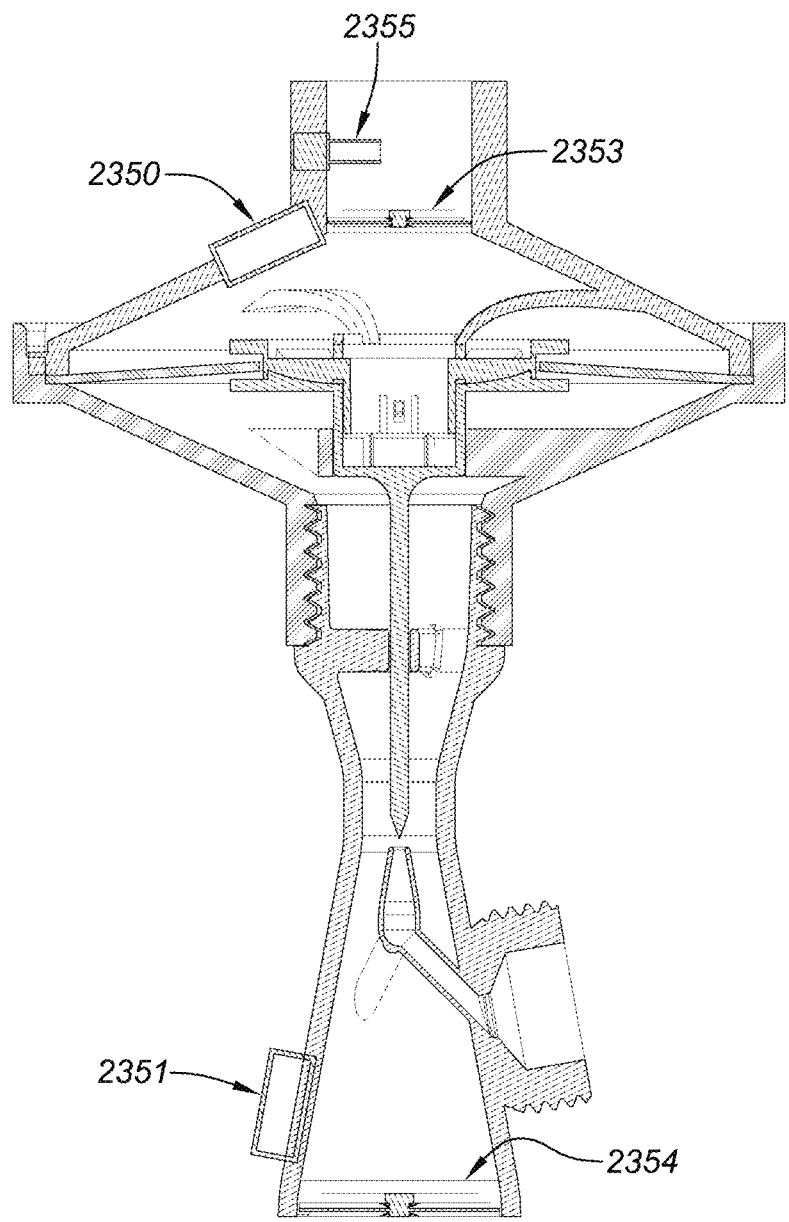
FIG. 23 is a side cutaway view of the ventilator/apparatus according to an embodiment of the invention having a sensors, spirometers, a pitot tube and piezo element in multiple positions.

FIG. 23 is a side cutaway view of the ventilator/apparatus 2 according to an embodiment of the invention having a sensors, spirometers, a pitot tube and piezo element in multiple positions—like numbers denote like features as shown in earlier embodiments. A sensor module 2350 positioned between the pressure force multiplier and the fluid port and a sensor module 2351 positioned between the venturi nozzle and the ambient air aperture is also shown, as seen in and described in relation to FIG. 17, for example. A pitot tube 2355 positioned between the pressure force multiplier and the fluid port is also shown, as seen in and described in relation to FIG. 21, for example.

Figure 24:
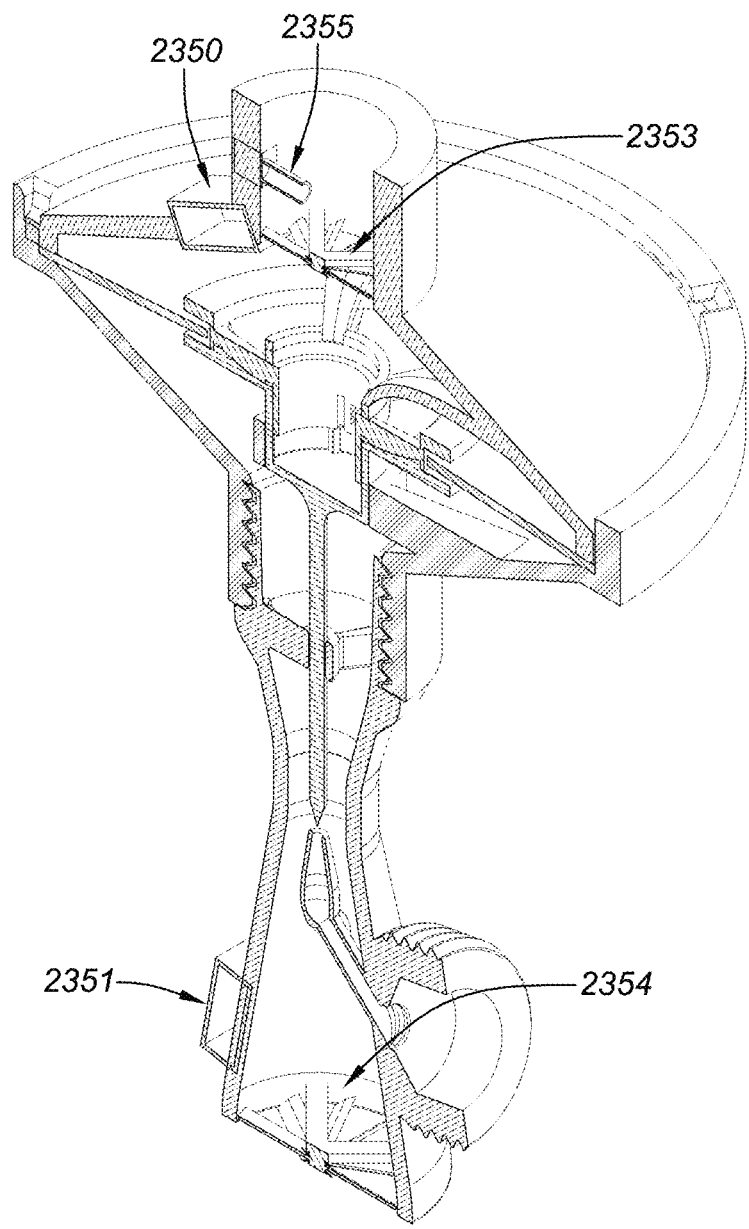
FIG. 24 is a perspective cutaway view of the ventilator/apparatus of FIG. 23.

FIG. 24 is a perspective cutaway view of the ventilator/apparatus 2 of FIG. 23.

Figure 25:
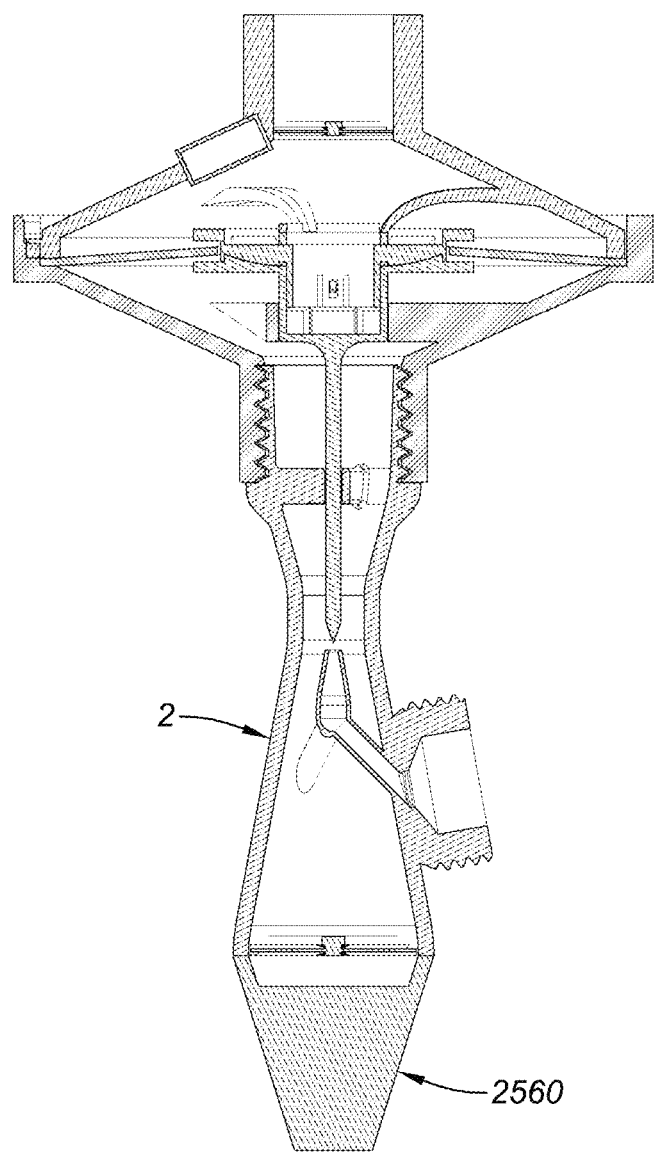
FIG. 25 is a side cutaway view of the ventilator/apparatus according to an embodiment of the invention having an active filter.

FIG. 25 is a side cutaway view of the ventilator/apparatus 2 according to an embodiment of the invention having an active filter 2560 positioned adjacent the ambient fluid aperture.

Figure 26:
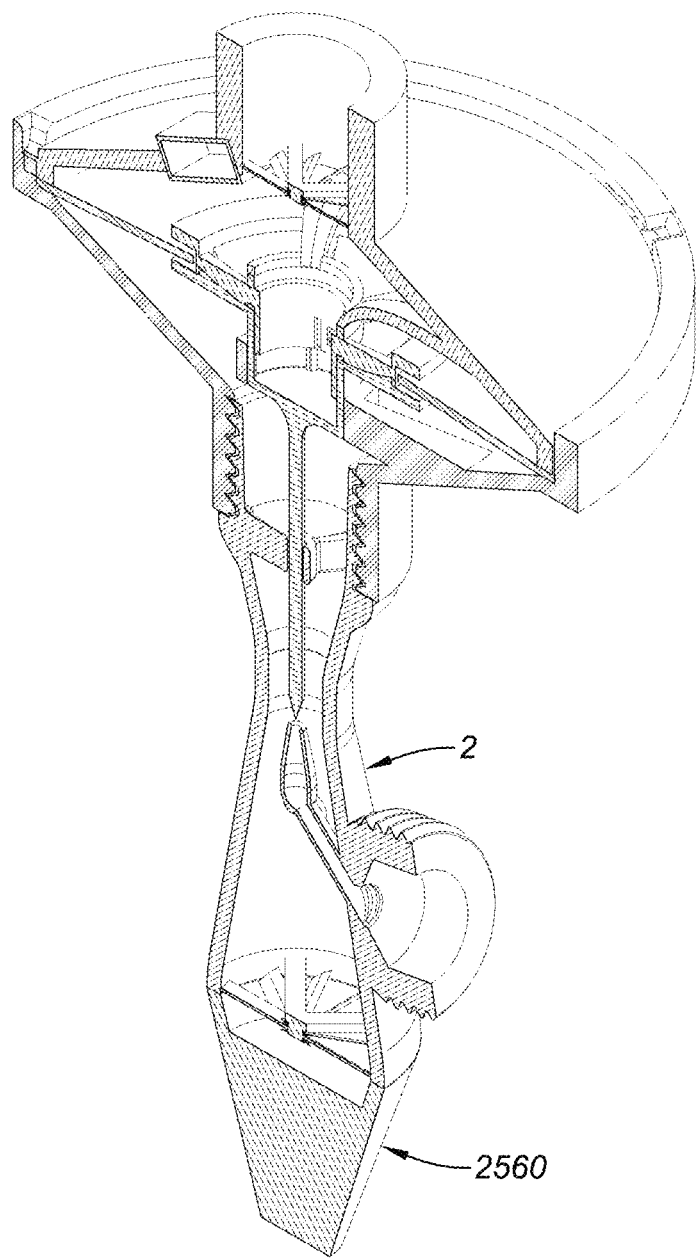
FIG. 26 is a perspective cutaway view of the ventilator/apparatus of FIG. 25.

FIG. 26 is a perspective cutaway view of the ventilator/apparatus of FIG. 25.

Figure 27:
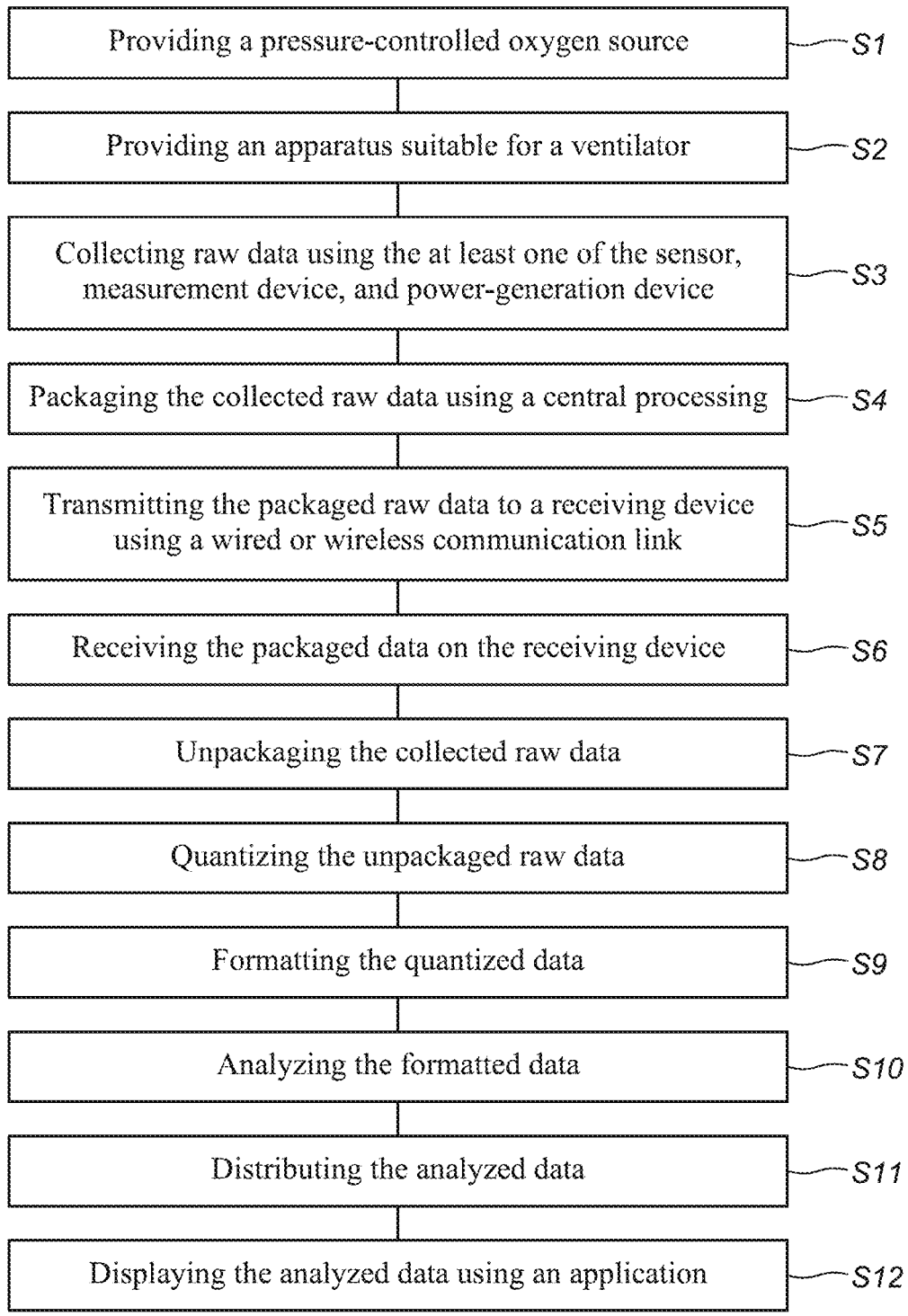
FIG. 27 is a flow chart of the method according to an embodiment of the invention.

FIG. 27 is a flow chart of the method according to an embodiment of the invention. Steps S1-S12 correspond to the steps defined herein.

Figure 28:
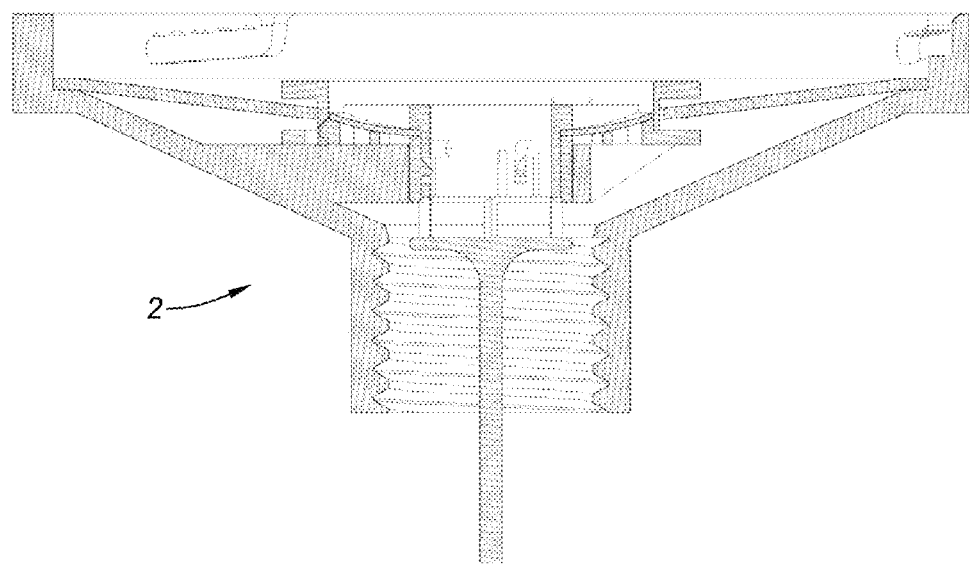
FIG. 28 is a side cutaway view of the ventilator/apparatus according to an embodiment of the invention without a fluid flow restrictor.

FIG. 28 is a side cutaway view of the ventilator/apparatus according to an embodiment of the invention without a fluid flow restrictor.

Figure 29:
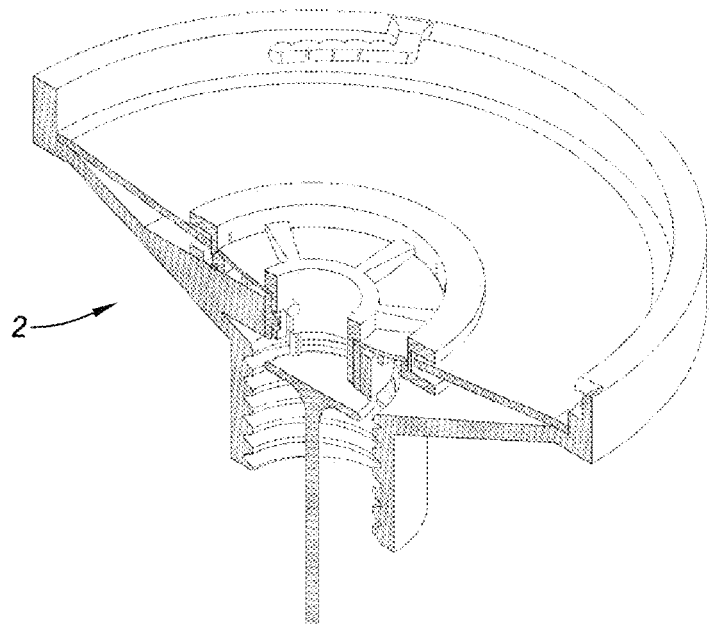
FIG. 29 is a perspective cutaway view of the ventilator/apparatus of FIG. 28.

FIG. 29 is a perspective cutaway view of the ventilator/apparatus of FIG. 28.

Figure 30:
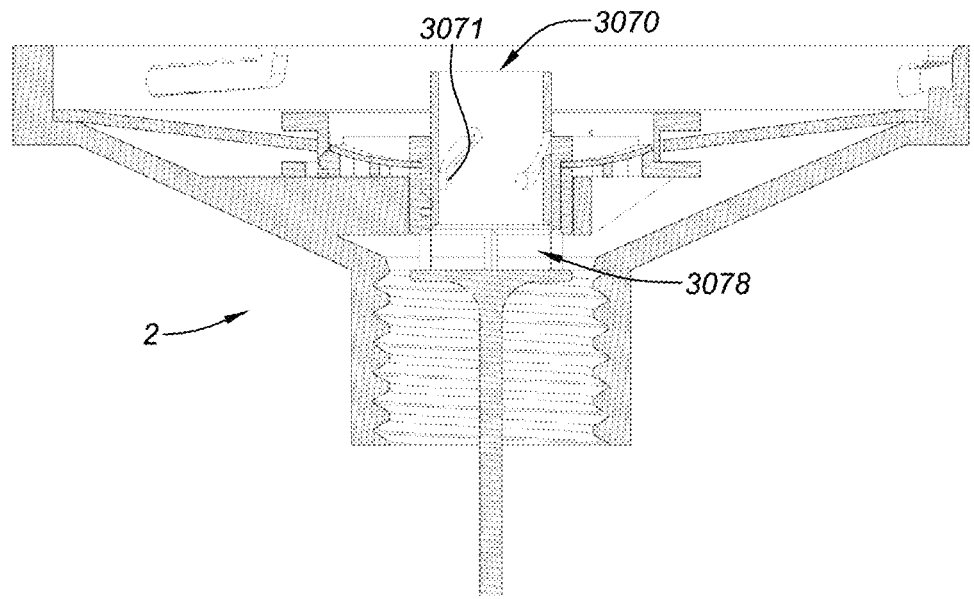
FIG. 30 is a side cutaway view of the ventilator/apparatus according to an embodiment of the invention with a fluid flow restrictor in an open position.

FIG. 30 is a side cutaway view of the ventilator/apparatus 2 according to an embodiment of the invention with a fluid flow restrictor 3070 in an open position. The ventilator 2 comprising exhalation windows 3078 for allowing fluid to exit the ventilator 2 during exhalation, and a fluid flow restrictor 3070 for at least selectively partially closing the exhalation windows 3078 to set the Positive End Expiratory Pressure (PEEP) of the patient. The fluid flow restrictor 3070 is in the shape of a collar and is positioned adjacent the vent ring, and held in place by a pair of pins 3071 so that it can be selectively adjusted linear to select the extent that the collar obstructs the exhalation windows 3078.

Figure 31:
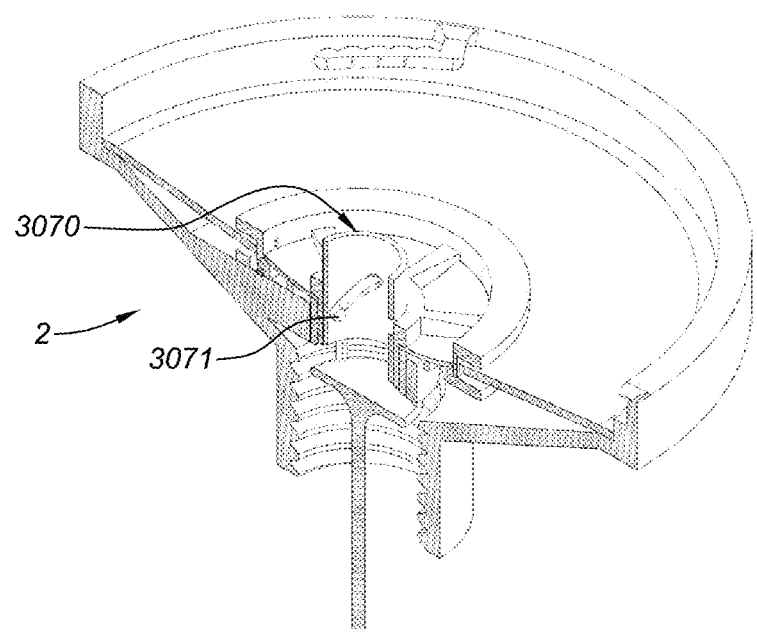
FIG. 31 is a perspective cutaway view of the ventilator/apparatus of FIG. 30.

FIG. 31 is a perspective cutaway view of the ventilator/apparatus of FIG. 30.

Figure 32:
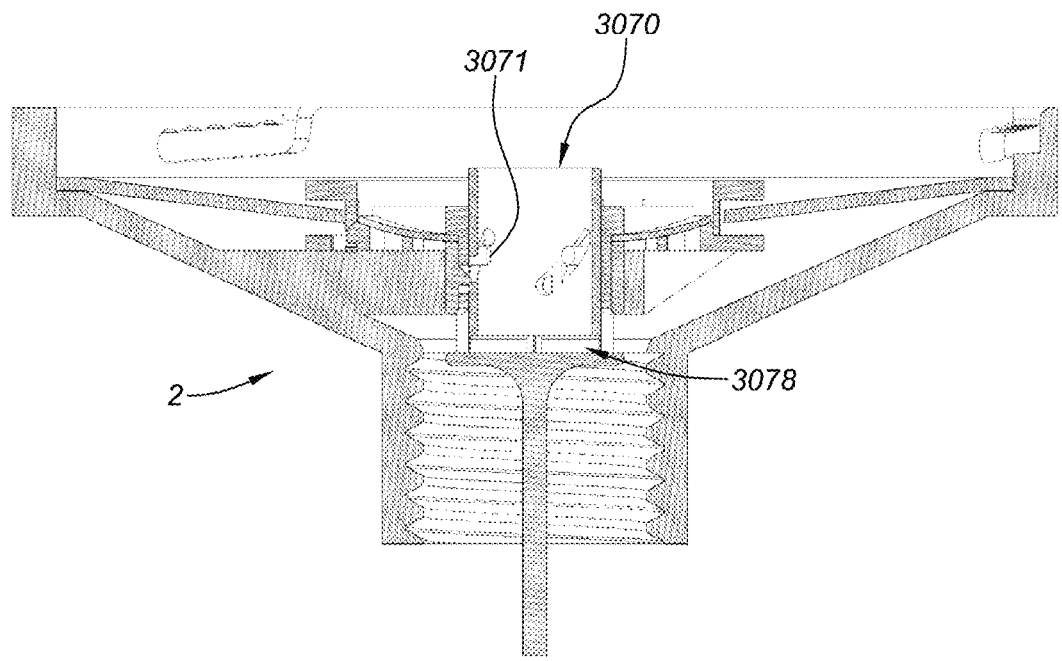
FIG. 32 is a side cutaway view of the ventilator/apparatus according to an embodiment of the invention with a fluid flow restrictor in a restricted position.

FIG. 32 is a side cutaway view of the ventilator/apparatus according to an embodiment of the invention with a fluid flow restrictor in a restricted position.

Figure 33:
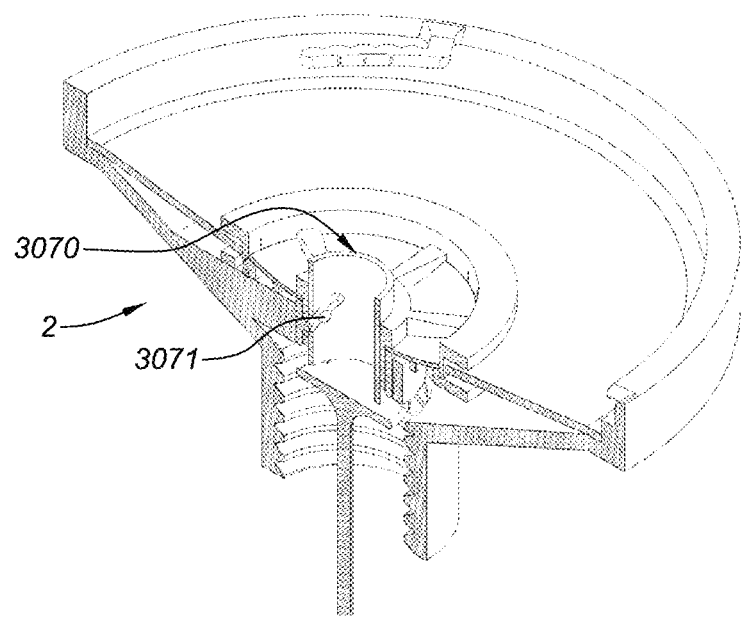
FIG. 33 is a perspective cutaway view of the ventilator/apparatus of FIG. 30.

FIG. 33 is a perspective cutaway view of the ventilator/apparatus of FIG. 30 in the open position.

CLAUSES

It will be understood that the following clauses form part of the specification and disclosure of the invention defined herein. More particularly, the invention herein may be defined by the combination of the features of the clauses as detailed below, and such clauses may be utilized to amend the combination of the features within the claims of this application.

1. A respirator apparatus including:
    a venturi nozzle for flow of a pressure-controlled fluid;
    an ambient fluid aperture in fluid communication with the venturi nozzle;
    a fluid port;
    a pressure force multiplier in fluid communication with the fluid port; and
    a valve moveable relative to the venturi nozzle between a start flow position and a stop flow position;
    where the pressure force multiplier is configured such that fluid forced into the fluid port actuates the valve relative to the venturi nozzle; and
    where the pressure force multiplier is configured such that fluid withdrawn from the fluid port actuates the valve relative to the venturi nozzle.

2. An apparatus suitable for a respirator, including:
    a venturi nozzle for flow of a pressure-controlled fluid;
    an ambient fluid aperture in fluid communication with the venturi nozzle;
    a fluid port;
    a pressure force multiplier in fluid communication with the fluid port; and
    a valve moveable relative to the venturi nozzle between a start flow position and a stop flow position;
    where the pressure force multiplier is configured such that fluid forced into the fluid port actuates the valve relative to the venturi nozzle; and
    where the pressure force multiplier is configured such that fluid withdrawn from the fluid port actuates the valve relative to the venturi nozzle.

3. The apparatus of Clause 1 or Clause 2, where the pressure force multiplier is configured such that fluid forced into the fluid port actuates the valve relative to the venturi nozzle to a stop flow position; and
where the pressure force multiplier is configured such that fluid withdrawn from the fluid port actuates the valve relative to the venturi nozzle to a start flow position.

4. The apparatus of Clause 1 or Clause 2, where the pressure force multiplier is configured such that fluid forced into the fluid port actuates the valve relative to the venturi nozzle to a start flow position; and where the pressure force multiplier is configured such that fluid withdrawn from the fluid port actuates the valve relative to the venturi nozzle to a stop flow position.

5. The apparatus of Clause 1 or Clause 2, where the pressure force multiplier is configured such that fluid forced into the fluid port actuates the valve relative to the venturi nozzle to an active flow position between the start flow position and stop flow position; and where the pressure force multiplier is configured such that fluid withdrawn from the fluid port actuates the valve relative to the venturi nozzle to an active flow position between the start flow position and stop flow position.

6. The apparatus of any of Clauses 1 to 5, where a pressure-controlled fluid includes oxygen, an ambient fluid includes ambient air, fluid forced into the fluid port includes air exhaled into an air port, and fluid withdrawn from the fluid port includes air inhaled from an air port.

7. The apparatus of any of Clauses 1 to 5, where the pressure force multiplier is positioned between the venturi nozzle and the fluid port.

8. The apparatus of any of Clauses 1 to 5, where the venturi nozzle is positioned between the pressure force multiplier and the fluid port.

9. The apparatus of any of Clauses 1 to 5, where the venturi nozzle is positioned between the ambient fluid aperture and the fluid port.

10. The apparatus of any of Clauses 1 to 9, including a pressure regulator for regulating the flow of a pressure-controlled fluid, the pressure regulator including:
    a housing formed to include a bore therein;
    a piston moveably disposed within the bore, where the piston includes an annular lip adjacent a first end thereof;
    a spring disposed within the bore, and including a first end and a second end;
    an adjustment cap moveably disposed in the bore, where the adjustment cap is formed to include a plurality of key slots formed therein;
    where:
        the first end of the spring is in physical contact with the annular lip; and
        the second end of the spring is in physical contact with the adjustment cap where:
            rotating the adjustment cap in a first direction causes the adjustment cap to compress the first spring;
            rotating the adjustment cap in a second and opposite direction causes the adjustment cap to decompress the spring;
            rotating the adjustment cap in the first direction increases the output pressure of the pressure regulator;
            rotating the adjustment cap in the second direction decreases the output pressure of the pressure regulator;
        the bore is defined by a cylindrical wall;
        the cylindrical wall is formed to include first threading therein;
        the adjustment cap is formed to include second threading formed on a periphery thereof;
        the second threading is configured to mesh with the first threading.

11. The apparatus of any of Clauses 1 to 10, where the pressure force multiplier includes a diaphragm.

12. The apparatus of any of Clauses 1 to 11, where the pressure force multiplier is bi-stable.

13. The apparatus of any of Clauses 3 to 12, where the pressure force multiplier is biased toward the stop flow position.

14. The apparatus of any of Clauses 3 to 12, where the pressure force multiplier is biased toward the start flow position.

15. The apparatus of any of Clauses 1 to 10, where the pressure force multiplier includes at least one flap.

16. The apparatus of any of Clauses 1 to 15, where the apparatus is solely mechanical.

17. The apparatus of any of Clauses 3 to 16, where in the start flow position or an active flow position a mixture of pressure-controlled fluid and ambient fluid is allowed to flow to the fluid port.

18. The apparatus of Clause 17, where the flow of the mixture is modulated in real-time.

19. The apparatus of any of Clauses 1 to 18, where the valve includes a flange that is connected to the pressure force multiplier.

20. The apparatus of any of Clauses 1 to 18, where the valve includes a stem with a tapered end, where the tapered end enters a venturi opening in the venturi nozzle in the stop position to substantially close the venturi opening.

21. The apparatus of Clause 20, where the stem is connected to the pressure force multiplier.

22. The apparatus of any of Clauses 1 to 18, where the valve includes a switch.

23. The apparatus of any of Clauses 1 to 18, where the valve includes a flap valve.

24. The apparatus of any of Clauses 1 to 18, where the valve includes a spring-loaded shuttle system.

25. The apparatus of any of Clauses 1 to 18, where the valve is slidable.

26. The apparatus of any of Clauses 1 to 25, where the valve is solely mechanical.

27. The apparatus of any of Clauses 1 to 26, where the ambient fluid aperture includes a fluid exhaust.

28. The apparatus of Clause 27, where the valve is configured to be actuated relative to the venturi nozzle while simultaneously opening the fluid exhaust.

29. The apparatus of any of Clauses 1 to 28, further including at least one filter detachably connected to the ambient fluid aperture.

30. The apparatus of Clause 29, where the at least one filter includes pores of about 3 μm.

31. The apparatus of any of Clauses 1 to 30, further including a respirator.

32. The apparatus of Clause 31, where the respirator is in fluid communication with the fluid port.

33. The apparatus of any of Clauses 1 to 32, where the fluid is a liquid.

34. The apparatus of any of Clauses 1 to 33, where the apparatus is injection molded.

35. The apparatus of any of Clauses 1 to 33, where the apparatus is 3D printed.

36. The apparatus of any of Clauses 1 to 35, where apparatus is configured to be mobile.

37. The apparatus of any of Clauses 1 to 36, where apparatus is configured to be re-usable.

38. The apparatus of any of Clauses 1 to 37 for use in controlling the flow of air and/or oxygen into a respirator.

39. The apparatus of any of Clauses 1 to 38 for use in controlling the flow of scrubbed air and/or oxygen into a respirator.

40. The apparatus of any of Clauses 1 to 39 for use in treating a respiratory condition.

41. The apparatus of any of Clauses 1 to 40 for use in treating COVID-19.

42. A method of using an apparatus suitable for a respirator, the method including:
   providing a source of pressure-controlled fluid;
   providing an apparatus suitable for a respirator, including:
   a venturi nozzle for receiving a flow of the pressure-controlled fluid;
   an ambient fluid aperture in fluid communication with the venturi nozzle;
   a fluid port;
   a pressure force multiplier in fluid communication with the fluid port; and
   a valve moveable relative to the venturi nozzle between a start flow position, in which the pressure-controlled fluid mixes with the ambient fluid, and a stop flow position;
   actuating the valve relative to the venturi nozzle in response to fluid forced into the fluid port; and
   actuating the valve relative to the venturi nozzle in response to fluid withdrawn from the fluid port.

43. The method of Clause 42, where the apparatus is solely mechanical.

44. The method of Clause 42 or Clause 43, further including adjusting the pressure of the pressure-controlled fluid.

45. The method of any of Clauses 42 to 44, where the method is for using the apparatus in treating a living patient who inhales and exhales breath, where the pressure-controlled fluid is pressure-controlled oxygen, and where the fluid is air, the method including:
   connecting the apparatus to a respirator;
   placing the respirator in gaseous communication with the patient and with the source of pressure-controlled oxygen;
   in response to inhalation by the patient, starting oxygen flow into the respirator, mixing the oxygen with ambient air to generate enriched air, and delivering the enriched air to the patient;
   in response to exhalation by the patient, stopping oxygen flow into the respirator, and exhausting exhalation air from the respirator.

46. The method of Clause 45, where the enriched air has an FiO2 of at least 26%.

47. The method of any of Clauses 42 to 44, where the method is for using the apparatus in treating a living patient who inhales and exhales breath, where the pressure-controlled fluid is pressure-controlled filtered air, and where the fluid is air, the method including:
   connecting the apparatus to a respirator;
   placing the respirator in gaseous communication with the patient and with the source of pressure-controlled filtered air;
   in response to inhalation by the patient, starting oxygen flow into the respirator, mixing the pressure-controlled filtered air with ambient air to generate scrubbed air, and delivering the scrubbed air to the patient;
   in response to exhalation by the patient, stopping oxygen flow into the respirator, and exhausting exhalation air from the respirator.

48. The method of Clause 47, where the scrubbed air has an $FiO_2$ of at least 26%.

49. The method of any of Clauses 42 to 48, further including walking and/or running while utilizing the apparatus and a respirator.

50. The method of any of Clauses 42 to 49, further including initiating use of the apparatus and respirator to treat allergies.

51. The method of any of Clauses 42 to 49, further including initiating use of the apparatus and respirator to treat ARDS.

52. The method of any of Clauses 42 to 49, further including initiating use of the apparatus and respirator to treat sleep apnea.

53. The method of any of Clauses 42 to 49, further including initiating use of the apparatus and respirator to treat COPD.

54. The method of any of Clauses 42 to 49, further including initiating use of the apparatus and respirator to treat infection by the COVID-19 virus.

55. The method of any of Clauses 42 to 54, further including filtering the ambient air.

56. The method of any of Clauses 42 to 55, further including filtering exhaled breath from the patient.

57. A pressure force multiplier including a sealed end and an open end, where the sealed end is in fluid communication with a valve to define a fixed volume between the sealed end and the valve, where the pressure force multiplier is configured such that a change in pressure in the open end causes a change in pressure in the sealed end which actuates the valve.

58. The pressure force multiplier of Clause 57, configured such that a negative pressure in the open end causes a reduction in pressure in the sealed end which actuates the valve.

59. The pressure force multiplier of Clause 57, configured such that a positive pressure in the open end causes an increase in pressure in the sealed end which actuates the valve.

60. The pressure force multiplier of any of Clauses 57 to 59, where the actuation of the valve activates a humidifier.

61. The pressure force multiplier of any of Clauses 57 to 59, where the actuation of the valve generates a change in a visual indicator.

62. The pressure force multiplier of Clause 61, where the change in visual indicator represents a change of pressure in the open end.

63. The pressure force multiplier of Clause 62, where the change of pressure in the open end is caused by inhalation and/or exhalation of a patient.

As used in this document, both in the description and in the claims, and as customarily used in the art, the words "substantially," "approximately," and similar terms of approximation are used to account for manufacturing tolerances, manufacturing variations, and manufacturing imprecisions that are inescapable parts of fabricating any mechanism or structure in the physical world.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. The purpose of the Abstract of this document is to enable the U.S. Patent and Trademark Office, as well as readers who are not familiar with patent or legal terms or phraseology, to determine quickly from a cursory inspection the nature and essence of the technical disclosure of the application. The Abstract is not intended to define the invention, nor is it intended to limit to the scope of the invention. The purpose of the clauses of this document is to provide support for claims in any later-file foreign patent applications claiming priority to this document. The clauses are not intended to define the invention, nor are they intended to limit to the scope of the invention. Therefore, the invention is not to be restricted or limited except in accordance with the following claims and their legal equivalents.

What is claimed is:

1. A ventilator connectable to the airway of a living patient, comprising: a venturi, comprising a throat,
    a venturi nozzle;
    a venturi opening in the venturi nozzle through which pressure-controlled oxygen flows outward, wherein said venturi opening opens to said throat, and wherein said venturi opening and said throat are substantially longitudinally aligned;
    an ambient air aperture in fluid communication with said venturi nozzle and with ambient air;
    a fluid port configured to be in fluid communication with the airway of the patient;
    a pressure force multiplier in fluid communication with said fluid port, wherein said pressure force multiplier includes at least one opening defined therethrough; said pressure force multiplier comprising at least one flap movable between an open position and a closed position relative to said at least one opening; and
    a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat;
    wherein during exhalation of the patient into said fluid port, said pressure force multiplier is configured to actuate said valve along said axis of movement relative to said venturi nozzle to close said venturi nozzle;
    wherein during inhalation of the patient through said fluid port, said pressure force multiplier is configured to actuate said valve along said axis of movement relative to said venturi nozzle;
    wherein said axis of movement of said valve is substantially longitudinally aligned with a longitudinal direction of said throat; and
    further comprising at least one sensor, measurement device, and/or power-generation device.

2. The ventilator of claim 1, wherein the at least one sensor, measurement device, and/or power-generation device is a sensor selected from a group consisting of: a pressure sensor, an oxygen sensor, a carbon dioxide sensor, a temperature sensor, a humidity sensor, and a piezo sensor.

3. The ventilator of claim 1, wherein the at least one sensor, measurement device, and/or power-generation device is a measurement device selected from a group consisting of: a spirometer measurement device and a pitot measurement probe.

4. The ventilator of claim 1, wherein the at least one sensor, measurement device, and/or power-generation device is a power-generation device selected from a group consisting of: a piezo electrical generator and a spirometer electrical generator.

5. The ventilator of claim 1, wherein one of the at least one sensor, measurement device, and/or power-generation device is positioned between the venturi nozzle and the ambient air aperture.

6. The ventilator of claim 1, wherein one of the at least one sensor, measurement device, and/or power-generation device is positioned between the pressure force multiplier and the fluid port.

7. The ventilator of claim 1, wherein, for collecting differential data, the at least one sensor, measurement device, and/or power-generation device comprises two sensors, two measurement devices, or two power-generation devices, wherein one of the two sensors, the two measurement devices, or the two power-generation devices is positioned between the venturi nozzle and the ambient air aperture, and the other one of the two sensors, the two measurement devices, or the two power-generation devices is positioned between the pressure force multiplier and the fluid port.

8. The ventilator of claim 1, further comprising a central processing unit for packaging raw data collected by the at least one sensor, measurement device, and/or power-generation device.

9. The ventilator of claim 1, wherein the at least one sensor, measurement device, and/or power-generation device is a sensor, wherein the sensor comprises a motion sensor.

10. The ventilator of claim 1, further comprising exhalation windows for allowing fluid to exit the ventilator during the exhalation of the patient, and a fluid flow restrictor for at least selectively partially closing the exhalation windows to set a Positive End Expiratory Pressure (PEEP) of the patient.

11. An apparatus suitable for use with a respirator, comprising:
a venturi, comprising:
a throat,
a venturi nozzle, and;
a venturi opening in the venturi nozzle through which pressure-controlled fluid flows outward, wherein said venturi opening opens to said throat, and wherein said venturi opening and said throat are substantially longitudinally aligned;
an ambient fluid aperture in fluid communication with said venturi nozzle and with an ambient fluid;
a fluid port;
a pressure force multiplier in fluid communication with said fluid port; and
a valve moveable along an axis of movement relative to said venturi opening in said venturi nozzle between a start flow position that causes entrainment of the ambient fluid by the flow of pressure-controlled fluid within said throat, and a stop flow position that ceases entrainment of the ambient fluid by the flow of pressure-controlled fluid within said throat;
wherein said pressure force multiplier is configured such that fluid forced into said fluid port actuates said valve along said axis of movement relative to said venturi nozzle to close said venturi nozzle;
wherein said pressure force multiplier is configured such that fluid withdrawn from said fluid port actuates said valve along said axis of movement relative to said venturi nozzle;
wherein said axis of movement of said valve is substantially longitudinally aligned with a longitudinal direction of said throat;
wherein said pressure force multiplier is positioned between said venturi nozzle and said fluid port; and
further comprising at least one sensor, measurement device, and/or power-generation device.

12. The apparatus of claim 11, wherein the at least one sensor, measurement device, and/or power-generation device is a sensor selected from a group consisting of: a pressure sensor, an oxygen sensor, a carbon dioxide sensor, a temperature sensor, a humidity sensor, and a piezo sensor.

13. The apparatus of claim 11, wherein the at least one sensor, measurement device, and/or power-generation device is a measurement device selected from a group consisting of: a spirometer measurement device and a pitot measurement probe.

14. The apparatus of claim 11, wherein the at least one sensor, measurement device, and/or power-generation device is a power-generation device selected from a group consisting of: a piezo electrical generator and a spirometer electrical generator.

15. The apparatus of claim 11, wherein one of the at least one sensor, measurement device, and/or power-generation device is positioned between the venturi nozzle and the ambient air aperture.

16. The apparatus of claim 11, wherein one of the at least one sensor, measurement device, and/or power-generation device is positioned between the pressure force multiplier and the fluid port.

17. The apparatus of claim 11, wherein, for collecting differential data, the at least one sensor, measurement device, and/or power-generation device comprises two sensors, two measurement devices, or two power-generation devices, wherein one of the two sensors, two measurement devices, or two power-generation devices is positioned between the venturi nozzle and the ambient air aperture, and the other one of the two sensors, two measurement devices, or two power-generation devices is positioned between the pressure force multiplier and the fluid port.

18. The apparatus of claim 11, comprising a central processing unit for packaging raw data collected by the at least one sensor, measurement device, and/or power-generation device.

19. The apparatus of claim 11, the at least one sensor, measurement device, and/or power-generation device is a sensor, wherein the sensor comprises a motion sensor.

20. The apparatus of claim 11, further comprising at least one fluid gate for allowing fluid to exit the apparatus when the fluid is forced into said fluid port, and a fluid flow restrictor for at least selectively partially closing the at least one fluid gate.

21. The apparatus of claim 11, wherein said pressure force multiplier is configured such that the fluid forced into said fluid port actuates said valve along said axis of movement relative to said venturi nozzle to said stop flow position; and wherein the pressure force multiplier is configured such that the fluid withdrawn from said fluid port actuates said valve along said axis of movement relative to said venturi nozzle to said start flow position.

22. The apparatus of claim 11, wherein said pressure force multiplier is configured such that the fluid forced into said fluid port actuates said valve along said axis of movement relative to said venturi nozzle to said start flow position; and wherein said pressure force multiplier is configured such that the fluid withdrawn from said fluid port actuates said valve along said axis of movement relative to said venturi nozzle to said stop flow position.

23. The apparatus of claim 11, further comprising a pressure regulator for regulating the flow of the pressure-controlled fluid, the pressure regulator comprising:
a housing formed to include a bore therein;
a piston moveably disposed within said bore, wherein said piston comprises an annular lip adjacent a first end thereof;
a spring disposed within said bore, and comprising a first end and a second end; an adjustment cap moveably disposed in said bore, wherein said adjustment cap is formed to include a plurality of key slots formed therein;

wherein:

said first end of said spring is in physical contact with said annular lip; and said second end of said spring is in physical contact with said adjustment cap wherein:

rotating said adjustment cap in a first direction causes said adjustment cap to compress said first spring;

rotating said adjustment cap in a second and opposite direction causes said adjustment cap to decompress said spring;

rotating said adjustment cap in said first direction increases the output pressure of the pressure regulator;

rotating said adjustment cap in said second direction decreases the output pressure of the pressure regulator;

said bore is defined by a cylindrical wall;

said cylindrical wall is formed to include a first threading therein;

said adjustment cap is formed to include a second threading formed on a periphery thereof;

and said second threading is configured to mesh with said first threading.

24. The apparatus of claim 11, wherein the pressure force multiplier comprises a diaphragm.

25. The apparatus of claim 11, wherein said valve includes a stem with a tapered end, wherein said tapered end enters said venturi opening in said venturi nozzle in said stop position to substantially close said venturi opening.

26. The apparatus of claim 11, further comprising at least one filter detachably connected to said ambient fluid aperture.

27. The apparatus of claim 11, wherein said pressure-controlled fluid is a liquid.

28. A method of using an apparatus suitable for a ventilator and collecting data from a patient, the method comprising:

providing a pressure-controlled oxygen source;

providing an apparatus suitable for a ventilator, comprising:

a venturi, comprising a throat, a venturi nozzle;

a venturi opening in said venturi nozzle through which pressure-controlled oxygen flows outward, wherein said venturi opening opens to said throat, and wherein said venturi opening and said throat are substantially longitudinally aligned;

an ambient air aperture in fluid communication with said venturi nozzle and with ambient air;

a fluid port;

a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat;

placing said fluid port in fluid communication with an airway of the patient;

in response to exhalation by the patient through said fluid port, causing said at least one flap to move to said closed position relative to said at least one opening, and actuating said valve along said axis of movement relative to said venturi nozzle to close said venturi nozzle; and in response to inhalation by the patient through said fluid port, causing said at least one flap to move to said open position relative to said at least one opening, and actuating said valve along said axis of movement relative to said venturi nozzle; and wherein said axis of movement of the valve is substantially longitudinally aligned with the longitudinal direction of the throat; and further comprising at least one sensor, measurement device, and/or power-generation device; and collecting raw data using the at least one sensor, measurement device, and/or power-generation device;

packaging the collected raw data using a central processing unit;

transmitting the packaged raw data to a receiving device using a wired or wireless communication link;

receiving the packaged data on the receiving device;

unpackaging the collected raw data;

quantizing the unpackaged raw data;

formatting the quantized data;

analyzing the formatted data;

distributing the analyzed data; and displaying the analyzed data using an application.

29. The method of claim 28, wherein the at least one sensor, measurement device, and/or power-generation device is a sensor selected from a group consisting of: a pressure sensor, an oxygen sensor, a carbon dioxide sensor, a temperature sensor, a humidity sensor, and a piezo sensor.

30. The method of claim 28, wherein the at least one sensor, measurement device, and/or power-generation device is a measurement device selected from a group consisting of: a spirometer measurement device and a pitot measurement probe.

31. The method of claim 28, wherein the at least one sensor, measurement device, and/or power-generation device is a power-generation device selected from a group consisting of: a piezo electrical generator and a spirometer electrical generator.

32. The method of claim 28, comprising a step of coupling the central processing unit to the ventilator.

33. The method of claim 28, wherein using the wireless communication link comprises using at least one wireless protocol.

34. The method of claim 28, wherein using the wired communication link comprises using at least one of a USB, serial, 1-wire, and parallel.

35. The method of claim 28, further comprising displaying the analyzed data using a smart device.

36. The method of claim 35, wherein the smart device comprises at least one of a mobile communication device, a tablet, a patient interface display, a laptop computer, and a desktop computer.

* * * * *